(12) United States Patent
Suwa et al.

(10) Patent No.: US 9,453,105 B2
(45) Date of Patent: Sep. 27, 2016

(54) EPOXY AND ALKOXYSILYL GROUP-CONTAINING SILSESQUIOXANE AND COMPOSITION THEREOF

(71) Applicant: JNC CORPORATION, Tokyo (JP)

(72) Inventors: Kazuya Suwa, Chiba (JP); Ryota Mineo, Chiba (JP); Tomoyuki Ooba, Chiba (JP)

(73) Assignee: JNC CORPORATION, Tokyo (JP)

( * ) Notice: Subject to any disclaimer, the term of this patent is extended or adjusted under 35 U.S.C. 154(b) by 0 days.

(21) Appl. No.: 14/428,969

(22) PCT Filed: Sep. 17, 2013

(86) PCT No.: PCT/JP2013/075051
§ 371 (c)(1),
(2) Date: Jul. 5, 2015

(87) PCT Pub. No.: WO2014/046095
PCT Pub. Date: Mar. 27, 2014

(65) Prior Publication Data
US 2015/0368397 A1    Dec. 24, 2015

(30) Foreign Application Priority Data

Sep. 18, 2012 (JP) ................................ 2012-204512
Apr. 23, 2013 (JP) ................................ 2013-090624

(51) Int. Cl.

| | | |
|---|---|---|
| H01L 23/29 | (2006.01) | |
| C08G 65/22 | (2006.01) | |
| C08G 77/04 | (2006.01) | |
| C08G 77/18 | (2006.01) | |
| H01L 33/56 | (2010.01) | |
| C09D 163/00 | (2006.01) | |
| C08L 83/04 | (2006.01) | |
| C07F 7/08 | (2006.01) | |
| C09K 11/77 | (2006.01) | |
| C07F 7/21 | (2006.01) | |
| H01L 33/50 | (2010.01) | |

(52) U.S. Cl.
CPC .............. *C08G 65/22* (2013.01); *C07F 7/084* (2013.01); *C07F 7/21* (2013.01); *C08G 77/045* (2013.01); *C08G 77/18* (2013.01); *C08L 83/04* (2013.01); *C09D 163/00* (2013.01); *C09K 11/7734* (2013.01); *C09K 11/7774* (2013.01); *H01L 23/296* (2013.01); *H01L 33/56* (2013.01); *C08G 2190/00* (2013.01); *H01L 33/501* (2013.01); *H01L 2924/0002* (2013.01)

(58) Field of Classification Search
None
See application file for complete search history.

(56) References Cited

FOREIGN PATENT DOCUMENTS

| | | |
|---|---|---|
| JP | 61-112334 | 5/1986 |
| JP | 02-289611 | 11/1990 |
| JP | 2003-273292 | 9/2003 |
| JP | 2006-299099 | 11/2006 |
| JP | 2010-083955 | 4/2010 |
| JP | 2010-254814 | 11/2010 |
| JP | 2010-265410 | 11/2010 |
| JP | 2012-197338 | 10/2012 |
| JP | 2012-251058 | 12/2012 |
| JP | 2012-251166 | 12/2012 |
| WO | 2004/024741 | 3/2004 |
| WO | 2012/111765 | 8/2012 |
| WO | 2013/005633 | 1/2013 |

OTHER PUBLICATIONS

Abstract for CN 103288867 (Sep. 11, 2013).*
Machine generated translation of CN 103288867 into English (no date).*
Machine generated translation of JP 2010-083955 into English (no date).*
"International Search Report (Form PCT/ISA/210)", mailed on Dec. 3, 2013, with English translation thereof, pp. 1-4, in which five of the listed references (WO2012/111765, JP2010-254814, JP2010-083955, WO2013/005633 and JP2012-197338) were cited.

* cited by examiner

*Primary Examiner* — Marc Zimmer
(74) *Attorney, Agent, or Firm* — Jianq Chyun IP Office

(57) ABSTRACT

A silicon compound is described, being obtained by a hydrosilylation reaction of the following compound (a), compound (b) and compound (c). Compound (a) is a silsesquioxane derivative having two or more SiH in one molecule. Compound (b) is a compound having, in one molecule, epoxy and/or oxetanyl and an alkenyl having a carbon number of 2 to 18. Compound (c) is a compound having, in one molecule, an alkoxysilyl and an alkenyl having a carbon number of 2 to 18.

14 Claims, 9 Drawing Sheets ved # EPOXY AND ALKOXYSILYL GROUP-CONTAINING SILSESQUIOXANE AND COMPOSITION THEREOF

CROSS-REFERENCE TO RELATED APPLICATION

This application is a 371 application of the international PCT application serial no. PCT/JP2013/075051, filed on Sep. 17, 2013, which claims priority benefits of Japan Patent Application no. 2012-204512, filed on Sep. 18, 2012, and Japan Patent Application no. 2013-090624, filed on Apr. 23, 2013. The entirety of each of the above-mentioned patent applications is hereby incorporated by reference herein and made a part of this specification.

TECHNICAL FIELD

This invention relates to a curable resin composition useful for application to a coating agent, an optical material, and an electronic material, etc., and relates to a cured product obtained by curing the curable resin composition.

BACKGROUND ART

In recent years, light-emitting diodes (LED) are rapidly spreading. Light-emitting devices such as LED in widespread use for a large display such as TV and PC, a touch panel, an information terminal such as cellular phone and smartphone, and an illumination system, etc. are making progress toward higher luminance. To keep pace with this progress, a high performance is required also of an encapsulant used for these devices.

So far, a method of using a novolak-type epoxy resin, an alicyclic epoxy resin or an acrylic resin as an encapsulant and curing the resin with an acid anhydride or a polymerization initiator to resin-encapsulate LED, etc. has been attempted (see, for example, Patent Documents 1 and 2). Among others, epoxy resin has an excellent ability to protect a metal component or a device from external environment and therefore has been widely used as an encapsulant for an electronic material.

However, due to exposure to heat from a light-emitting element or an ultraviolet ray, many epoxy resins are involved in the progress of deterioration and cannot maintain high transparency, resulting in coloration. Accordingly, in the field requiring high transparency, such as LED, utilization of an epoxy resin is avoided.

A dimethylsiloxane-based silicone-type resin or random siloxane-based curable resin composition is used as an encapsulant having high transparency (see, for example, Patent Documents 3 and 4). Such a curable resin composition is cured by condensation of silanol groups with each other or by hydrosilylation reaction of a carbon-carbon double bond with an SiH group, using a platinum catalyst.

These curable resin compositions containing siloxane as a main component can maintain high transparency over a long period of time even when exposed to heat or light and therefore are widely used as an encapsulant for LED, etc. However, further improvements are required of the curable resin composition, because, for example, the adherence to a base material is poor, the refractive index of the resin is lower than the value required by an encapsulant, or there is a problem in satisfying both tack property on the cured product surface and crack resistance during curing.

In addition, the silicone-based encapsulation resin is poor in the sulfur gas resistance and water vapor barrier property and therefore suffers from a problem that a metal component is discolored to decrease the luminance due to permeation of a corrosive gas through the encapsulation resin. To solve this problem, for example, an attempt is made to improve the permeability of sulfuric gas or water vapor by increasing the crosslinking density of a silicone resin or a siloxane resin (see, for example, Patent Documents 5 and 6). On the other hand, a silicone resin is grafted to a silica fine particle with an attempt to achieve higher gas barrier property than that of conventional silicone resins (for example, Patent Document 7).

However, their performance is not sufficient in terms of gas barrier property, as compared with conventional epoxy resins. Furthermore, it has been discovered that when a dimethyl silicone-based resin is exposed to heat for a long period of time, the resin is gradually decomposed to reduce the thickness and the gas barrier property and mechanical properties are deteriorated with aging. An attempt is made to improve thermophysical properties and mechanical properties by introducing a tough framework into the side chain of a silicone resin, but this technique is not completely complementary to maintaining physical properties for a long period time, because after all, the dimethyl silicone moiety is deteriorated and a corrosive gas permeates the moiety.

Under these circumstances, an encapsulation resin having both high gas barrier performance and mechanical properties comparable to an epoxy resin while maintaining high transparency comparable to a silicone resin is demanded.

CITATION LIST

Patent Literatures

Patent Document 1: JP S61-112334 A
Patent Document 2: JP H02-289611 A
Patent Document 3: JP 2003-273292 A
Patent Document 4: JP 2006-299099 A
Patent Document 5: JP 2012-251058 A
Patent Document 6: JP 2010-265410 A
Patent Document 7: JP 2012-251166 A

SUMMARY OF INVENTION

Technical Problem

To meet the demand above, it is required that the heat resistance, heat yellowing resistance, light resistance, transparency and refractive index are high, the adherence to a base material is excellent, the heat cycle resistance, mechanical properties and high gas barrier performance are ensured, and these physical properties are maintained even when exposed to high temperature over a long period of time, but a curable resin composition having a balance between all of these various characteristic features is not yet present. Therefore, a curable resin composition well-balanced between these characteristic features is demanded.

An object of this invention is to provide a curable resin composition satisfying or improving at least one characteristic feature out of characteristic features such as that the heat resistance, heat yellowing resistance, light resistance, transparency and refractive index are high, and that the adherence to base material, heat cycle resistance, mechanical properties, gas barrier property and durability after long-term high-temperature test are excellent; and a cured product thereof.

Solution to Problem

The present inventors have made intensive studies to solve the problem above. As a result, it has been found that the above-described object can be attained by using a curable resin composition having the following configurations. This invention has been accomplished based on this finding.

That is, this invention has the following configurations.

1. A silicon compound obtained by a hydrosilylation reaction of the following compound (a), compound (b) and compound (c), wherein compound (a) is a silsesquioxane derivative having two or more SiH in one molecule, compound (b) is a compound having, in one molecule, epoxy and/or oxetanyl and an alkenyl having a carbon number of 2 to 18, and compound (c) is a compound having, in one molecule, an alkoxysilyl and an alkenyl having a carbon number of 2 to 18.

2. The silicon compound as described in the above item 1, wherein compound (a) is at least one compound selected from the group consisting of compounds represented by the following formulae (a-1) to (a-5), compound (b) is at least one compound selected from the group consisting of compounds represented by formulae (b-1) to (b-5), and compound (c) is a compound represented by formula (c-1).

In formulae (a-1) to (a-5), each R is a group independently selected from an alkyl having a carbon number of 1 to 45, a cycloalkyl having a carbon number of 4 to 8, an aryl having a carbon number of 6 to 14, and an arylalkyl having a carbon number of 7 to 24; in the alkyl having a carbon number of 1 to 45, at least one hydrogen may be replaced by fluorine, and at least one non-adjacent —$CH_2$— may be replaced by —O— or —CH=CH—; in a benzene ring of the aryl and arylalkyl, at least one hydrogen may be replaced by a halogen or an alkyl having a carbon number of 1 to 10, and in this alkyl having a carbon number of 1 to 10, at least one hydrogen may be replaced by fluorine and at least one non-adjacent —$CH_2$— may be replaced by —O— or —CH=CH—; the carbon number of the alkylene in the arylalkyl is from 1 to 10, wherein at least one non-adjacent —$CH_2$— may be replaced by —O—;

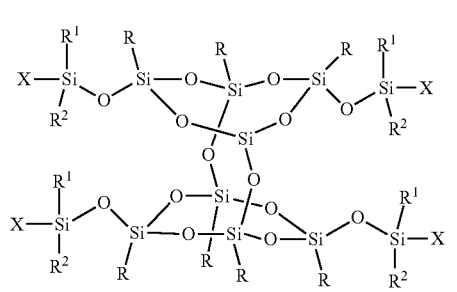
(a-1)

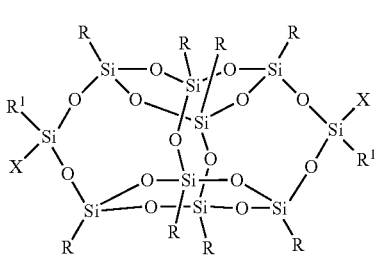
(a-2)

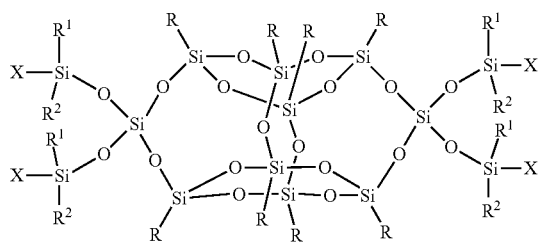
(a-3)

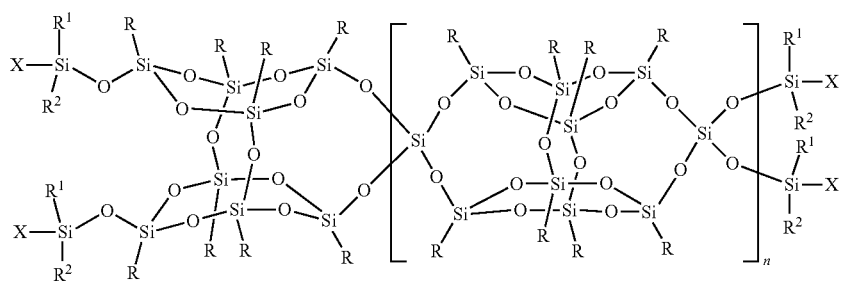
(a-4)

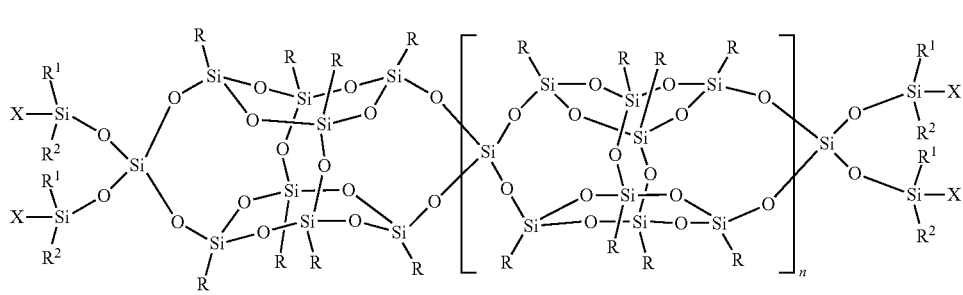
(a-5)

each R¹ is a group independently selected from an alkyl having a carbon number of 1 to 4, cyclopentyl, cyclohexyl and phenyl; and at least two X in one molecule of each compound are hydrogen, with the remaining being a group independently selected from an alkyl having a carbon number of 1 to 4, cyclopentyl, cyclohexyl and phenyl.

In formulae (a-1) and (a-3) to (a-5),

R² is a group independently selected from an alkyl having a carbon number of 1 to 4, cyclopentyl, cyclohexyl and phenyl.

In formulae (a-4) and (a-5), n is an integer of 1 to 100.

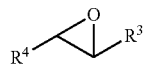
(b-1)

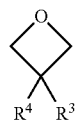
(b-2)

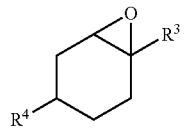
(b-3)

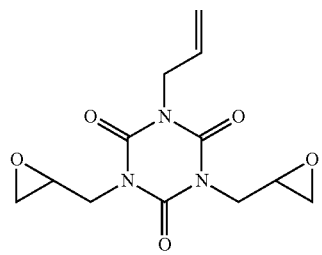
(b-4)

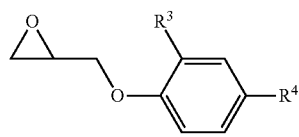
(b-5)

In formulae (b-1) to (b-3) and (b-5), either one of R³ and R⁴ is an alkenyl having a carbon number of 2 to 10, one —CH₂— in this alkenyl may be replaced by —O— or 1,4-phenylene, and the other is hydrogen or an alkyl having a carbon number of 1 to 6.

$$R^5-Si(OR^6)_3 \quad (c-1)$$

In formula (c-1), R⁵ is an alkenyl having a carbon number of 2 to 10, one —CH₂— in this alkenyl may be replaced by —O— or 1,4-phenylene, and R⁶ is an alkyl having a carbon number of 1 to 6 or hydrogen.

3. The silicon compound as described in the above item 1 or 2, wherein compound (a) is a silsesquioxane derivative represented by the following formula (a-1-1).

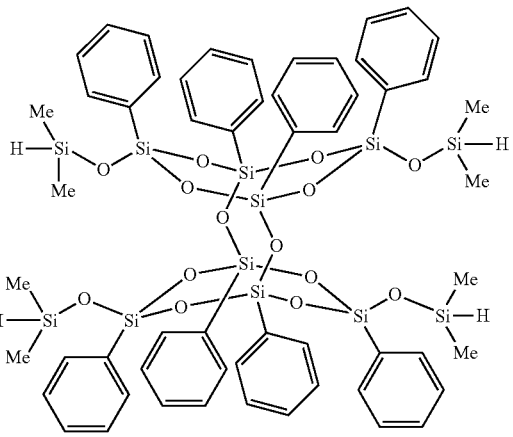
(a-1-1)

In formula (a-1-1), Me represents methyl.

4. The silicon compound as described in any one of the above items 1 to 3, wherein compound (b) is at least one compound selected from the group consisting of compounds represented by the following formulae (b-1-1), (b-2-1) to (b-2-3), (b-3-1), (b-3-2), (b-4-1), (b-5-1) and (b-5-2).

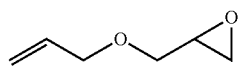
(b-1-1)

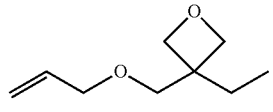
(b-2-1)

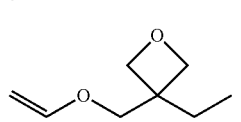
(b-2-2)

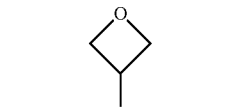
(b-2-3)

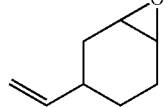
(b-3-1)

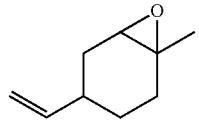
(b-3-2)

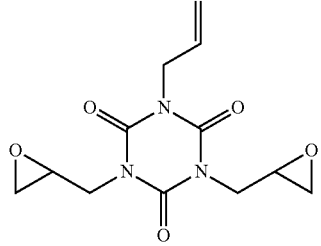
(b-4-1)

-continued

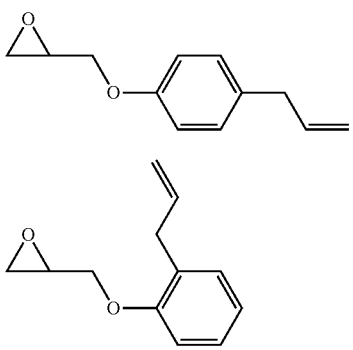

(b-5-1)

(b-5-2)

5. The silicon compound as described in any one of the above items 1 to 4, wherein compound (c) is a compound represented by the following formula (c-1-1).

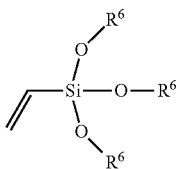

(c-1-1)

In formula (c-1-1), $R^6$ is an alkyl having a carbon number of 1 to 6 or hydrogen.

6. A curable resin composition containing the following (A) to (C):
(A) the silicon compound described in any one of the above items 1 to 5,
(B) an epoxy and/or oxetane resin, and
(C) a curing agent.

7. The curable resin composition as described in the above item 6, wherein the silicon compound of (A) is a silsesquioxane represented by the following formula (α):

9. The curable resin composition as described in any one of the above items 6 to 8, wherein the curing agent of (C) is a photocationic or thermal cationic polymerization initiator, a metal chelate salt or an organic metal.

10. The curable resin composition as described in any one of the above items 6 to 9, further containing a phosphor.

11. The curable resin composition as described in the above item 10, wherein said phosphor is a phosphor for LED.

12. An LED encapsulant containing the curable resin composition described in any one of the above items 6 to 11.

13. A seal material containing the curable resin composition described in any one of the above items 6 to 9.

14. A film-like, sheet-like or coating-like cured product obtained by coating the curable resin composition described in any one of the above items 6 to 9 on a base material and curing the composition by heating or light irradiation.

15. An insulating film containing the cured product described in the above item 14.

Advantageous Effects of Invention

The cured product of the curable resin composition of this invention has a high performance in heat resistance, heat yellowing resistance, light resistance, transparency and refractive index, is excellent in adherence to base material, heat cycle resistance, mechanical properties and gas barrier property, can maintain high gas barrier property and mechanical properties even when exposed to a high temperature over a long period of time, and thus, is useful as an LED encapsulant.

Furthermore, the color conversion material containing the cured product of the curable resin composition of this invention is excellent in the phosphor dispersibility and can stably convert the color of light emitted by an optical semiconductor, over a long period of time without optical unevenness. In addition, the curable resin composition can be, for example, provided as a varnish, etc. in the production of an optical semiconductor element package and further be photo-cured, thus being a resin composition having high handleability.

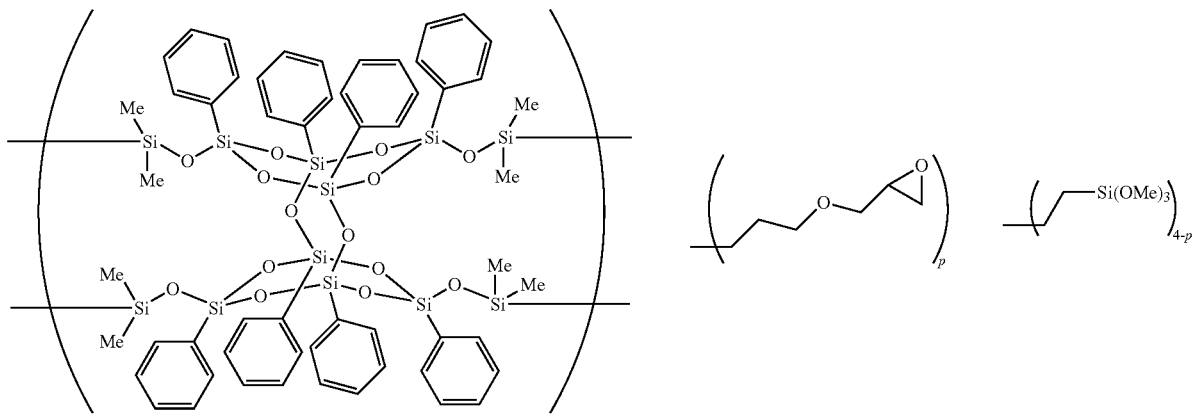

(α)

wherein in formula (α), p is a number satisfying 0<p<4.

8. The curable resin composition as described in the above items 6 or 7, wherein the epoxy and/or oxetane resin of (B) is an epoxy and/or oxetane resin containing no silicon atom in the molecule.

The silicon compound (A) in the curable resin composition of this invention undergoes condensation/crosslinking of the alkoxysilyl group and crosslinking of epoxy, whereby an epoxy resin and a cured product are obtained. In the curable resin composition of this invention, the content of the epoxy groups participating in crosslinking is small, so that a cured product having high transparency can be obtained.

The silicon compound (A) of this invention is excellent in the compatibility with other component, so that a uniformly and densely crosslinked cured product can be obtained from the curable resin composition containing the silicon compound. A cured product excellent in the transparency, curability and gas barrier property can also be obtained by hydrolyzing and condensing the alkoxysilyl group of the silicon compound to form a prepolymer and combining the prepolymer with an epoxy resin to make a composition.

The curable resin composition of this invention has both high transparency and high gas barrier property and satisfies at least one or more characteristic features of low viscosity, adherence, heat cycle resistance, reflow resistance and properties afforded by the mixing with a nanoreinforcement, i.e., low thermal expansion, high elasticity and high glass transition temperature.

DESCRIPTION OF EMBODIMENTS

Figure 1:
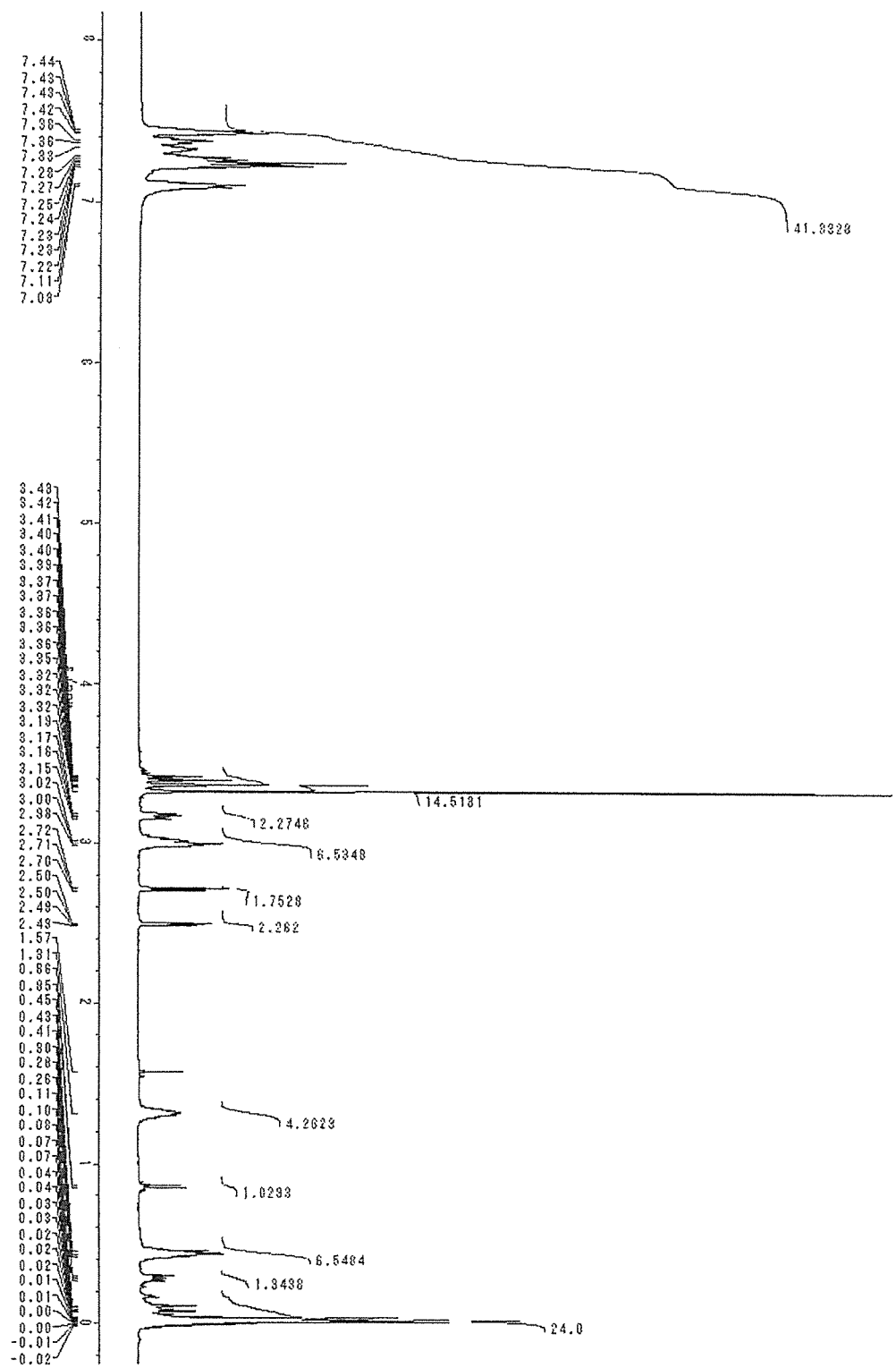
FIG. 1 shows the NMR chart of Synthesis Example 1.

The terms used in this invention are described.

The compound represented by formula (1) is sometimes referred to as compound (1). The compounds represented by other formulae are sometimes simply referred to in the same manner. The silicon compound obtained in this invention is sometimes simply expressed as the silicon compound.

In this invention, the phrase "at least one "A" may be replaced by "B"" means that when the number of "A" is 1, the position of "A" is arbitrary and when the number of "A" is 2 or more, their positions can also be selected without limitation. The phrase "at least one A may be replaced by B, C or D" encompasses a case where arbitrary A is replaced by B, a case where arbitrary A is replaced by C, a case where arbitrary A is replaced by D, and a case where a plurality of A are replaced by at least two of B, C and D. For example, the scope of an alkyl group in which at least one —CH$_2$— may be replaced by —O— or —CH═CH— includes an alkyl, an alkenyl, an alkoxy, an alkoxyalkyl, an alkoxyalkenyl, and an alkenyloxyalkyl.

The configuration where arbitrary —CH$_2$— in an alkyl or an alkylene may be replaced by —O— excludes a case where all of a plurality of consecutive —CH$_2$— are replaced by —O—. In addition, a case where a plurality of oxygen atoms continue, such as —O—O—, is also excluded.

In Examples, the data displayed on an electronic balance is indicated using "g" (gram) that is a mass unit. The mass % or mass ratio is the data based on such a numerical value.

<Curable Resin Composition>

The curable resin composition of this invention, which can be cured by heating or light irradiation, contains (A) a silicon compound obtained by this invention, (B) an epoxy and/or oxetane resin, and (C) a curing agent, and may contain, if desired, a silane coupling agent.

<(A) Silicon Compound Obtained by this Invention>

The silicon compound contained in the curable resin composition of this invention is obtained by a hydrosilylation reaction of the following compound (a), compound (b) and compound (c). Furthermore, a silanol-containing silicon compound can be produced by converting the alkoxysilyl into silanol.

By virtue of having silanol, crosslinking with an alkoxysilyl group or other compounds having silanol swiftly proceeds, and at least one physical property of high water vapor barrier property, high transparency, low thermal expansion, high glass transition temperature, heat cycle resistance and adherence can be acquired.

Compound (a) is a silsesquioxane derivative having two or more Si—H groups in one molecule. The number of SiH groups in compound (a) is 2 or more, preferably 4 or more.

Compound (b) is a compound having, in one molecule, epoxy and/or oxetanyl and an alkenyl having a carbon number of 2 to 18, and preferably has one or more epoxy and/or oxetanyl in one molecule.

Compound (c) is a compound having, in one molecule, an alkoxysilyl and an alkenyl having a carbon number of 2 to 18. Examples of the alkoxysilyl include methoxysilyl, ethoxysilyl, propioxysilyl, and butoxysilyl. The molecular weight of compound (c) is preferably from 100 to 500, more preferably from 100 to 250.

In the silicon compound (A) for use in this invention, the ratio of the constituent units respectively derived from compound (a), compound (b) and compound (c) preferably satisfies, assuming that the molar fractions of the respective compounds are ω, φ and ϕ, respectively, {ω×number of the SiH groups contained in one molecule of compound (a)}≤{φ×number of the alkenyl groups contained in one molecule of compound (b)}+{ϕ×number of the alkenyl groups contained in one molecule of compound (c)}.

The hydrosilylation reaction of compound (a), compound (b) and compound (c) may be performed by simultaneously adding compound (a), compound (b) and compound (c), but is preferably performed by subjecting compound (a) and compound (c) to a hydrosilylation reaction to satisfy "molar number of SiH contained in (a)>molar number of alkenyl contained in (c)" and then adding an excessive amount of compound (b) to cause a hydrosilylation reaction between the unreacted SiH groups and the alkenyl groups of compound (b).

The hydrosilylation reaction is preferably performed in a solvent. The solvent used for the hydrosilylation reaction is not particularly limited as long as it does not inhibit the progress of reaction. Preferred solvents include, for example, hydrocarbon-based solvents such as hexane and heptane, aromatic hydrocarbon-based solvents such as benzene, toluene and xylene, ether-based solvents such as diethyl ether, tetrahydrofuran (THF) and dioxane, halogenated hydrocarbon-based solvents such as methylene chloride and carbon tetrachloride, and ester-based solvents such as ethyl acetate.

One of these solvents may be used alone, or a plurality thereof may be used in combination. Among the above solvents, aromatic hydrocarbon-based solvents are preferred, wherein toluene is most preferred.

The hydrosilylation reaction may be performed at room temperature. Heating may be applied so as to accelerate the polymerization. Cooling may be applied so as to control heat generation from the polymerization, or undesired polymerization, etc. In the hydrosilylation polymerization, a catalyst can be used, if desired.

The polymerization can be facilitated by the addition of a hydrosilylation catalyst. The Karstedt catalyst, Speier catalyst, or hexachloroplatinic acid, etc. may be preferably utilized as the hydrosilylation catalyst.

These hydrosilylation catalysts have high reactivity, and therefore the reaction can be allowed to sufficiently proceed by the addition thereof in a small amount. The amount of the catalyst used is preferably from $10^{-9}$ to 1 mol %, more preferably from $10^{-7}$ to $10^{-3}$ mol %, in terms of the ratio of the transition metal contained in the catalyst to the hydroxyl group.
Examples of the silsesquioxane having two or more SiH groups in one molecule include compounds represented by the following formulae (a-1) to (a-5). Compound (a) is preferably at least one compound selected from the group consisting of compounds represented by the following formulae (a-1) to (a-5).
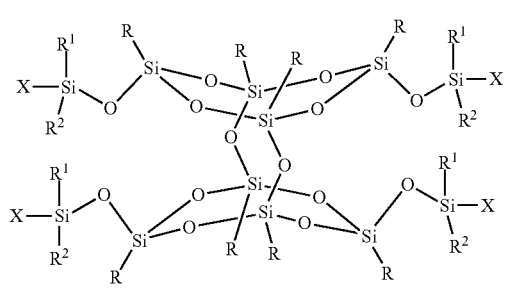
(a-1)
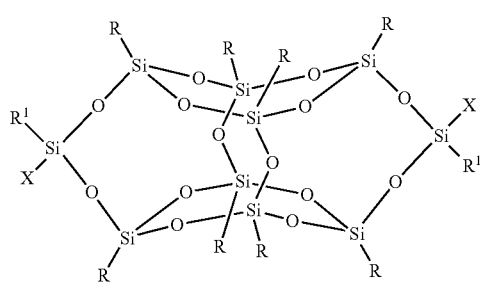
(a-2)
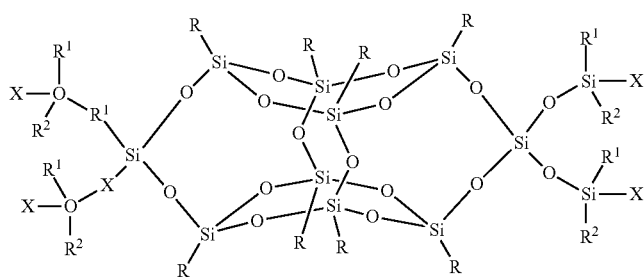
(a-3)
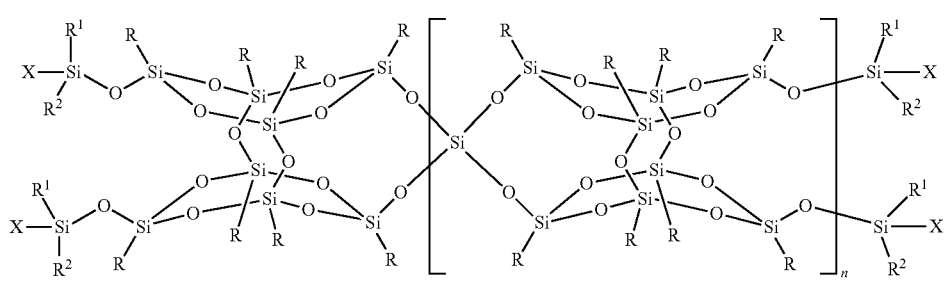
(a-4)
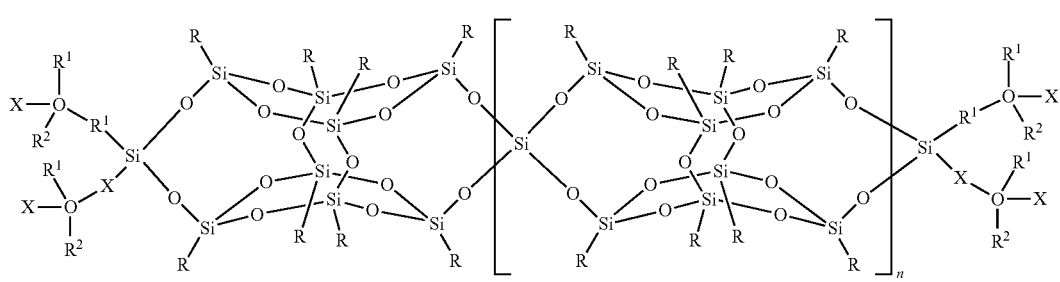
(a-5)

In formulae (a-1) to (a-5), R is a group independently selected from an alkyl having a carbon number of 1 to 45, a cycloalkyl group having a carbon number of 4 to 8, an aryl group having a carbon number of 6 to 14, and an arylalkyl having a carbon number of 7 to 24.

In the alkyl having a carbon number of 1-45, at least one hydrogen may be replaced by fluorine, and at least one non-adjacent —CH$_2$— may be replaced by —O— or —CH=CH—.

In a benzene ring of the aryl having a carbon number of 6 to 14 and the arylalkyl having a carbon number of 7 to 24, at least one hydrogen may be replaced by a halogen or an alkyl having a carbon number of 1 to 10. In this alkyl having a carbon number of 1 to 10, at least one hydrogen may be replaced by fluorine, and at least one non-adjacent —CH$_2$— may be replaced by —O— or —CH=CH—.

The carbon number of the alkylene in the arylalkyl is from 1 to 10, and at least one non-adjacent —CH$_2$— therein may be replaced by —O—.

R is preferably a group independently selected from cyclopentyl, cyclohexyl, phenyl, and an alkyl having a carbon number of 1 to 10. In this alkyl having a carbon number of 1 to 10, at least one hydrogen may be replaced by fluorine, and at least one non-adjacent —CH$_2$— may be replaced by —O—. In the phenyl, at least one hydrogen may be replaced by a halogen such as fluorine or by an alkyl having a carbon number of 1 to 10.

R is more preferably cyclopentyl, cyclohexyl or phenyl in which at least one hydrogen may be replaced by chlorine, fluorine, methyl, methoxy or trifluoromethyl, still more preferably cyclohexyl or phenyl, and most preferably phenyl.

$R^1$ in formulae (a-1) to (a-5) is a group independently selected from an alkyl having a carbon number of 1 to 4, cyclopentyl, cyclohexyl and phenyl. Examples of the alkyl having a carbon number of 1 to 4 include methyl, ethyl, propyl, 2-methylethyl, butyl, and tert-butyl. Preferred examples of $R^1$ or $R^2$ are methyl and phenyl. $R^1$ and $R^2$ are preferably the same group.

$R^2$ in formulae (a-1) and (a-3) to (a-5) is also defined similarly to $R^1$.

In formulae (a-1) to (a-5), at least two X in one molecule of each compound are hydrogen, with the remaining X being a group independently selected from an alkyl having a carbon number of 1 to 4, cyclopentyl, cyclohexyl and phenyl.

In formulae (a-4) and (a-5), n is an integer of 1 to 100.

Compound (a) is more preferably a compound represented by formula (a-1-1) below:

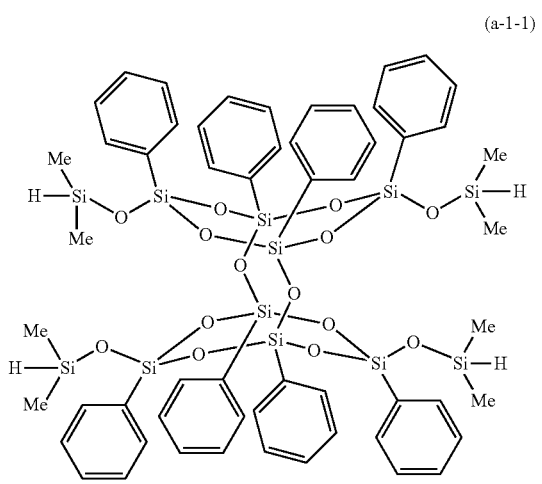 [SMILES: C[SiH](C)O[Si]1(c2ccccc2)O[Si]2(c3ccccc3)O[Si](O[SiH](C)C)(c3ccccc3)O[Si](c3ccccc3)(O1)O[Si]1(c3ccccc3)O[Si](O[SiH](C)C)(c3ccccc3)O[Si](c3ccccc3)(O[Si](O[SiH](C)C)(c3ccccc3)O1)O2]

(a-1-1)

In formula (a-1-1), Me stands for methyl. The compound of formula (a-1-1) can be prepared according to the method described in International Publication No. 2004/024741. In addition, other compounds can also be obtained with known methods.

Examples of compound (b) include compounds represented by formulae (b-1)-(b-5).

(b-1)

(b-2)

(b-3)

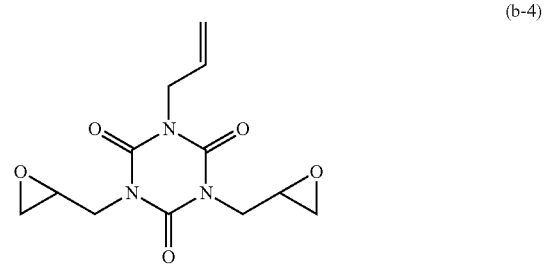

(b-4)

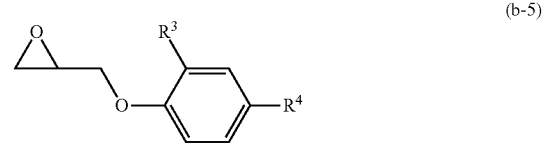

(b-5)

In formulae (b-1) to (b-3) and (b-5), either one of $R^3$ and $R^4$ is an alkenyl having a carbon number of 2 to 10, one —CH$_2$— in this alkenyl may be replaced by —O—, 1,4-phenylene or 1,2-phenylene, and the other is hydrogen or an alkyl having a carbon number of 1 to 6. (b-4) is monoallyl diglycidyl isocyanurate.

Preferred examples of compound (b) include compounds represented by formulae (b-1-1), (b-2-1) to (b-2-3), (b-3-1), (b-3-2), (b-4-1), (b-5-1) and (b-5-2) below.

(b-1-1)

(b-2-1)

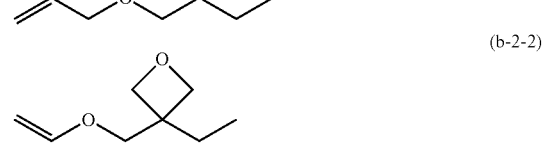

(b-2-2)

(b-2-3)
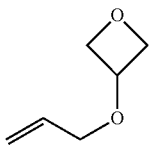

(b-3-1)
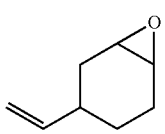

(b-3-2)
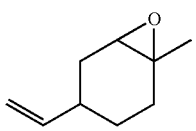

(b-4-1)
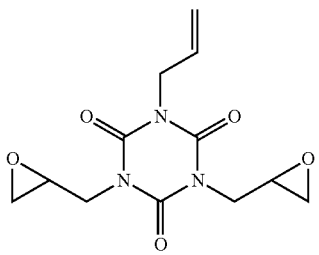

(b-5-1)
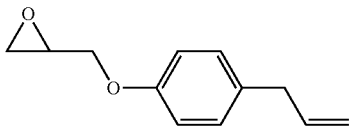

(b-5-2)

Incidentally, allyl glycidyl ether (trade name) sold by Tokyo Chemical Industry Co., Ltd. may be used as the compound represented by formula (b-1-1), Celloxide 2000 (trade name) sold by Daicel Corporation may be used as the compound represented by formula (b-3-1), monoallyl diglycidyl isocyanurate (trade name) sold by Shikoku Chemicals Corporation may be used as the compound represented by formula (b-4-1), and allylphenyl glycidyl ether (trade name) sold by Yokkaichi Chemical Company Limited may be used as the compound represented by formula (b-5-1).

Examples of compound (c) include a compound represented by formula (c-1) below:

$$R^5\text{—Si}(OR^6)_3 \qquad (c\text{-}1).$$

In formula (c-1), $R^5$ is an alkenyl having a carbon number of 2 to 10, one —$CH_2$— in this alkenyl may be replaced by —O— or 1,4-phenylene, and $R^6$ is an alkyl having a carbon number of 1 to 6 or hydrogen.

Compound (c) is preferably a compound represented by formula (c-1-1) below:

(c-1-1)

In formula (c-1-1), $R^6$ is an alkyl having a carbon number of 1 to 6 or hydrogen. Specific examples of the compound of formula (c-1-1) include vinyltrimethoxysilane, vinyltriethoxysilane, vinyltripropoxysilane, and vinyltriisopropoxysilane.

The silicon compound (A) for use in this invention is preferably a silsesquioxane represented by the following formula (α):

(α)
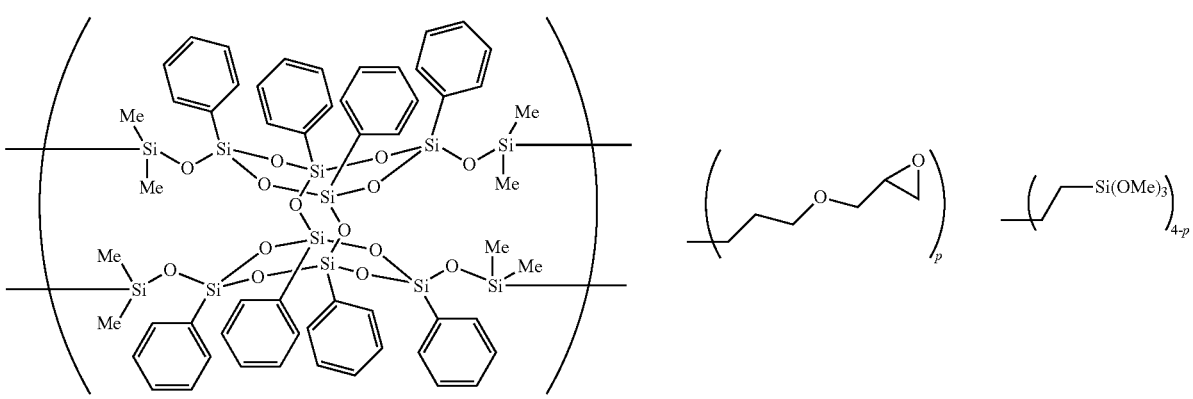

In formula (α), p is a number satisfying 0<p<4 and is preferably 0.1 or more, more preferably 0.5 or more, and preferably 3.9 or less, more preferably 3.5 or less.

Compound (A), which is obtained by a hydrosilylation reaction of compound (a) that is a silsesquioxane having two or more SiH groups in one molecule with compound (c) containing alkoxysilyl and compound (b) having epoxy in one molecule, has epoxy and/or oxetanyl and an alkoxysilyl group, as shown in formula (α).

The content of the silicon compound (A) in the curable resin composition of this invention is preferably from 10 to 90 mass %, more preferably from 20 to 60 mass %, based on the total amount of the curable resin composition. Within this range, the composition exhibits excellent characteristic features in terms of heat resistance, transparency, yellowing resistance, heat yellowing resistance and light resistance.

<(B) Epoxy and/or Oxetane Resin>

The curable resin composition of this invention contains an epoxy and/or oxetane resin. In this invention, the epoxy resin is sometimes referred to as including an oxetane compound or an oxetane resin, which is a 4-membered cyclic ether.

The epoxy and/or oxetane resin is preferably an epoxy and/or oxetane resin containing no silicon atom in the molecule.

Examples of the epoxy and/or oxetane resin containing no silicon atom in the molecule include a compound represented by the following formula (γ) and a hydrogenated bisphenol A-type epoxy resin represented by the following formula (δ).

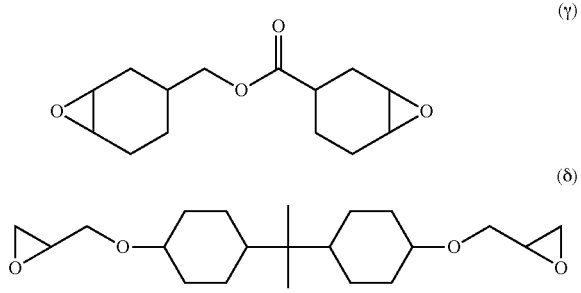

Among these, the epoxy resin represented by formula (γ) is commercially offered, for example, as Celloxide (trade name) 2021P by Daicel Corporation, the epoxy resin represented by formula (δ) is commercially offered, for example, as jER (trade name) YX8000 by Mitsubishi Chemical Corporation, and thus, these resins are easily available.

In addition, specific examples of the 4-membered ring epoxy resin containing no silicon in the molecule include an oxetane resin such as Aron Oxetane (registered trademark) produced by Toagosei Co., Ltd.

In the curable resin composition of this invention, the content of the epoxy and/or oxetane resin (B) is preferably from 0.1 to 80 mass %, more preferably from 1 to 40 mass %, based on the total amount of the curable resin composition. Within this range, the adherence of the cured resin to the substrate can be enhanced or the viscosity of the curable resin composition can be adjusted.

<(C) Curing Agent>

The curing agent may be appropriately selected according to the kind of the silicon compound (A) used and, for example, in the case of using formulae (a-1) to (a-5), the curing agent may be appropriately selected according to the kind of X in these formulae, but usually, a cationic polymerization initiator is preferably used.

Examples of the cationic polymerization initiator include an active energy-ray cationic polymerization initiator (cationic photopolymerization initiator) that generates cationic species or Lewis acid by an active energy ray such as ultraviolet ray, and a thermal cationic polymerization initiator that generates cationic species or Lewis acid by heat.

Examples of the active energy-ray cationic polymerization initiator include a metal fluoroboron complex salt, a boron trifluoride complex compound, a bis(perfluoroalkylsulfonyl)methane metal salt, an aryl diazonium compound, a dicarbonyl chelate of an element in Groups IIIa to Va in the Periodic Table, a thiopyrylium salt, $MF_6$ (an anionic form of Group VIb element in the Periodic Table; M is selected from phosphorus, antimony and arsenic), an arylsulfonium complex salt, an aromatic iodonium complex salt, an aromatic sulfonium complex salt, and a bis[4-(diphenylsulfonio)phenyl]sulfide-bis-hexafluoro metal salt. In addition, a mixed ligand metal salt of an iron compound may also be used.

Examples of the active energy-ray cationic polymerization initiator further include an arylsulfonium complex salt, an aromatic sulfonium or iodonium salt of a halogen-containing complex ion, and an aromatic onium salt of an element in Groups II, Va and VIa in the Periodic Table. Some of these salts are available as a commercial product.

Examples of the thermal cationic polymerization initiator include a cationic catalyst such as triflic acid salt and boron trifluoride, and a protonic acid catalyst, with a triflic acid salt being preferred. Examples of the triflic acid salt include diethylammonium triflate, diisopropylammonium triflate, and ethyldiisopropylammonium triflate.

Meanwhile, some of the aromatic onium salt used as the active energy-ray cationic polymerization initiator generate cationic species by heat, and these can also be used as the thermal cationic polymerization initiator.

Among these cationic polymerization initiators, an aromatic onium salt is preferred in view of an excellent balance between handleability, latency and curability. Among the aromatic onium salts, a diazonium salt, an iodonium salt, a sulfonium salt and a phosphonium salt are preferred in view of an excellent balance between handleability and latency.

As the cationic polymerization initiator, one compound may be used alone, or two or more compounds may be used in combination.

<Curing Agent: Metal Chelate Compound>

A metal chelate compound can be used as the curing agent. With regards to the metal chelate compound, a composite catalyst of an organoaluminum compound and a silanol group-containing organosilicon compound, or a composite catalyst of an organoaluminum compound and an alkoxy group-containing organosilicon compound, can be used.

Examples of the metal chelate salt compound include a composite catalyst of an organoaluminum compound and a silanol group-containing organosilicon compound, a composite catalyst of an organoaluminum compound and an alkoxy group-containing organosilicon compound, and an organotitanium chelate-type compound.

Examples of the organoaluminum compound include an aluminum complex such as trisacetylacetonatoaluminum, trisethylacetonatoaluminum, trissalicylaldehydatoaluminum and tris(o-carbonylphenolato)aluminum, an aluminum metal salt such as aluminum stearate and aluminum benzoate, and an aluminum alkoxide.

Examples of the organoaluminum compound include an aluminum complex such as trisacetylacetonatoaluminum, trisethylacetonatoaluminum, trissalicylaldehydatoaluminum and tris(o-carbonylphenolato)aluminum, an aluminum metal salt such as aluminum stearate and aluminum benzoate, and an aluminum alkoxide.

Examples of the organotitanium chelate compound include diisopropoxy bis(acetylacetonato)titanate, tetra(acetylacetonato)titanate, dioctanoxytitanium dioctanate, and diisopropoxy bis(ethylacetylacetonato)titanate.

As the metal chelate salt compound, one compound may be used alone, or two or more compounds may be used in combination.

Examples of the organometallic compound includes an organotin compound. Examples thereof include dibutyltin diacetate, dibutyltin dioctate, dibutyltin dilaurate, dibutyltin diacetylacetonate, dibutyltin dimaleic acid monobutyl ester, dioctyltin diacetate, dioctyltin maleate, dioctyltin dimaleic acid monooctyl ester, bis(acetoxydibutyltin)oxide, dibutyltin oxyacetate dibutyltin oxyoctylate, and dibutyltin oxylaurate dibutyltin bismethylmaleate.

As the organometallic compound, one compound may be used alone, or two or more compounds may be used in combination.

The content of the curing agent (C) in the curable resin composition of this invention is not particularly limited, but from the standpoint that the curing reaction can sufficiently proceed to obtain a target cured product and reduction in the physical properties of the cured product and coloration of the cured product are not caused, the content is preferably from 0.01 to 10.0 mass %, and more preferably from 0.03 to 3.0 mass %, relative to the total amount of the silicon compound (A) and the epoxy and/or oxetane resin (B) in the curable resin composition. Two or more members of a cation polymerization initiator, a metal chelate compound and an organometallic compound may be used in combination.

<Silane Coupling Agent>

The curable resin composition of this invention preferably further contains a silane coupling agent, in addition to the above components of (A) to (C). By containing a silane coupling agent, the dispersibility of a phosphor can be increased. Examples of the silane coupling agent include a compound represented by the following formula:

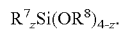

$R^7_z Si(OR^8)_{4-z}$.

In the above formula, $R^7$ is a group having a reactive functional group represented by $FG-R^9—$, FG is epoxy, an amino group, a vinyl group or (meth)acryl, $R^9$ is a linear or cyclic alkylene having a carbon number of 1 to 10 or phenylene, $R^8$ is an alkyl having a carbon number of 1 to 4, and Z is an integer of 0 to 3.

In the curable resin composition of this invention, as the silane coupling agent, 2-(3,4-epoxycyclohexyl)ethyltrimethoxysilane ["Sila-Ace (registered trademark) 5530" produced by JNC Corporation] and 3-glycidoxypropyltrimethoxysilane ["Sila-Ace (registered trademark) S510 produced by JNC Corporation] are particularly preferred in view of transparency and storage stability in the curable resin composition.

The content of the silane coupling agent in the curable resin composition of this invention is preferably from 0 to 40 mass %, and more preferably from 2 to 20 mass %, based on the total amount of the curable resin composition. Within this range, adherence of the curable resin composition to a substrate is enhanced and high transparency is exhibited.

<Nanoreinforcement>

The curable resin composition of this invention may contain a nanoreinforcement, in addition to the above components (A) to (D). Examples thereof include a nano-silica filler.

Examples of the nano-silica filer include wet or dry, fumed or fused silica having an average particle diameter of from 1 nm to less than 1,000 nm, more preferably from 5 to 500 nm and still more preferably from 10 to 50 nm. Examples thereof include Aerosil (registered trademark) 200 (trade name), Aerosil (registered trademark) 300 (trade name), Aerosil (registered trademark) RX300 (trade name), Aerosil (registered trademark) R812 (trade name), Aerosil (registered trademark) R8200 (trade name), Aeroxide (registered trademark) Alu130 (trade name), and Aeroxide (registered trademark) $TiO_2P25$ (trade name), which are produced by Nippon Aerosil Co., Ltd.

The content of the nanoreinforcement in the curable resin composition of this invention is preferably from 1 to 30 mass % based on the total amount of the curable resin composition.

The crosslinking reaction of the nanoreinforcement with the silicon compound of this invention may also be achieved by adding the nanoreinforcement and the silicon compound of this invention in a solvent, and stirring the mixture at a temperature of 80-220° C. for 1-48 hours.

At this time, if a dispersion state on nanolevel is not obtained due to aggregation, etc. of the nanofiller, an operation of processing a solution containing the nanoreinforcement and the silicon compound of this invention in Star Burst (trade name) made by Sugino Machine Limited is repeated tens of times, whereby a dispersion state on nanolevel can be obtained.

Depending on the case, a crosslinking reaction of the nanoreinforcement with the silicon compound of this invention may be further promoted under heating and refluxing conditions. The crosslinked product of the nanoreinforcement with the silicon compound of this invention can be obtained by separating the solvent from the particle by centrifugation and drying the particle.

<Phosphor>

The curable resin composition of this invention may contain a phosphor, in addition to the components (A) to (C). The phosphor is preferably an inorganic particle used as a phosphor for light-emitting diode (LED), more preferably a phosphor for white LED.

Examples of the phosphor include $(Y,Gd)_3(Al,Ga)_5O_{12}$: $Ce^{3+}$ and $(Ba,Sr,Ca)_2SiO_4:Eu^{2+}$ which are called YAG and widely utilized, and $CaAlSiN_3:Eu^{2+}$ that is a nitride phosphor.

The content of the phosphor in the curable resin composition of this invention is deeply related to the transmittance and color of light transmitted through a color conversion material, and is therefore preferably from 5 to 50 mass % based on the total amount of the curable resin composition.

When the content of the phosphor in the curable resin composition is 50 mass % or less, the transmittance is kept from decreasing to reduce the brightness, and when the content is 5 mass % or more, the color of light transmitted does not change.

<Surface Treatment of Phosphor>

The phosphor for use in the curable resin composition of this invention is preferably surface-treated with the above-described silane coupling agent to improve the dispersibility, transparency, weather resistance, and moisture resistance, etc. Each of those silane coupling agents may be used alone, or two or more thereof may be used in arbitrary combination and ratio.

The amount of the silane coupling agent used on the phosphor surface is not particularly limited as long as the effect of the resin cured product of this invention is not seriously impaired, but the amount used is preferably from 0.1 to 5 mass % relative to the mass of the phosphor.

When the amount of the silane coupling agent used is 0.1 mass % or more relative to the mass of the phosphor, sufficient surface coating is achieved, making it possible to improve the dispersibility, transparency, weather resistance and moisture resistance. When the amount used is 5 mass % or less, the light emission characteristics of the phosphor are not impaired.

<Organic Solvent>

The curable resin composition of this invention may further contain an organic solvent. Examples of the organic solvent include hydrocarbon-based solvents such as hexane and heptane, aromatic hydrocarbon-based solvents such as benzene, toluene and xylene, ether-based solvents such as diethyl ether, tetrahydrofuran (THF) and dioxane, halogenated hydrocarbon-based solvents such as methylene chloride and carbon tetrachloride, ester-based solvents such as ethyl acetate, and ketone-based solvents such as acetone and 2-butanone. Each of these solvents may be used alone, or a plurality thereof may be used in combination.

The content of the organic solvent in the curable resin composition of this invention is preferably from 0 to 30 mass %, and more preferably from 1 to 20 mass %, based on the total amount of the curable resin composition. Within this range, the viscosity of the curable solvent composition can be decreased.

<Stabilizer; Antioxidant>

An antioxidant may be added to the curable resin composition of this invention. By the addition of an antioxidant, oxidation deterioration during heating can be prevented to yield a cured product that is less colored. Examples of the antioxidant include phenol-based, sulfur-based and phosphorus-based antioxidants.

The blending proportion of the antioxidant in the curable resin composition of this invention is preferably from 0.0001 to 0.1 in terms of mass ratio based on the total amount of the curable resin composition.

Examples of the antioxidant include monophenols, bisphenols, polymer-type phenols, a sulfur-based antioxidant, phosphites, and oxaphosphaphenanthrene oxides.

Examples of the monophenols include 2,6-di-tert-butyl-p-cresol, butylated hydroxyanisole, 2,6-di-tert-butyl-p-ethylphenol, and stearyl-β-(3,5-di-tert-butyl-4-hydroxyphenyl)propionate.

Examples of the bisphenols include 2,2'-methylenebis(4-methyl-6-tert-butylphenol), 2,2'-methylenebis(4-ethyl-6-tert-butylphenol), 4,4'-thiobis(3-methyl-6-tert-butylphenol), 4,4'-butylidenebis(3-methyl-6-tert-butylphenol), and 3,9-bis[1,1-dimethyl-2-{β-(3-tert-butyl-4-hydroxy-5-methylphenyl)propionyloxy}ethyl]2,4,8,10-tetraoxaspiro[5,5]undecane.

Examples of the polymer-type phenols include 1,1,3-tris(2-methyl-4-hydroxy-5-tert-butylphenyl)butane, 1,3,5-trimethyl-2,4,6-tris(3,5-di-tert-butyl-4-hydroxybenzyl)benzene, tetrakis-[methylene-3-(3',5'-di-tert-butyl-4'-hydroxyphenyl)propionate]methane, bis[3,3'-bis(4'-hydroxy-3'-tert-butylphenyl)butyric acid]glycol ester, 1,3,5-tris(3',5'-di-tert-butyl-4'-hydroxybenzyl)-S-triazine-2,4,6-(1H,3H,5H)-trione, and tocophenol.

Examples of the sulfur-based antioxidant include dilauryl-3,3'-thiodipropionate, dimyristyl-3,3'-thiodipropionate, and distearyl-3,3'-thiodipropionate.

Examples of the phosphites include triphenyl phosphite, diphenyl isodecyl phosphite, phenyl diisodecyl phosphite, tris(nonylphenyl)phosphite, diisodecyl pentaerythritol phosphite, tris(2,4-di-tert-butylphenyl)phosphite, cyclic neopentanetetraylbis(octadecyl)phosphite, cyclic neopentanetetraylbis(2,4-di-tert-butylphenyl)phosphite, cyclic neopentanetetraylbis(2,4-di-tert-butyl-4-methylphenyl)phosphite, and bis[2-tert-butyl-6-methyl-4-{2-(octadecyloxycarbonyl)ethyl}phenyl]hydrogen phosphite.

Examples of the oxaphosphaphenanthrene oxides include 9,10-dihydro-9-oxa-10-phosphaphenanthrene-10-oxide, 10-(3,5-di-tert-butyl-4-hydroxybenzyl)-9,10-dihydro-9-oxa-10-phosphaphenanthrene-10-oxide, and 10-decyloxy-9,10-dihydro-9-oxa-10-phosphaphenanthrene-10-oxide.

Each of these antioxidants may be used alone, but it is particularly preferable to use phenol-based/sulfur-based antioxidants or phenol-based/phosphorus-based antioxidants in combination.

As for the commercially available phenol-based antioxidant, each of "Irganox 1010 (trade name)" and "Irgafos 168 (trade name)," both being produced by BASF Japan Ltd., may be used alone, and these may also be used in mixture.

<Stabilizer; Ultraviolet Absorber>

In the curable resin composition of this invention, an ultraviolet absorber may be blended so as to enhance the light resistance. As the ultraviolet absorber, an ultraviolet absorber for general plastics can be used. The blending ratio in the curable resin composition of this invention is preferably 0.0001 to 0.1 in terms of mass ratio based on the total amount of the curable resin composition.

Examples of the ultraviolet absorber include salicylic acids, benzophenones, benzotriazoles, and hindered amines.

Examples of the salicylic acids include phenyl salicylate, p-tert-butylphenyl salicylate, and p-octylphenyl salicylate.

Examples of the benzophenones include 2,4-dihydroxybenzophenone, 2-hydroxy-4-methoxybenzophenone, 2-hydroxy-4-octoxybenzophenone, 2-hydroxy-4-dodecyloxybenzophenone, 2,2'-dihydroxy-4-methoxybenzophenone, 2,2'-dihydroxy-4,4'-dimethoxybenzophenone, and 2-hydroxy-4-methoxy-5-sulfobenzophenone.

Examples of the benzotriazoles include 2-(2'-hydroxy-5'-methylphenyl)benzotriazole, 2-(2'-hydroxy-5'-tert-butylphenyl)benzotriazole, 2-(2'-hydroxy-3',5'-di-tert-butylphenyl)benzotriazole, 2-(2'-hydroxy-3'-tert-butyl-5'-methylphenyl)-5-chlorobenzotriazole, 2-(2'-hydroxy-3',5'-di-tert-butylphenyl)-5-chlorobenzotriazole, 2-(2'-hydroxy-3',5'-di-tert-amylphenyl)benzotriazole, and 2-{(2'-hydroxy-3',3",4",5",6"-tetrahydrophthalimidomethyl)-5'-methylphenyl}benzotriazole.

Examples of the hindered amines include bis(2,2,6,6-tetramethyl-4-piperidyl)sebacate, bis(1,2,2,6,6-pentamethyl-4-piperidyl)sebacate, and bis(1,2,2,6,6-pentamethyl-4-piperidyl) [{3,5-bis(1,1-dimethylethyl-4-hydroxyphenyl}methyl]butylmalonate.

<Production of Cured Product>

The cured product obtained by curing the curable resin composition of this invention can be produced, for example, by the following method.

The following liquid (I) and liquid (II) are prepared.

Liquid (I) is prepared by mixing the silicon compound (A) obtained by this invention, an arbitrary amount of the epoxy and/or oxetane resin (B), a surface-treated phosphor, an arbitrary amount of a silane coupling agent, and a stabilizer.

Liquid (II) is prepared by mixing the curing agent (C), an arbitrary amount of the epoxy and/or oxetane resin (B), an arbitrary amount of a silane coupling agent, and if desired, the above-described organic solvent.

Liquid (I) and liquid (II) prepared respectively are mixed by stirring and then defoamed by reducing the pressure. The resulting mixture is coated on a support base material such as film or poured into a mold. In the case of adding a thermal cationic polymerization initiator as a curing agent, the mixture can be heated at 125° C. for 1 hour and finally heated at 150° C. for 2 to 5 hours to be cured. In the case of adding a photocationic curing agent, the mixture can be exposed to an ultraviolet ray (i-line) of 100 to 2,000 mJ/cm² to be cured.

In the curable resin composition of this invention, additives such as curing accelerator, antioxidant and ultraviolet absorber may be mixed.

With respect to the transparency of a cured product obtained by curing the curable resin composition of this invention, the transmittance of the cured product before and after a heat resistance testing is measured by a UV-visible spectrophotometer, and the transparency is evaluated by the yellowness index (YI value) and the percentage retention of light transmittance, which are calculated according to JIS K7363 (1999). At this time, the yellowness index (YI value) at 150° C. and the percentage retention of light transmittance are preferably 20 or less and 70% or more, respectively. When each value falls in the range above, the cured product is shown to be colorless and highly transparent, and such a cured product can be preferably utilized, among others, in the field requiring transparency, such as optical semiconductor encapsulant.

The curable resin composition of this invention may also be thermally cured or photocured in the shape of a film, a sheet or a coating. The cured product obtained in this way can be used in various applications.

The use applications of the curable resin composition of this invention or the cured product obtained by curing the curable resin composition include, for example, a seal material, an encapsulant, an insulating film, a wavelength conversion film, an optical lens, and an adhesive. Among these, the composition or cured product is suitable in particular for a seal material, an encapsulant, and an insulating film.

The encapsulant and seal material are a material working to protect the interior by blocking intrusion of external substances. The encapsulant is a material working, for example, to fill a hole or prevent intrusion of a foreign material from the external, and specific examples include an optical semiconductor (LED) encapsulant and a semiconductor encapsulant. The seal material includes, for example, a material as an adhesive for laminating films or layers together. The insulating film includes, for example, an interlayer insulating film in a laminate substrate, and a material for the insulation between metal wirings.

In addition, a color conversion material (for example, an optical semiconductor encapsulant and an optical lens) containing the curable resin composition of this invention or the cured product obtained by curing the curable resin composition can be used for an optical semiconductor element.

The coating of this invention is obtained by coating the curable resin composition of this invention on a base material.

EXAMPLES

This invention is described in greater detail based on Examples. This invention is not limited to the following Examples.

<Synthesis of Silicon Compound Having Epoxy Group>

Synthesis Example 1

Compound (A1) was produced according to the following formula.

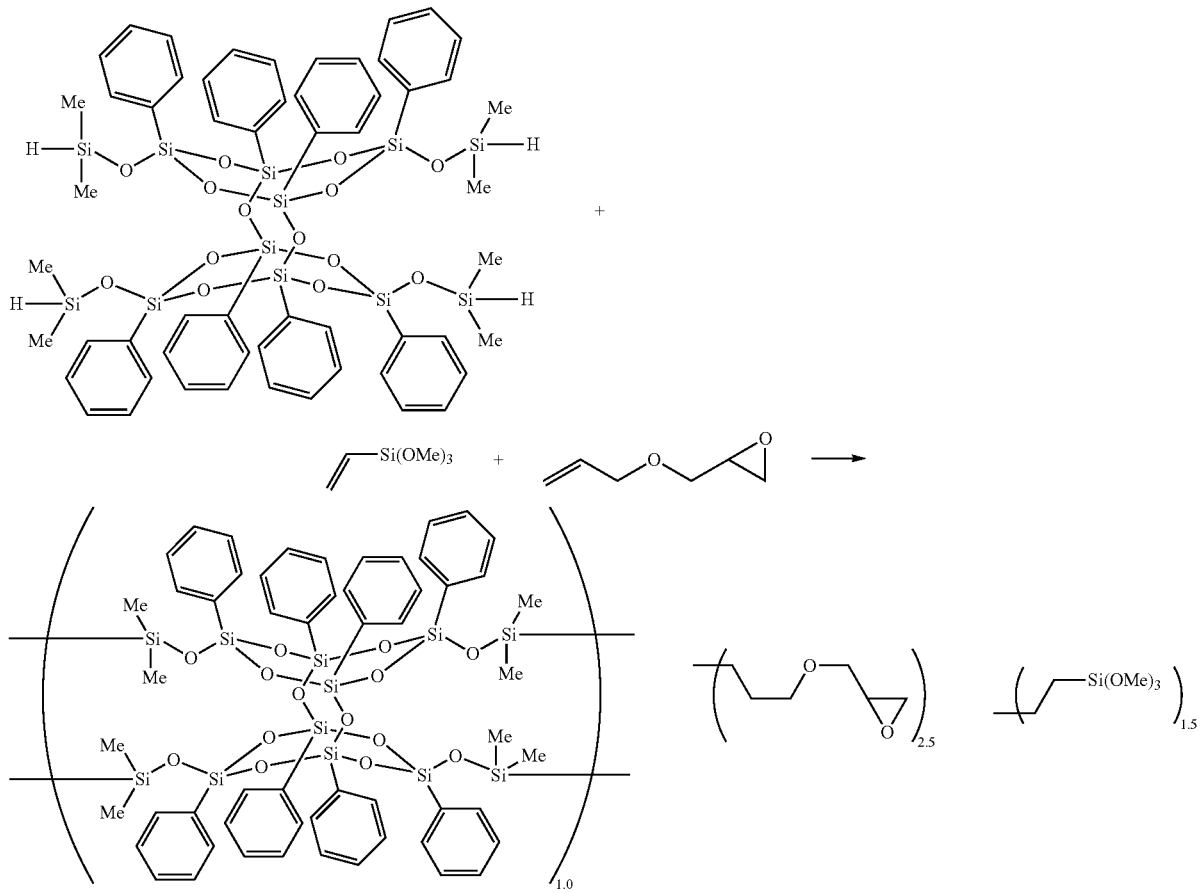

In a nitrogen atmosphere, a reaction vessel equipped with a thermometer, a dropping funnel and a reflux condenser and having an inner volume of 300 mL was charged with compound (a-1-1) (150 g) synthesized by the method disclosed in International Publication No. 2004/024741 and dry toluene (210 g), and sealed with dry nitrogen. The contents were heated under stirring with a magnetic stirrer to a reaction temperature of 100° C.

A Pt catalyst (13 μL) was added using a microsyringe, and allyl glycidyl ether (43 g) produced by Tokyo Chemical Industry Co., Ltd. was slowly added dropwise from the dropping funnel, followed by stirring for 2 hours. Furthermore, a Pt catalyst (92 μL) was added, and Silaplane S210 (trade name) (26 g) produced by JNC Corporation was added, followed by stirring for 2 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 100° C. under vacuum to obtain a colorless transparent viscous liquid (yield: 211 g). The epoxy equivalent of (A1) was measured according to JIS K-7236 (2009) and found to be 730 g/mol. The NMR chart is shown in FIG. 1.

Synthesis Example 2

Compound (A2) was produced according to the following formula.

In a nitrogen atmosphere, a reaction vessel equipped with a thermometer, a dropping funnel and a reflux condenser and having an inner volume of 500 mL was charged with compound (a-1-1) (130 g) synthesized by the method disclosed in International Publication No. 2004/024741 and dry toluene (130 g), and sealed with dry nitrogen. The contents were heated under stirring with a magnetic stirrer to a reaction temperature of 100° C.

A Pt catalyst (100 μL) was added using a microsyringe, and allyl glycidyl ether (11 g) produced by Tokyo Chemical Industry Co., Ltd. was slowly added dropwise from the dropping funnel, followed by stirring for 2 hours. Subsequently, Silaplane 5210 (trade name) (59 g) produced by JNC Corporation was added, followed by stirring for 3 hours. After cooling, activated carbon at 3 mass % was added to the crude product, and the resulting mixture was stirred at room temperature through the night.

Then, filtration was performed, and the filtrate was concentrated in an evaporator. The obtained concentrate was subjected to drying/monomer removal at 100° C. under vacuum to obtain a colorless transparent viscous liquid (yield: 185 g). The epoxy equivalent of (A2) was measured according to JIS K-7236 (2009) and found to be 1,861 g/mol.

Synthesis Example 3

Compound (A3) was produced according to the following formula.

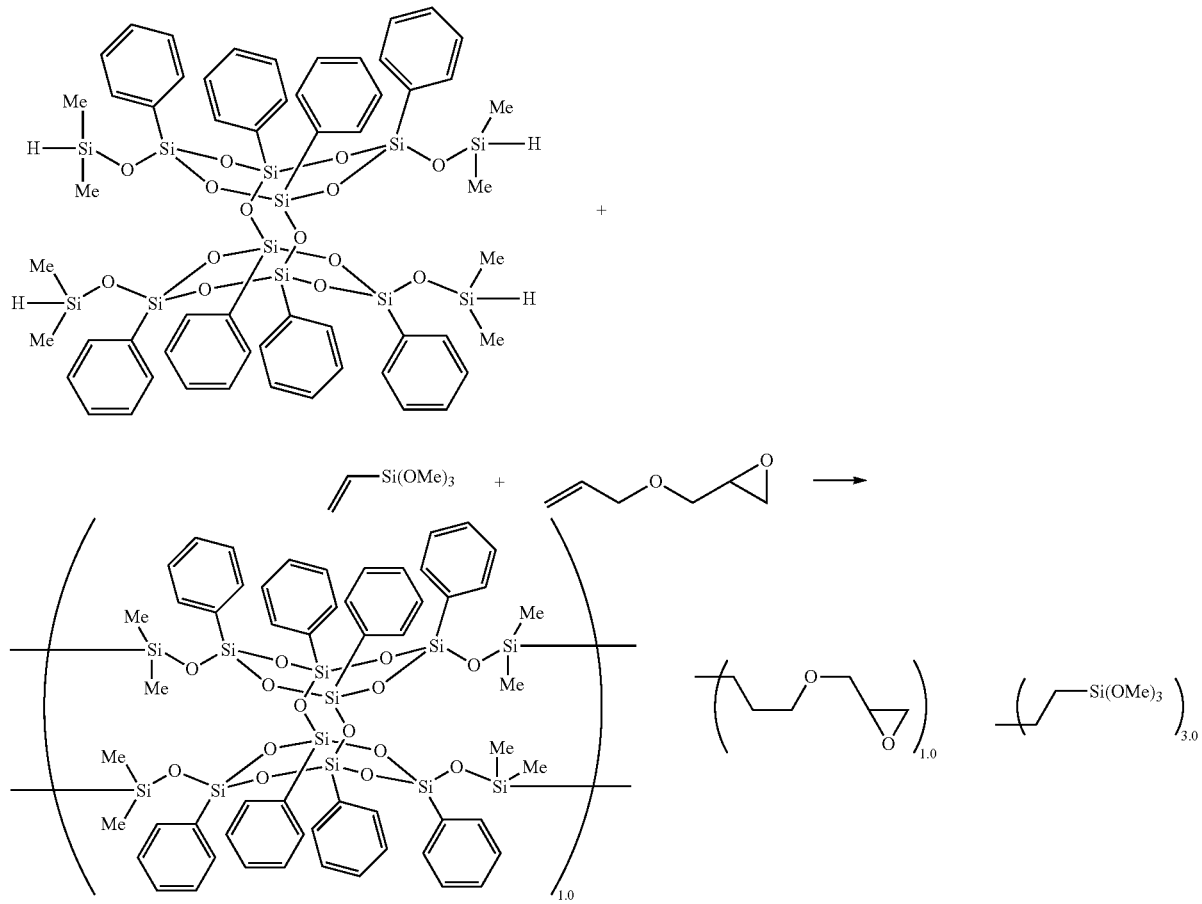

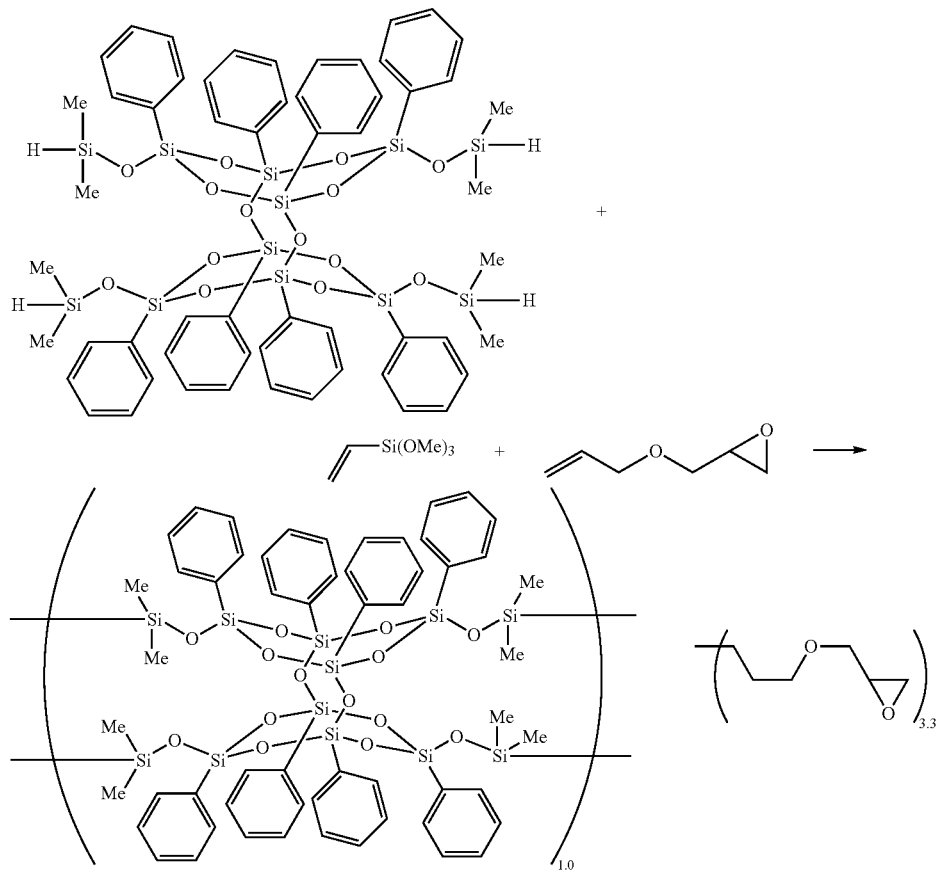

In a nitrogen atmosphere, a reaction vessel equipped with a thermometer, a dropping funnel and a reflux condenser and having an inner volume of 500 mL was charged with compound (a-1-1) (200 g) synthesized by the method disclosed in International Publication No. 2004/024741 and dry toluene (200 g), and sealed with dry nitrogen. The contents were heated under stirring with a magnetic stirrer to a reaction temperature of 100° C.

A Pt catalyst (60 μL) was added using a microsyringe, and allyl glycidyl ether (58 g) produced by Tokyo Chemical Industry Co., Ltd. was slowly added dropwise from the dropping funnel, followed by stirring for 5 hours. Subsequently, Silaplane S210 (trade name) (46 g) produced by JNC Corporation was added, followed by stirring for 3 hours. After cooling, activated carbon at 3 mass % was added to the crude product, and the resulting mixture was stirred at room temperature through the night.

Figure 2:
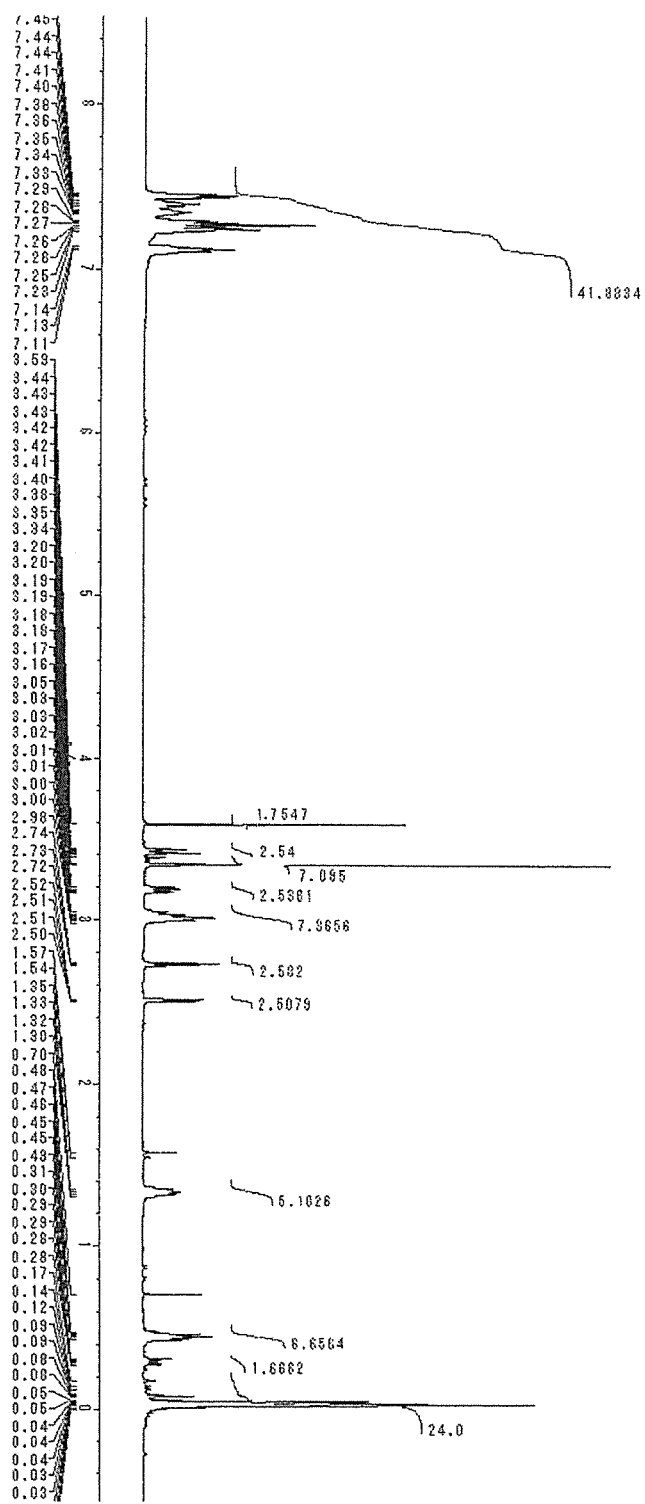
FIG. 2 shows the NMR chart of Synthesis Example 3.

Then, filtration was performed, and the filtrate was concentrated in an evaporator. The obtained concentrate was subjected to drying/monomer removal at 90° C. under vacuum to obtain a colorless transparent viscous liquid (yield: 273 g). The NMR chart is shown in FIG. 2.

Synthesis Example 4

Compound (A4) was produced according to the following formula.

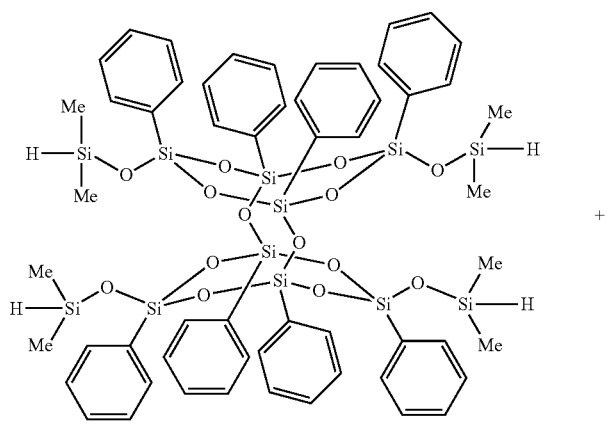

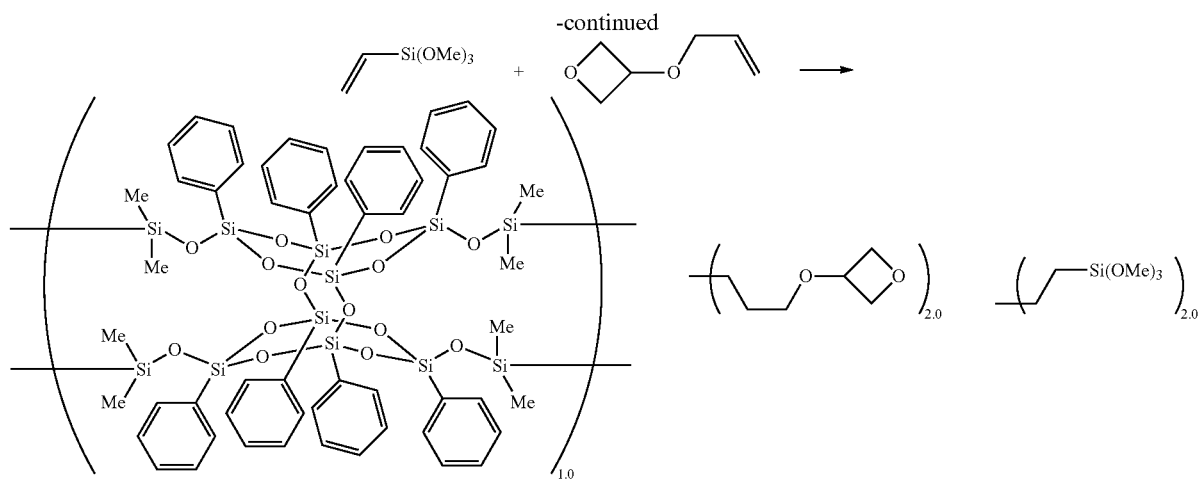

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 μL) was added using a microsyringe, and allyloxyoxetane (17.5 g) produced by Yokkaichi Chemical Company Limited was added dropwise from the dropping funnel, followed by stirring for 1 hour. Furthermore, Silaplane S210 (trade name) (31.9 g) produced by JNC Corporation was added, followed by stirring for 3 hours. After cooling, activated carbon at 3 mass % was added to the crude product, and the resulting mixture was stirred at room temperature through the night.

Figure 3:
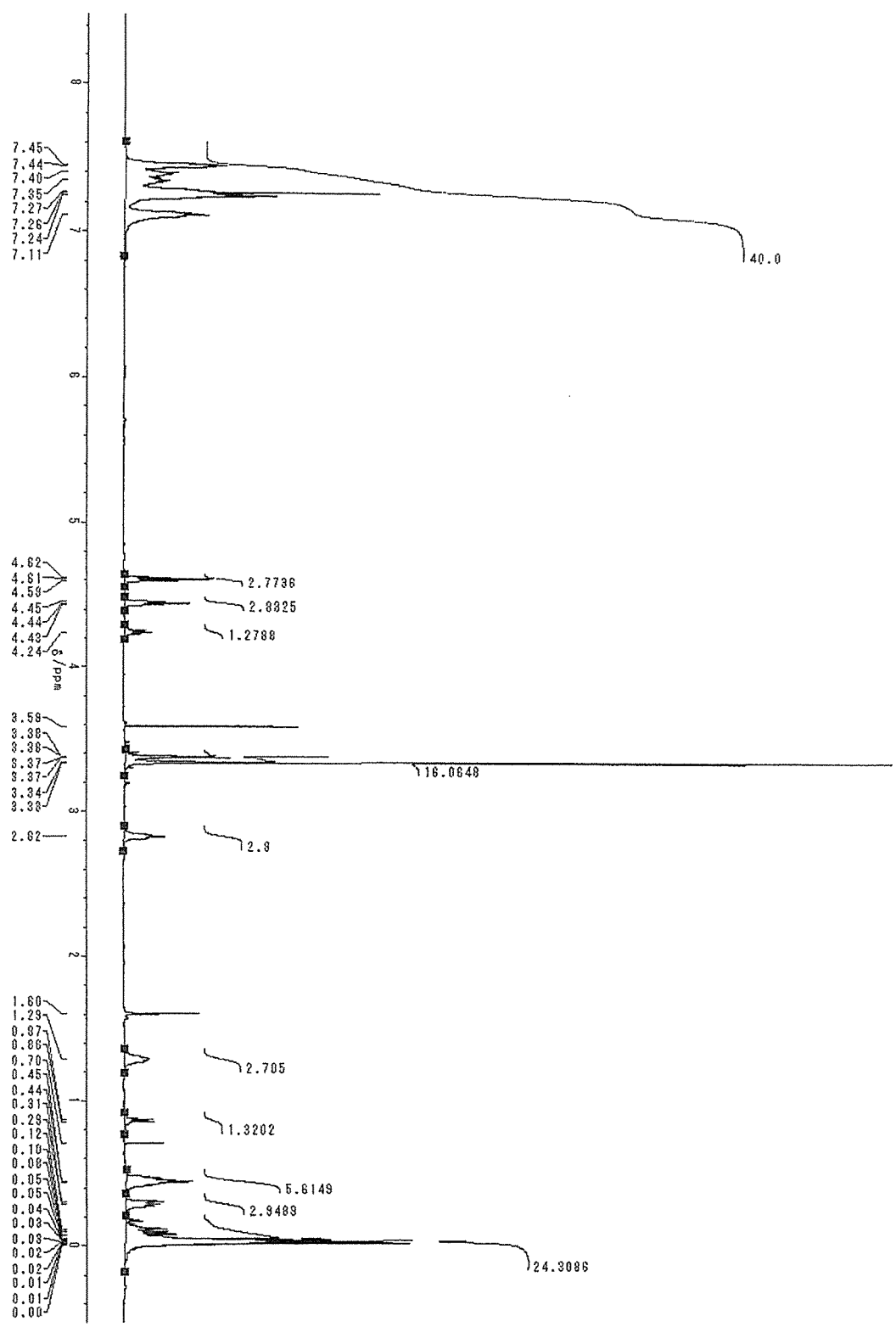
FIG. 3 shows the NMR chart of Synthesis Example 4.

Thereafter, filtration was performed, and the filtrate was concentrated in an evaporator. The obtained concentrate was subjected to drying/monomer removal at 100° C. under vacuum to obtain a colorless transparent viscous liquid (yield: 140 g). The NMR chart is shown in FIG. 3.

Synthesis Example 5

Compound (A5) was produced according to the following formula.

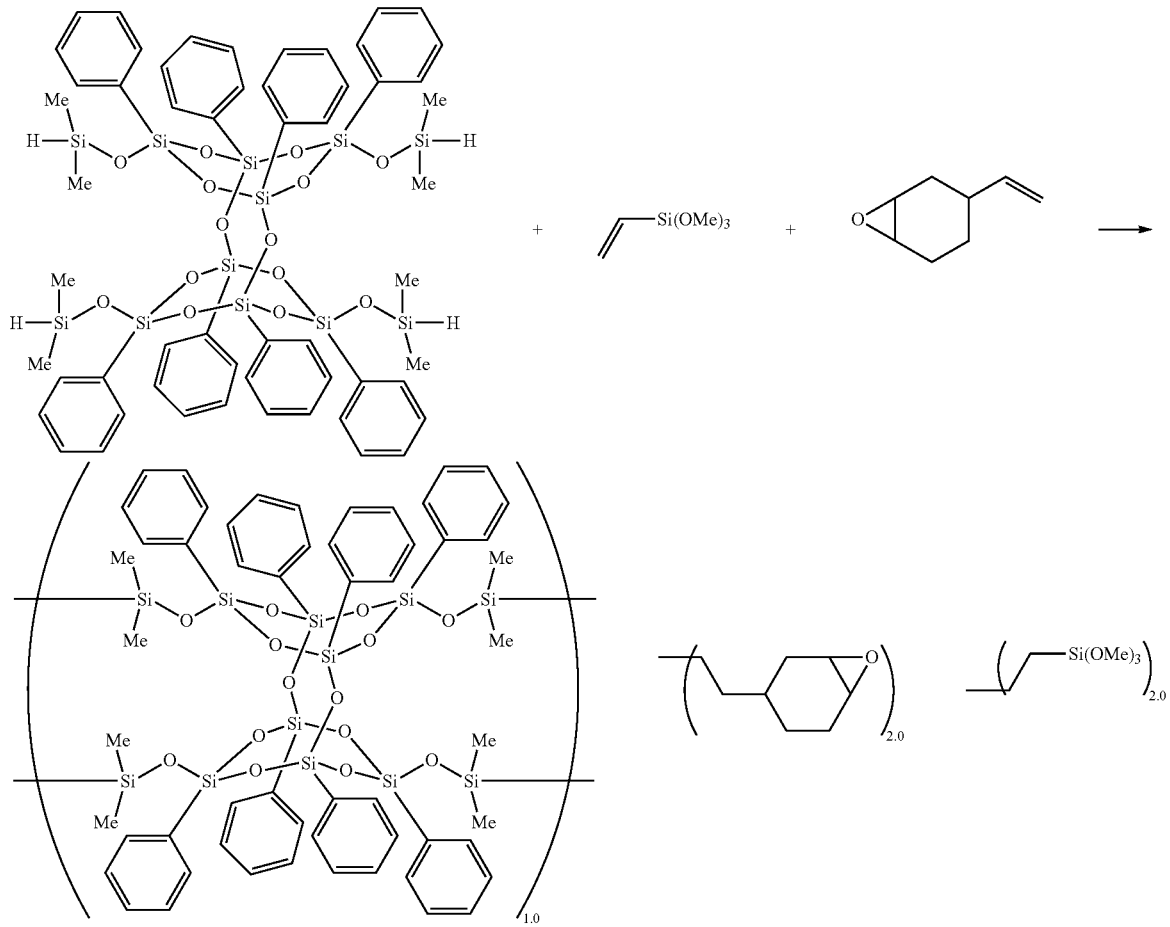

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 μL) was added using a microsyringe, and Celloxide 2000 (19.1 g) produced by Daicel Corporation was added dropwise from the dropping funnel, followed by stirring for 1 hour. Furthermore, Silaplane S210 (trade name) (34.1 g) produced by JNC Corporation was added, followed by stirring for 3 hours. After cooling, activated carbon at 3 mass % was added to the crude product, and the resulting mixture was stirred at room temperature through the night.

Figure 4:
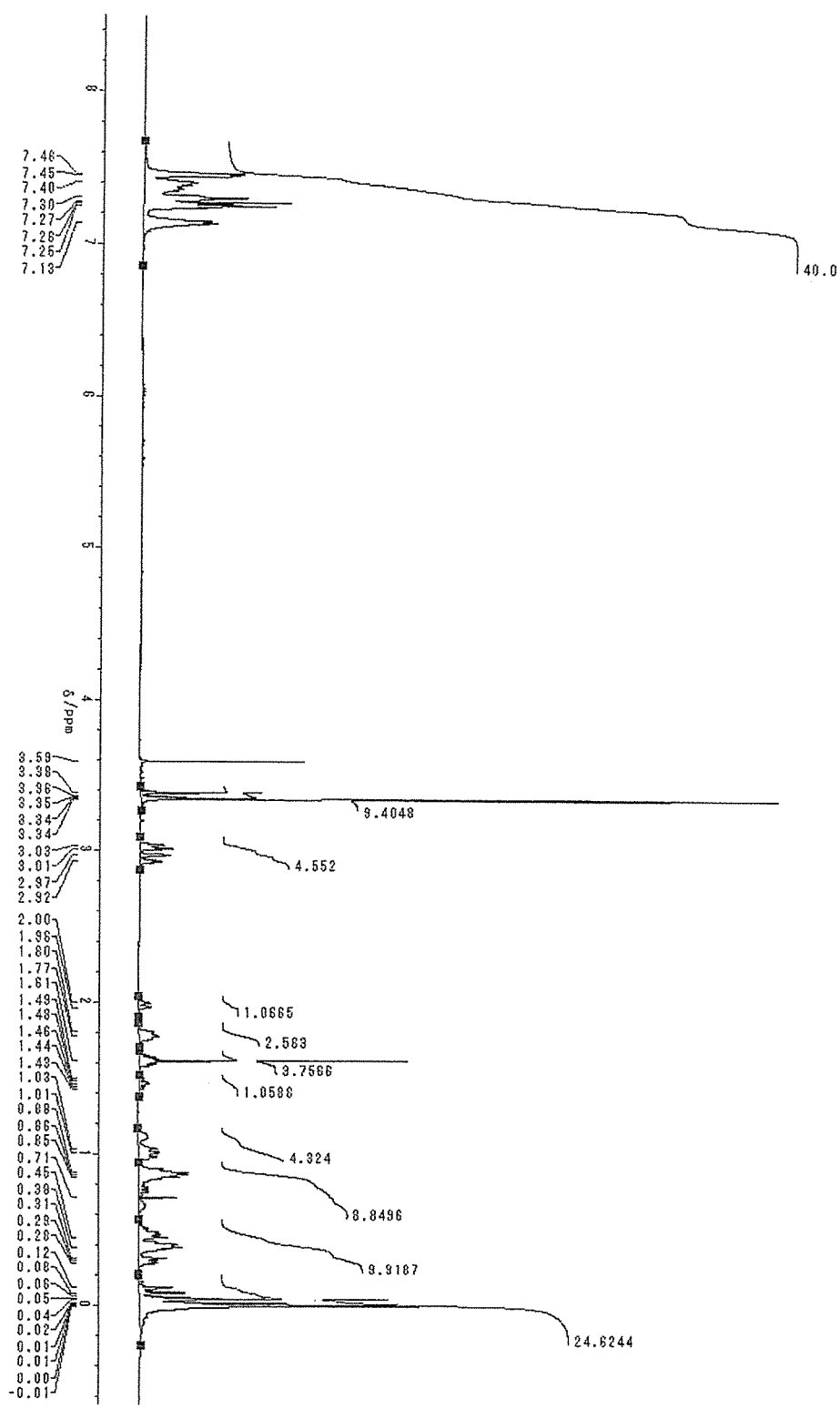
FIG. 4 shows the NMR chart of Synthesis Example 5.

Thereafter, filtration was performed, and the filtrate was concentrated in an evaporator. The obtained concentrate was subjected to drying/monomer removal at 100° C. under vacuum to obtain a colorless transparent viscous liquid (yield: 141 g). The NMR chart is shown in FIG. 4.

Synthesis Example 6

Compound (A6) was produced according to the following formula.

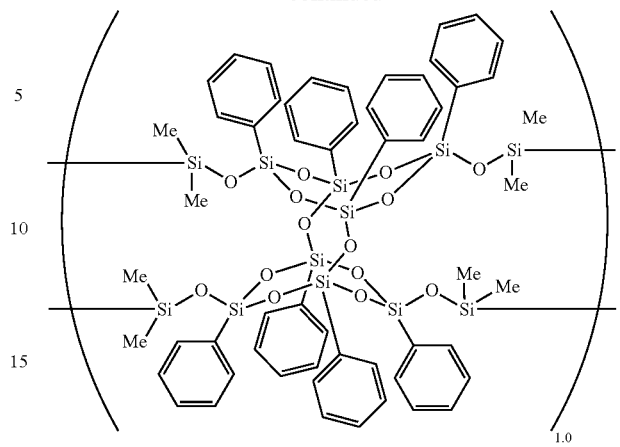

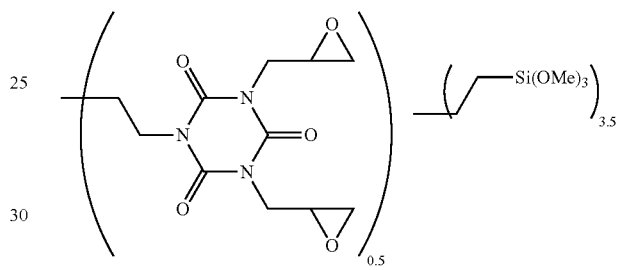

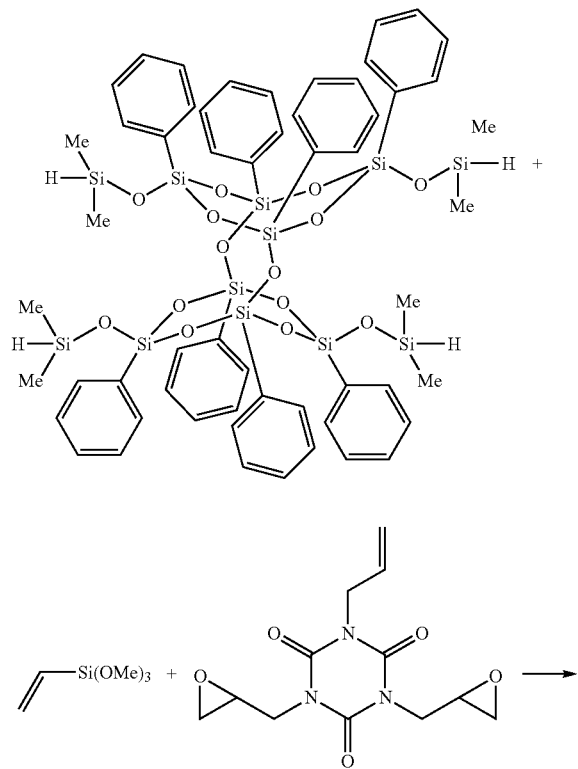

In a nitrogen atmosphere, a reaction vessel equipped with a thermometer, a dropping funnel and a reflux condenser and having an inner volume of 200 mL was charged with compound (a-1-1) (50 g) synthesized by the method disclosed in International Publication No. 2004/024741, dry toluene (50 g) and monoallyl diglycidyl isocyanurate (5.4 g) produced by Shikoku Chemicals Corporation, and sealed with dry nitrogen. The contents were heated under stirring with a magnetic stirrer to a reaction temperature of 100° C.

A Pt catalyst (15 μL) was added using a microsyringe, followed by stirring for 30 min. Subsequently, Silaplane S210 (25.6 g) produced by JNC Corporation was added dropwise, followed by stirring for 3 hours. After cooling, activated carbon at 3 mass % was added to the crude product, and the resulting mixture was stirred at room temperature through the night.

Figure 5:
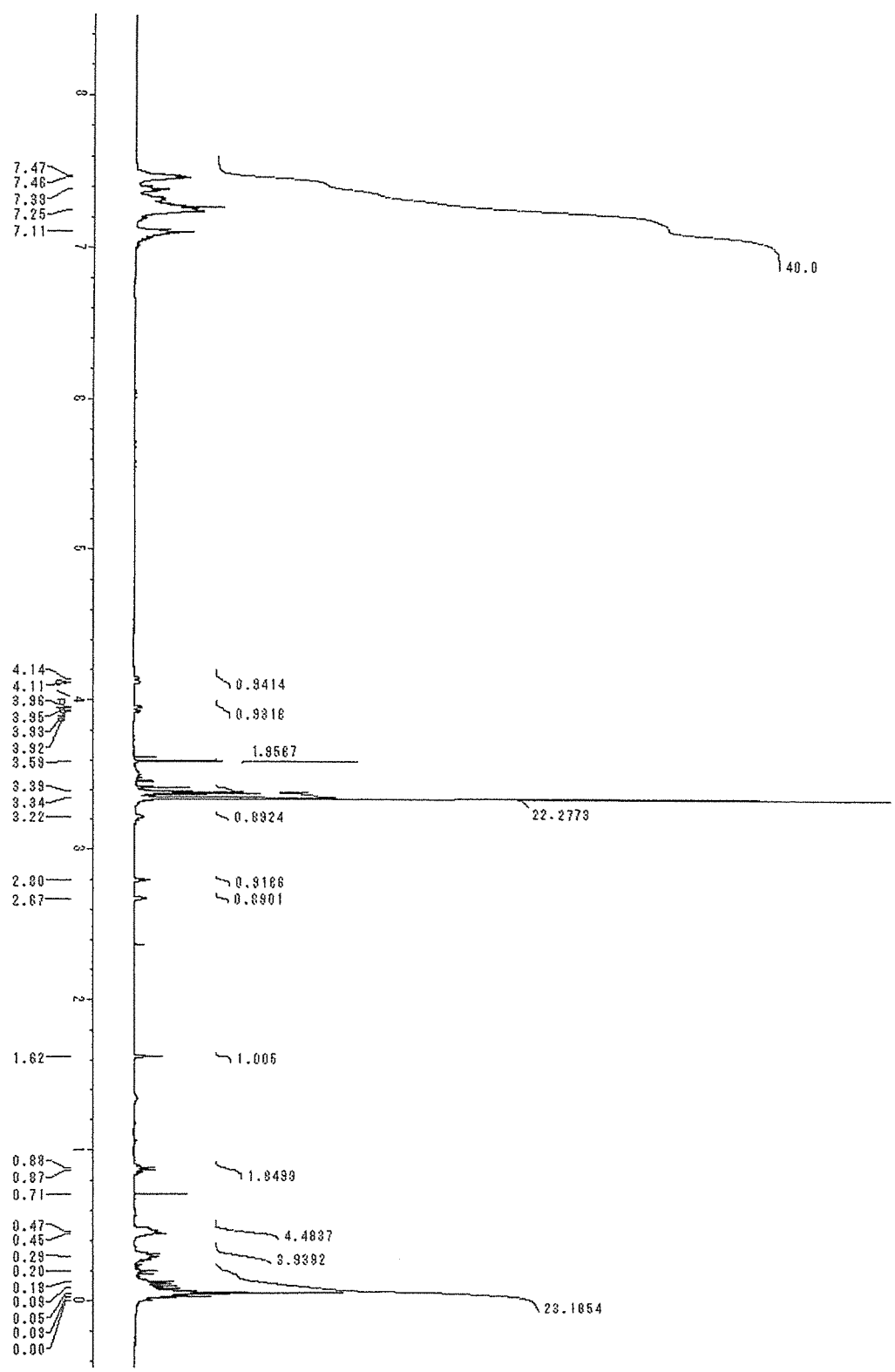
FIG. 5 shows the NMR chart of Synthesis Example 6.

Thereafter, filtration was performed, and the filtrate was concentrated in an evaporator. The obtained concentrate was subjected to drying/monomer removal at 110° C. under vacuum to obtain a colorless transparent viscous liquid (yield: 75 g). The NMR chart is shown in FIG. 5.

Synthesis Example 7

Compound (A7) was produced according to the following formula.

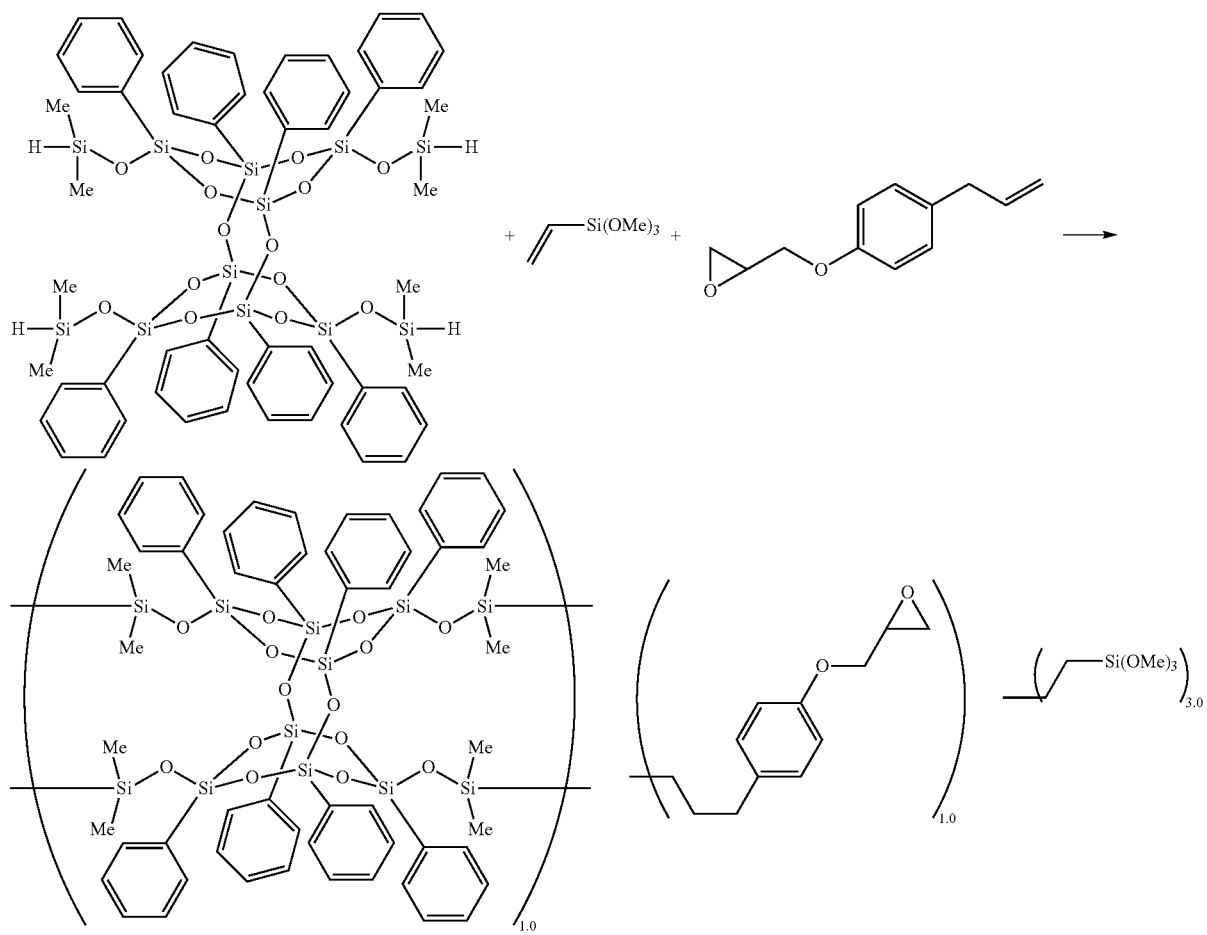

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 μL) was added using a microsyringe, and allylphenyl glycidyl ether (14.6 g) produced by Yokkaichi Chemical Company Limited was slowly added dropwise from the dropping funnel, followed by stirring for 1 hour. Subsequently, Silaplane S210 (45.5 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 110° C. under vacuum to obtain a colorless transparent viscous liquid (yield: 148 g).

Synthesis Example 8

Compound (A8) was produced according to the following formula.

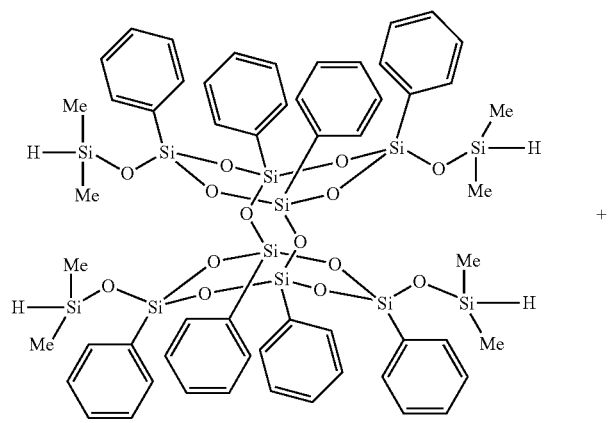

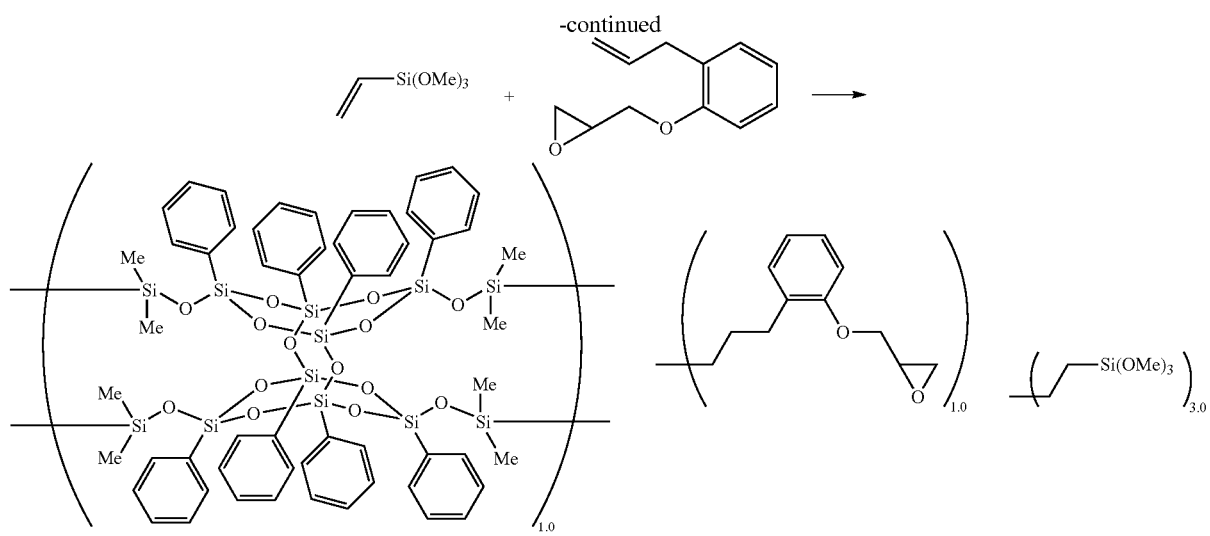

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 μL) was added using a microsyringe, and ortho-allylphenyl glycidyl ether (14.6 g) was slowly added dropwise from the dropping funnel, followed by stirring for 30 minutes. Subsequently, Silaplane S210 (45.5 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 110° C. under vacuum to obtain a colorless transparent viscous liquid (yield: 148 g).

Synthesis Example 9

Compound (A9) was produced according to the following formula.

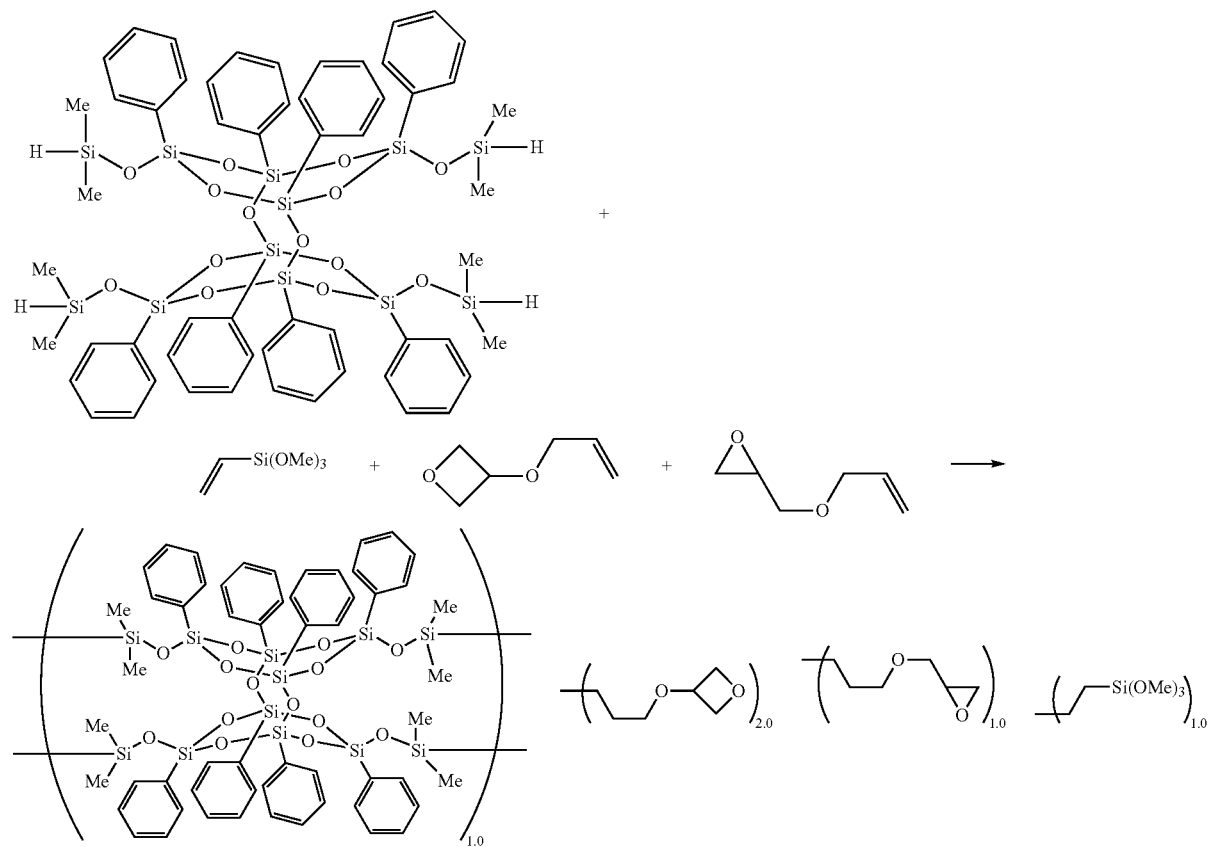

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 μl) was added using a microsyringe, and allyloxyoxetane (17.5 g) produced by Yokkaichi Chemical Company Limited was added dropwise from the dropping funnel, followed by stirring for 1 hour. Subsequently, allyl glycidyl ether (13.2 g) produced by Tokyo Chemical Industry Co., Ltd. was slowly added dropwise, followed by stirring for 1 hour. Further, Silaplane S210 (trade name) (17.1 g) produced by JNC Corporation was added, followed by stirring for 3 hours. After cooling, activated carbon at 3 mass % was added to the crude product, and the resulting mixture was stirred at room temperature through the night.

Figure 6:
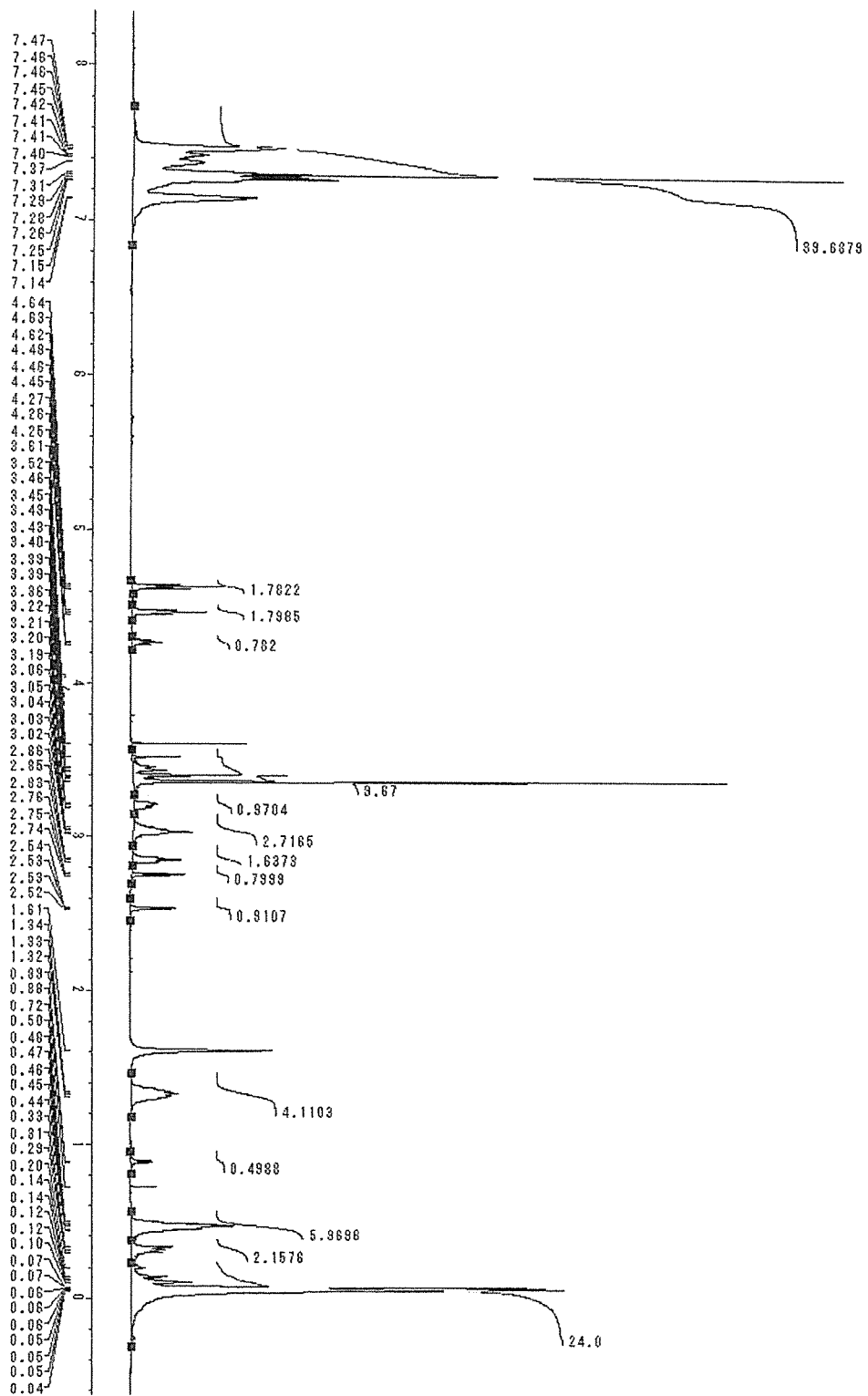
FIG. 6 shows the NMR chart of Synthesis Example 9.

Thereafter, filtration was performed, and the filtrate was concentrated in an evaporator. The obtained concentrate was subjected to drying/monomer removal at 100° C. under vacuum to obtain a colorless transparent viscous liquid (yield: 136 g). The NMR chart is shown in FIG. 6.

Synthesis Example 10

Compound (A10) was produced according to the following formula.

In a nitrogen atmosphere, a reaction vessel equipped with a thermometer, a dropping funnel and a reflux condenser and having an inner volume of 200 mL was charged with compound (a-1-1) (50 g) synthesized by the method disclosed in International Publication No. 2004/024741 and dry toluene (50 g), and sealed with dry nitrogen. The contents were heated under stirring with a magnetic stirrer to a reaction temperature of 100° C.

A Pt catalyst (15 μL) was added using a microsyringe, and monoallyl diglycidyl isocyanurate (3.2 g) produced by Shikoku Chemicals Corporation was slowly added dropwise from the dropping funnel, followed by stirring for 30 minutes. Subsequently, allyl glycidyl ether (2.2 g) produced by Tokyo Chemical Industry Co., Ltd. was slowly added dropwise, followed by stirring for 30 minutes. Furthermore, Silaplane S210 (19.9 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 110° C. under vacuum to obtain a colorless transparent viscous liquid (yield: 73 g).

Synthesis Example 11

Compound (A11) was produced according to the following formula.

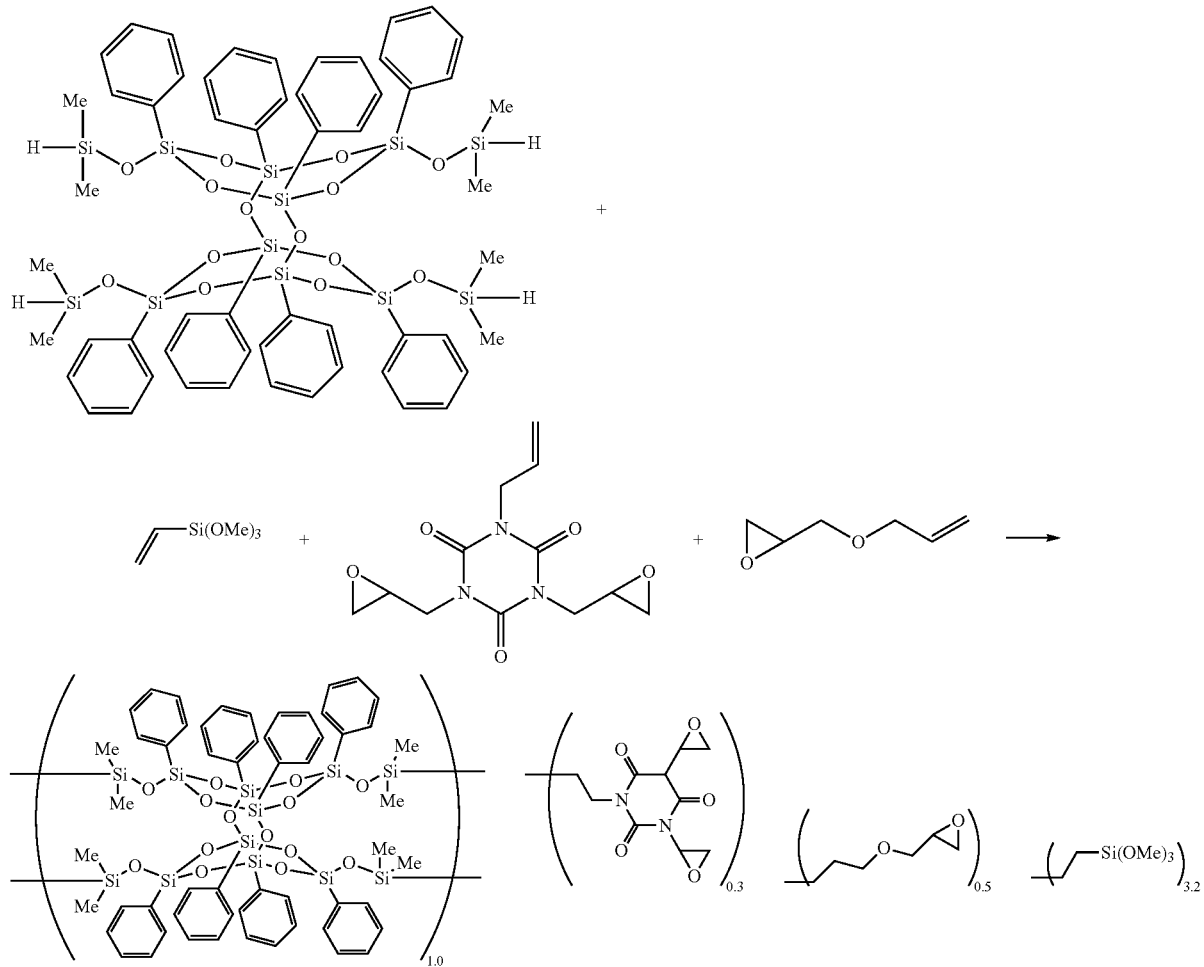

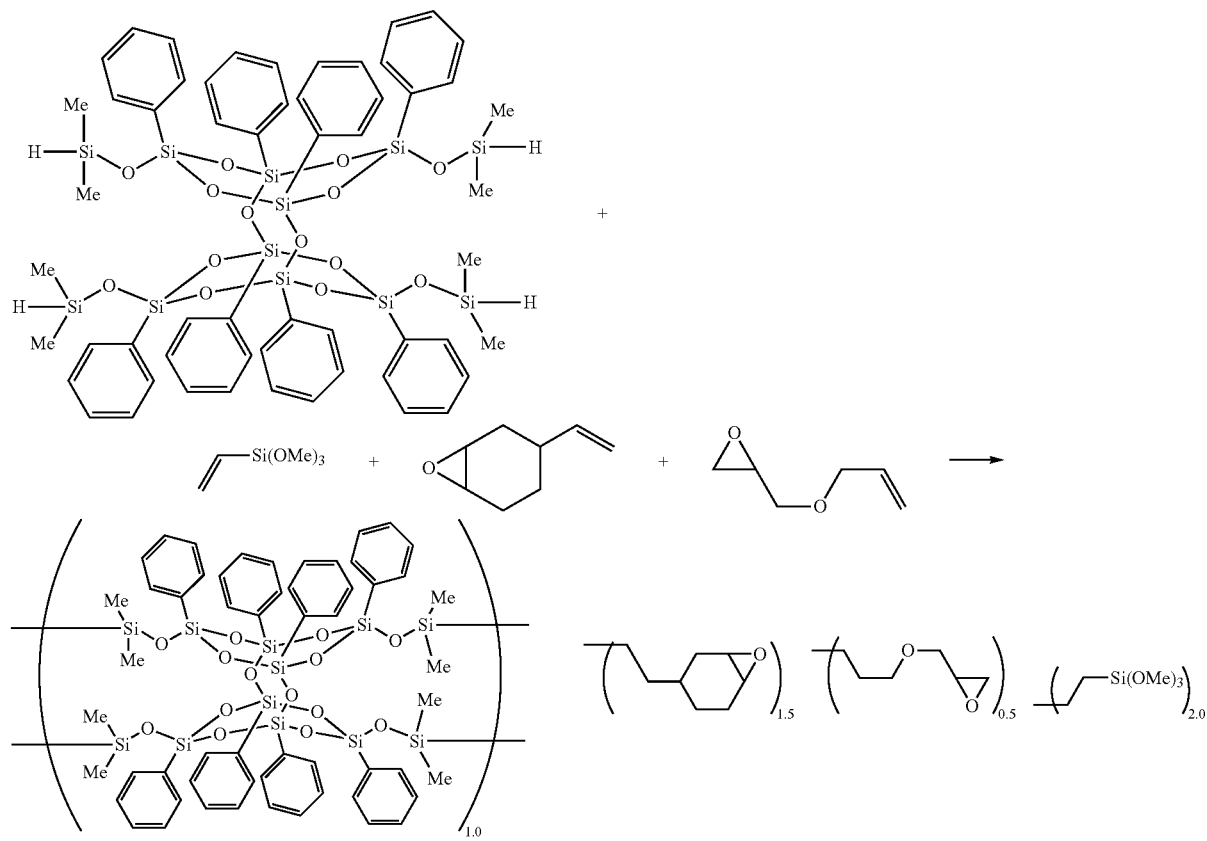

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 μL) was added using a microsyringe, and Celloxide 2000 (14.4 g) produced by Daicel Corporation was slowly added dropwise from the dropping funnel, followed by stirring for 1 hour. Subsequently, allyl glycidyl ether (13.2 g) produced by Tokyo Chemical Industry Co., Ltd. was slowly added dropwise, followed by stirring for 1 hour. Further, Silaplane S210 (22.8 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 100° C. under vacuum to obtain a colorless transparent viscous liquid (yield: 138 g).

Synthesis Example 12

Compound (A12) was produced according to the following formula.

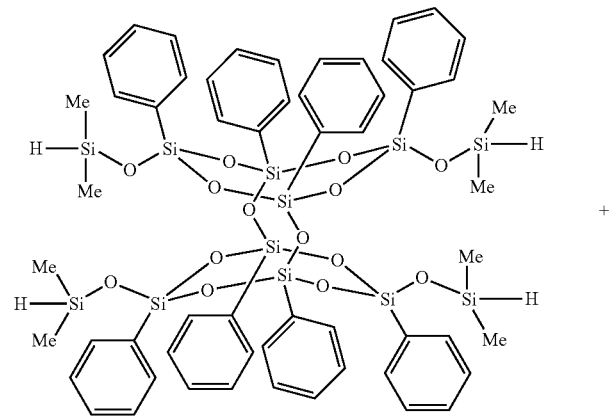

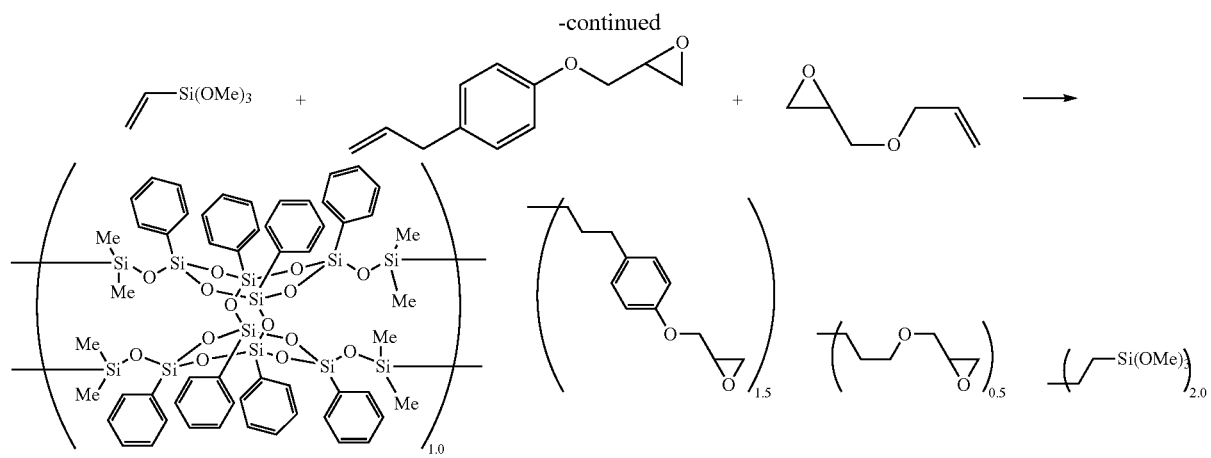

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 μl) was added using a microsyringe, and allylphenyl glycidyl ether (21.9 g) produced by Yokkaichi Chemical Company Limited was slowly added dropwise from the dropping funnel, followed by stirring for 1 hour. Subsequently, allyl glycidyl ether (4.4 g) produced by Tokyo Chemical Industry Co., Ltd. was slowly added dropwise, followed by stirring for 1 hour. Furthermore, Silaplane S210 (34.1 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 110° C. under vacuum to obtain a colorless transparent viscous liquid (yield: 149 g).

Synthesis Example 13

Compound (A13) was produced according to the following formula.

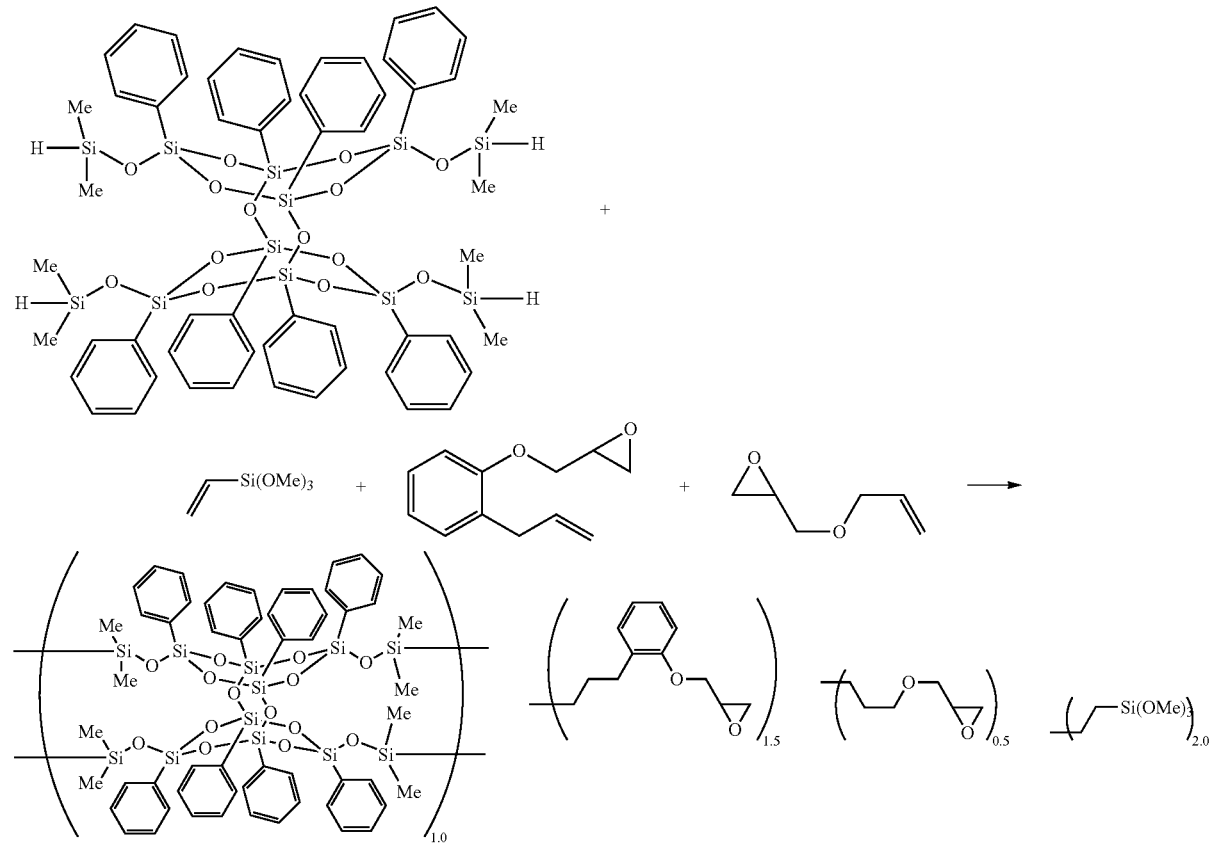

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 µL) was added using a microsyringe, and ortho-allylphenyl glycidyl ether (21.9 g) was slowly added dropwise from the dropping funnel, followed by stirring for 1 hour. Subsequently, allyl glycidyl ether (4.38 g) produced by Tokyo Chemical Industry Co., Ltd. was slowly added dropwise, followed by stirring for 30 minutes. Furthermore, Silaplane S210 (34.1 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 110° C. under vacuum to obtain a colorless transparent viscous liquid (yield: 149 g).

Synthesis Example 14

Compound (A14) was produced according to the following formula.

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741, dry toluene (100 g) and monoallyl diglycidyl isocyanurate (6.5 g) produced by Shikoku Chemicals Corporation, and sealed with dry nitrogen. The contents were heated under stirring with a magnetic stirrer to a reaction temperature of 100° C.

A Pt catalyst (30 µL) was added using a microsyringe, followed by stirring for 30 minutes. Subsequently, allyloxyoxetane (14.9 g) produced by Yokkaichi Chemical Company Limited was slowly added dropwise, followed by stirring for 1 hour. Furthermore, Silaplane S210 (34.1 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 110° C. under vacuum to obtain a colorless transparent viscous liquid (yield: 144 g).

Synthesis Example 15

Compound (A15) was produced according to the following formula.

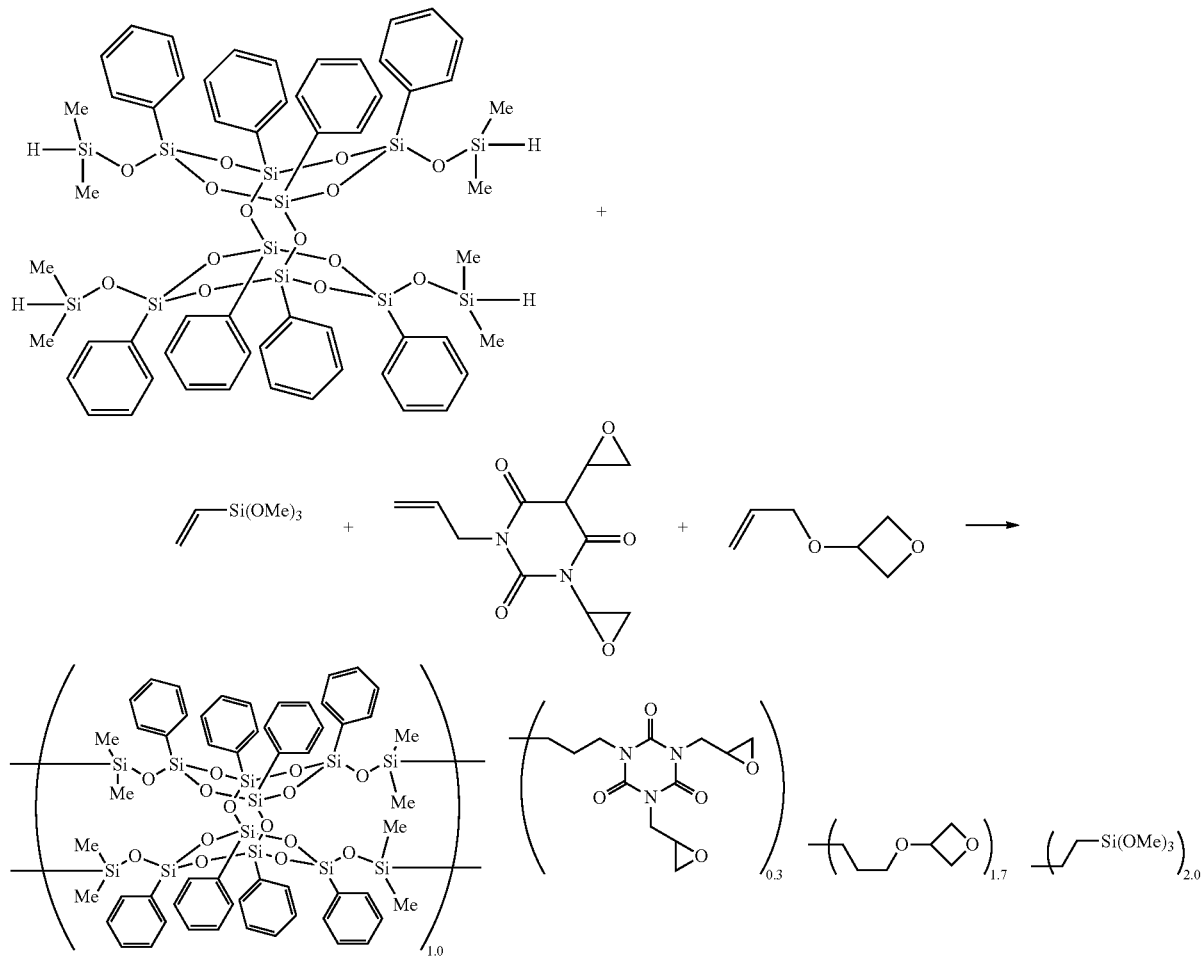

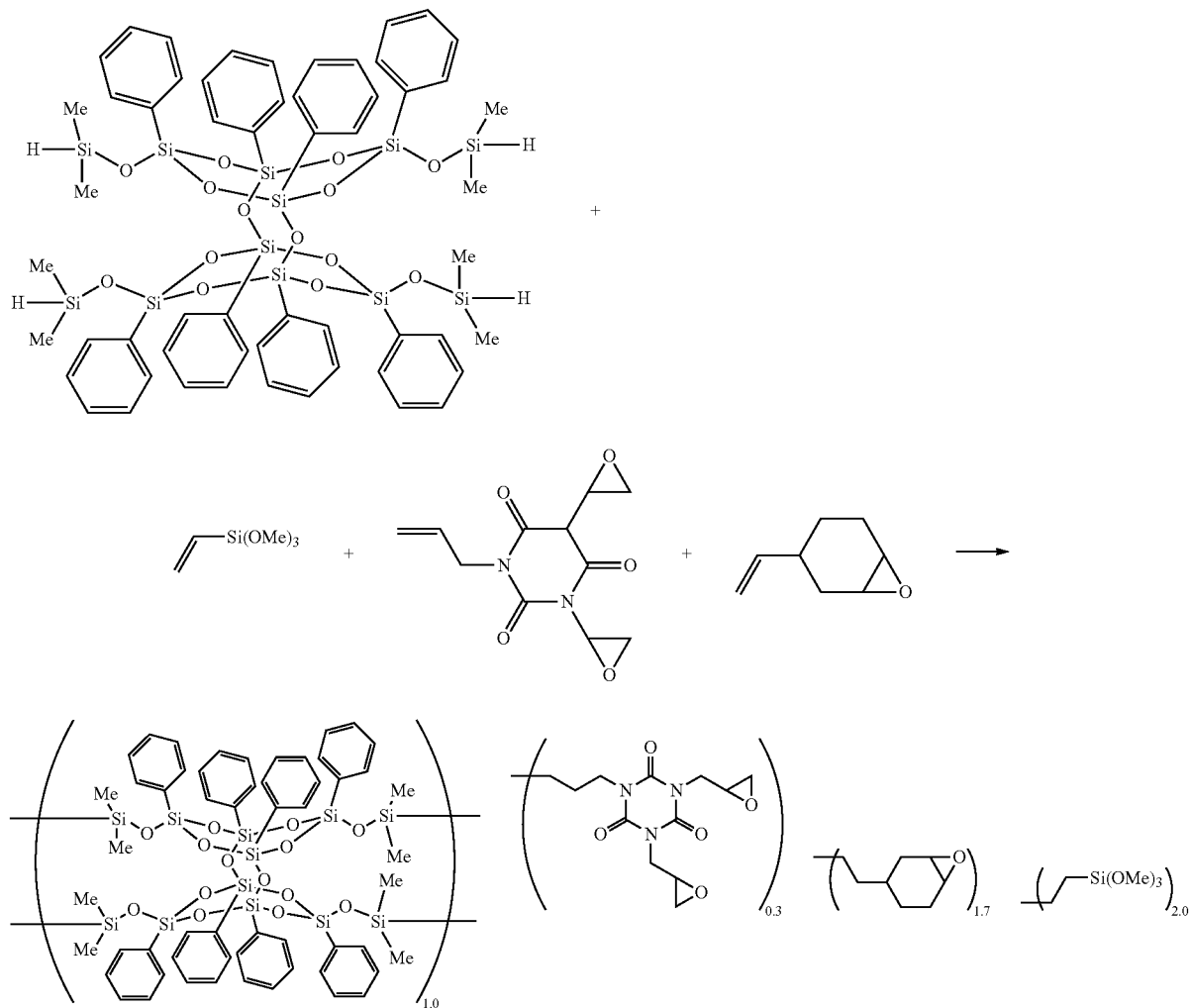

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741, dry toluene (100 g) and monoallyl diglycidyl isocyanurate (6.5 g) produced by Shikoku Chemicals Corporation, and sealed with dry nitrogen. The contents were heated under stirring with a magnetic stirrer to a reaction temperature of 100° C.

A Pt catalyst (30 μL) was added using a microsyringe, followed by stirring for 30 minutes. Subsequently, CELLOXIDE 2000 (16.2 g) produced by Daicel Corporation was slowly added dropwise, followed by stirring for 1 hour. Furthermore, Silaplane S210 (34.1 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 100° C. under vacuum to obtain a colorless transparent viscous liquid (yield: 145 g).

Synthesis Example 16

Compound (A16) was produced according to the following formula.

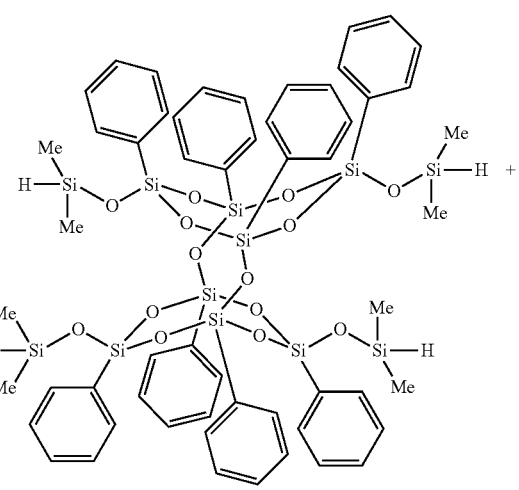

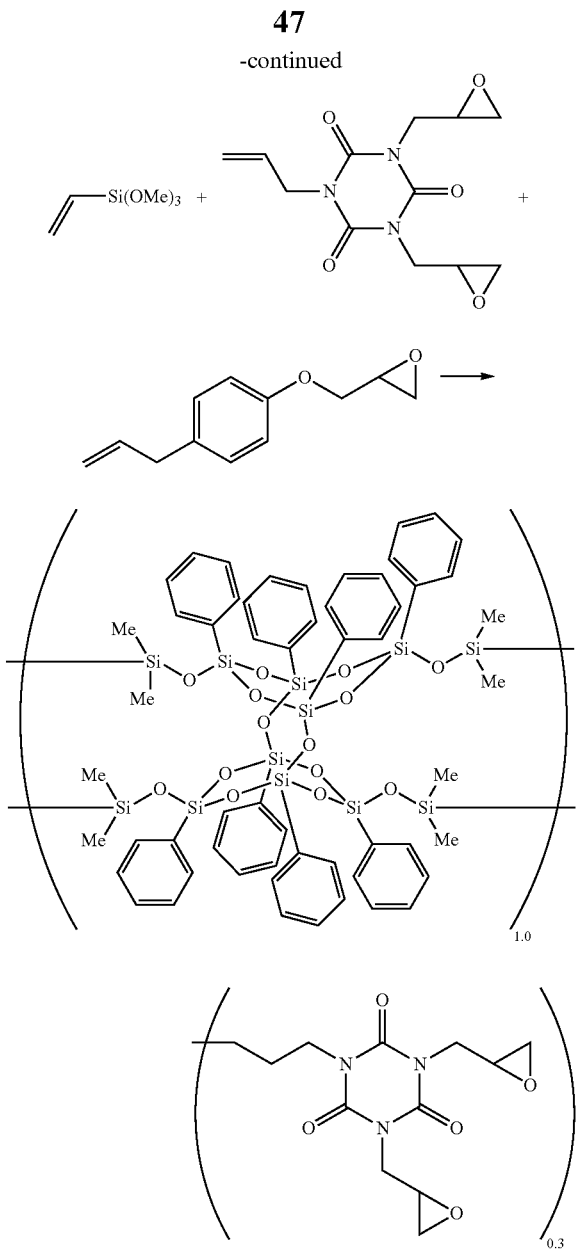

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741, dry toluene (100 g) and monoallyl diglycidyl isocyanurate (6.5 g) produced by Shikoku Chemicals Corporation, and sealed with dry nitrogen. The contents were heated under stirring with a magnetic stirrer to a reaction temperature of 100° C.

A Pt catalyst (30 µL) was added using a microsyringe, followed by stirring for 30 minutes. Subsequently, allylphenyl glycidyl ether (24.8 g) produced by Yokkaichi Chemical Company Limited was slowly added dropwise, followed by stirring for 1 hour. Furthermore, Silaplane S210 (34.1 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 100° C. under vacuum to obtain a colorless transparent viscous liquid (yield: 154 g).

Synthesis Example 17

Compound (A17) was produced according to the following formula.

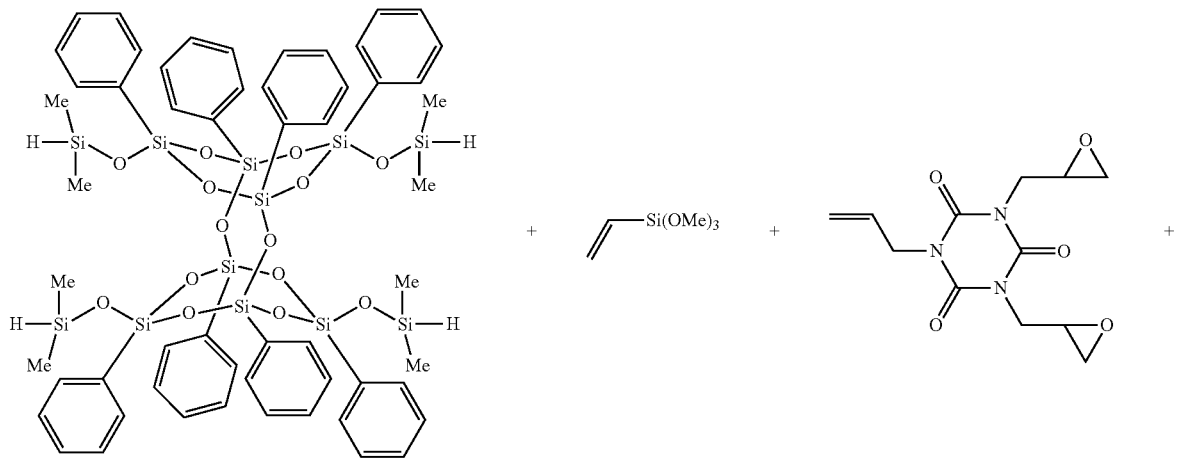

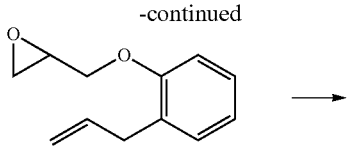

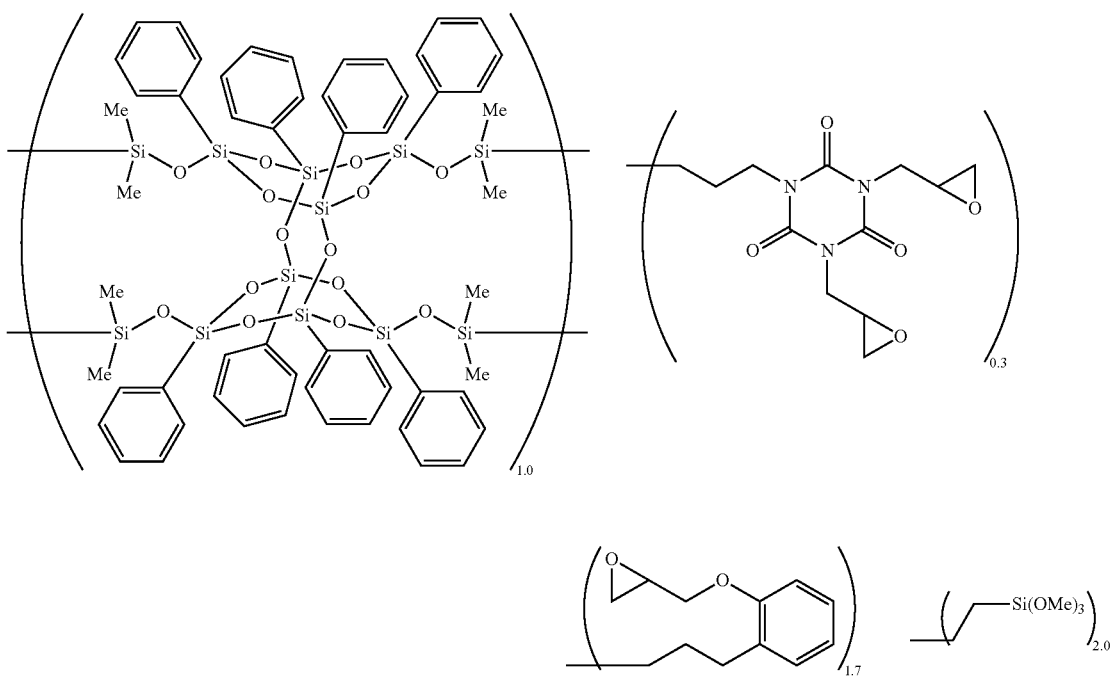

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741, dry toluene (100 g) and monoallyl diglycidyl isocyanurate (6.5 g) produced by Shikoku Chemicals Corporation, and sealed with dry nitrogen. The contents were heated under stirring with a magnetic stirrer to a reaction temperature of 100° C.

A Pt catalyst (30 μL) was added using a microsyringe, followed by stirring for 30 minutes. Subsequently, ortho-allylphenyl glycidyl ether (24.8 g) was slowly added dropwise, followed by stirring for 1 hour. Furthermore, Silaplane S210 (34.1 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 100° C. under vacuum to obtain a colorless transparent viscous liquid (yield: 154 g).

Synthesis Example 18

Compound (A18) was produced according to the following formula.

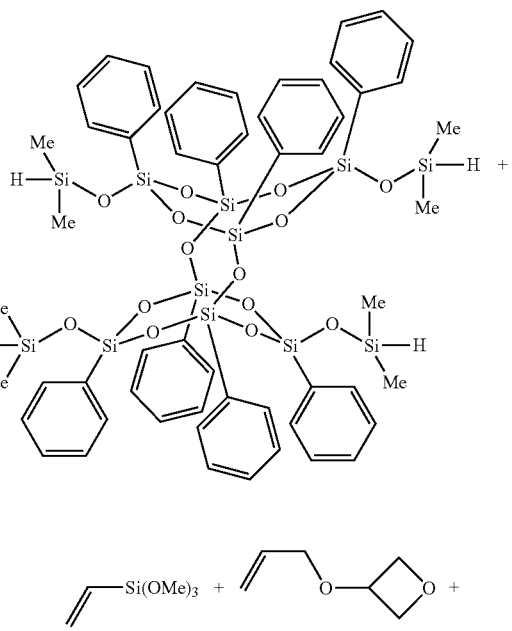

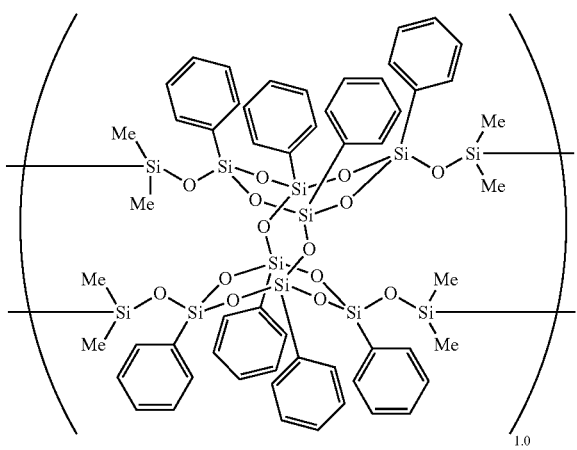

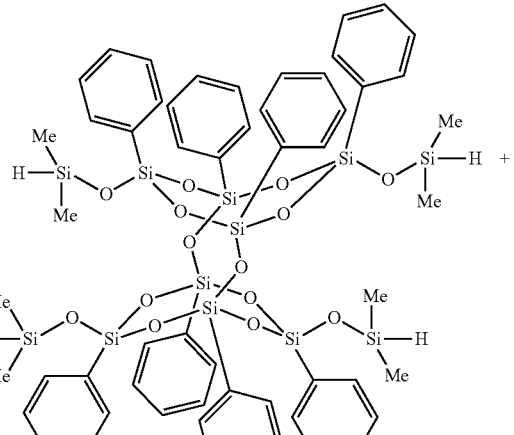

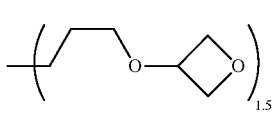

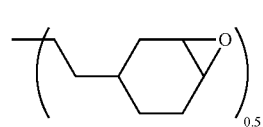

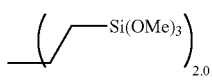

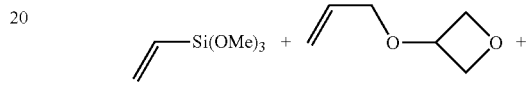

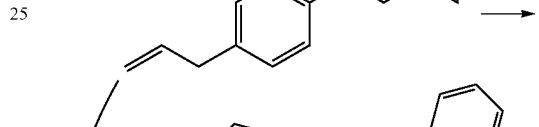

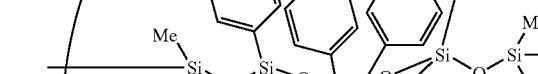

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 μL) was added using a microsyringe, and allyloxyoxetane (13.2 g) produced by Yokkaichi Chemical Company Limited was slowly added dropwise from the dropping funnel, followed by stirring for 1 hour. Subsequently, Celloxide 2000 (4.8 g) produced by Daicel Corporation was slowly added dropwise, followed by stirring for 1 hour. Furthermore, Silaplane S210 (34.2 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 100° C. under vacuum to obtain a colorless transparent viscous liquid (yield: 140 g).

Synthesis Example 19

Compound (A19) was produced according to the following formula.

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 μL) was added using a microsyringe, and allyloxyoxetane (13.2 g) produced by Yokkaichi Chemical Company Limited was slowly added dropwise from the dropping funnel, followed by stirring for 1 hour. Subsequently, allylphenyl glycidyl ether (7.3 g) produced by Yokkaichi Chemical Company Limited was slowly added dropwise, followed by stirring for 1 hour. Furthermore, Silaplane 5210 (34.2 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 100° C. under vacuum to obtain a colorless transparent viscous liquid (yield: 143 g).

Synthesis Example 20

Compound (A20) was produced according to the following formula.

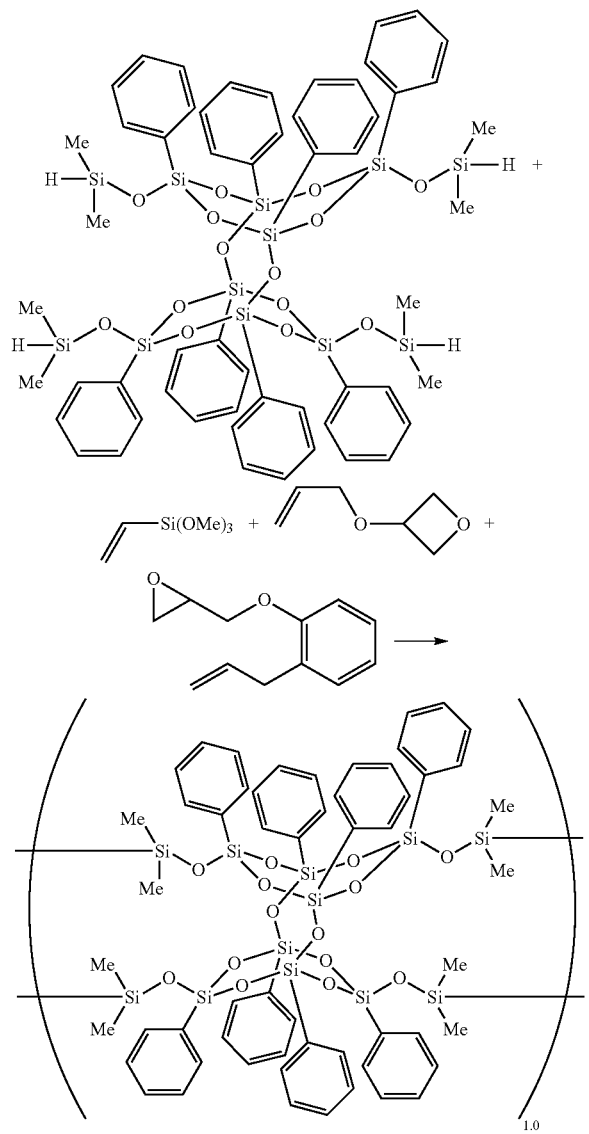

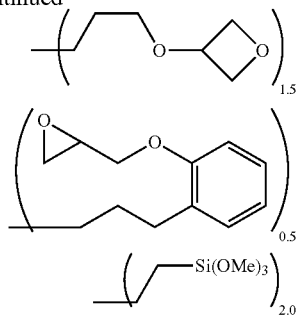

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 μL) was added using a microsyringe, and allyloxyoxetane (13.2 g) produced by Yokkaichi Chemical Company Limited was slowly added dropwise from the dropping funnel, followed by stirring for 1 hour. Subsequently, o-allylphenyl glycidyl ether (7.3 g) was slowly added dropwise, followed by stirring for 1 hour. Furthermore, Silaplane S210 (34.2 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 100° C. under vacuum to obtain a colorless transparent viscous liquid (yield: 143 g).

Synthesis Example 21

Compound (A21) was produced according to the following formula.

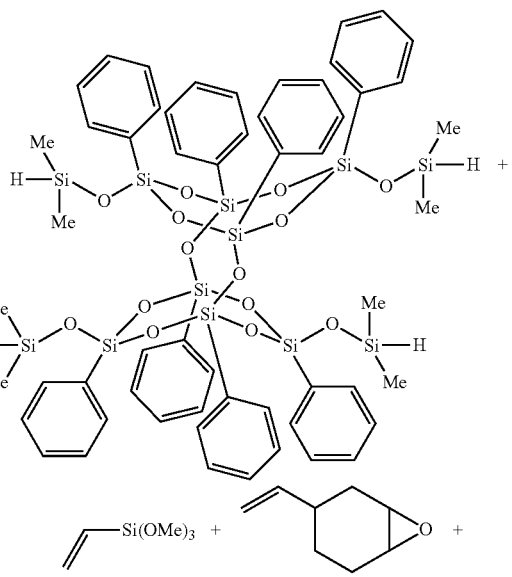

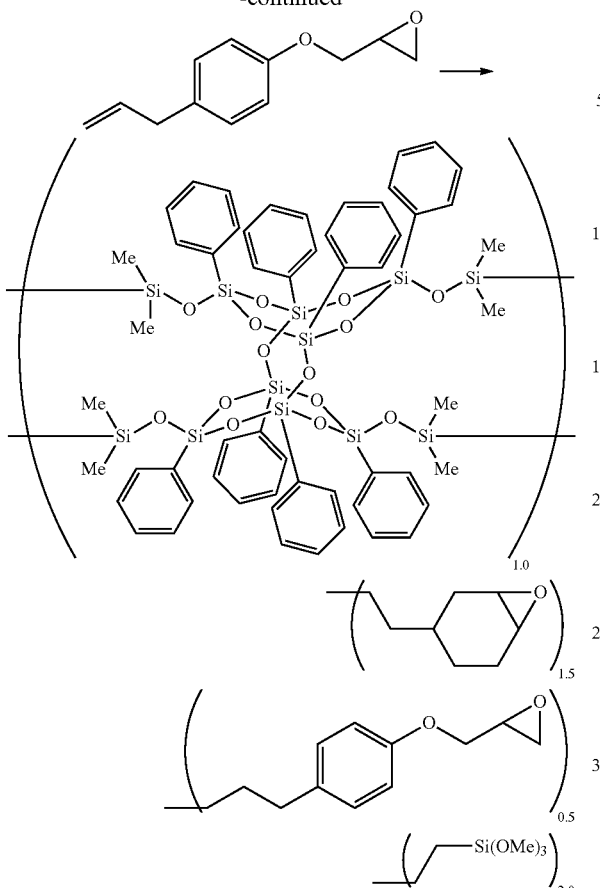

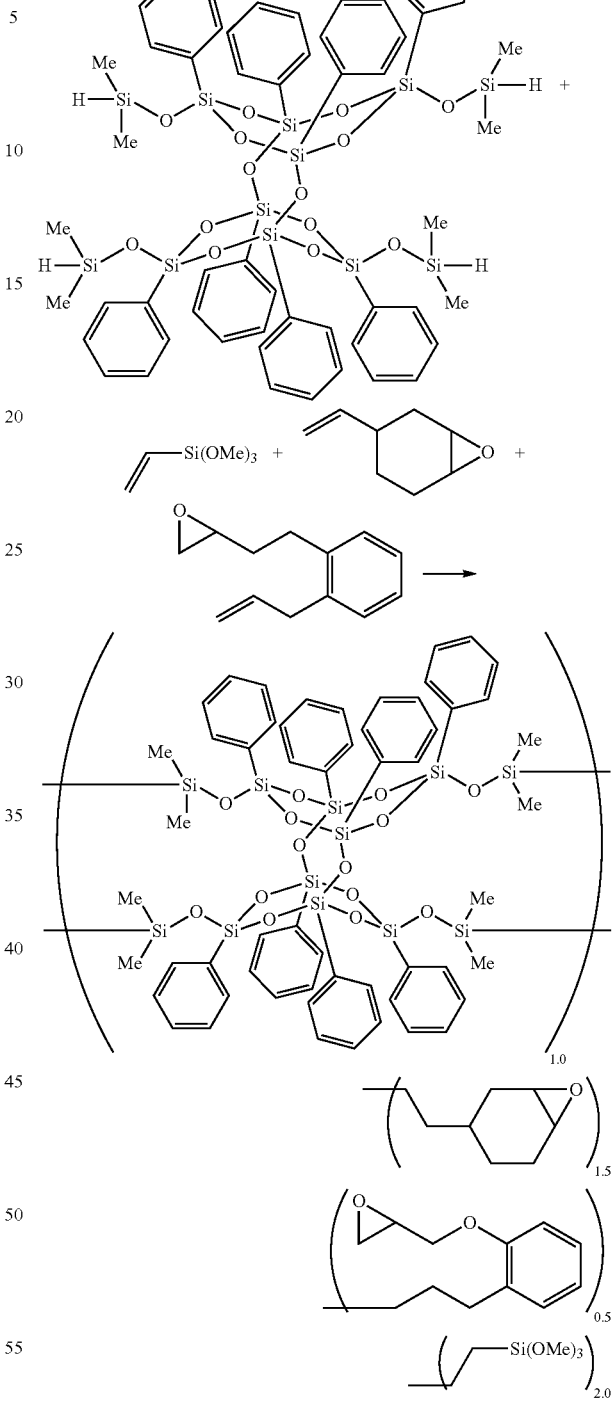

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 μL) was added using a microsyringe, and Celloxide 2000 (14.3 g) produced by Daicel Corporation was slowly added dropwise from the dropping funnel, followed by stirring for 1 hour. Subsequently, allylphenyl glycidyl ether (7.3 g) produced by Yokkaichi Chemical Company Limited was slowly added dropwise, followed by stirring for 1 hour. Further, Silaplane S210 (34.2 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 100° C. under vacuum to obtain a colorless transparent viscous liquid (yield: 144 g).

Synthesis Example 22

Compound (A22) was produced according to the following formula.

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (30 μL) was added using a microsyringe, and CELLOXIDE 2000 (14.3 g) produced by Daicel Corporation was slowly added dropwise from dropping funnel, followed by stirring for 1 hour. Subsequently, ortho-allylphenyl glycidyl ether (7.3 g) was slowly added dropwise, followed by stirring for 1 hour. Furthermore, Silaplane S210 (34.2 g) produced by JNC Corporation was added dropwise, followed by stirring for 3 hours. After cooling, activated carbon at 3 mass % was added to the crude product, and the resulting mixture was stirred at room temperature through the night.

Thereafter, filtration was performed, and the filtrate was concentrated in an evaporator. The obtained concentrate was subjected to drying/monomer removal at 100° C. under vacuum to obtain a colorless transparent viscous liquid (yield: 144 g).

Synthesis Example 23

Modification Example of Silicon Compound Having Alkoxysilyl Group

Compound (A23) was produced according to the following formula.

In a nitrogen atmosphere, a reaction vessel equipped with a thermometer, a dropping funnel and a reflux condenser and having an inner volume of 200 mL was charged with compound (A2) (30 g) synthesized in Synthesis Example 2, dry toluene (30 g), SK1BH (0.3 g) produced by Mitsubishi Chemical Corporation and ultrapure water (1.24 g), and the contents were heated under stirring at 40° C. for 5 hr. Then, filtration was performed, and the filtrate was concentrated in an evaporator to obtain a colorless transparent viscous liquid (40 g).

Synthesis Example 24

Compound (A24) was produced according to the following formula.

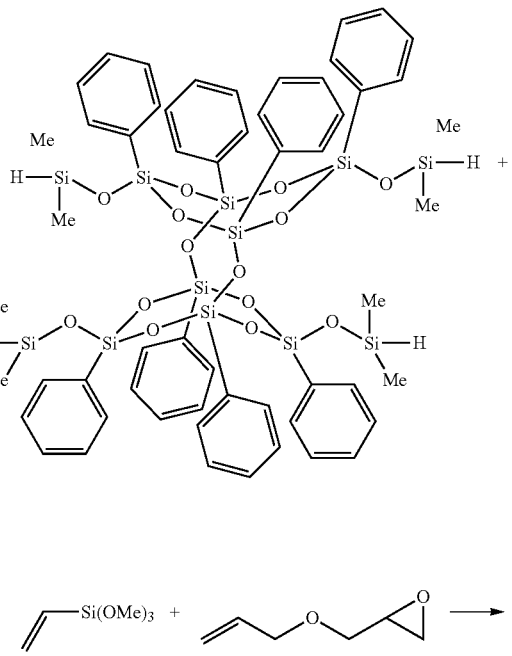

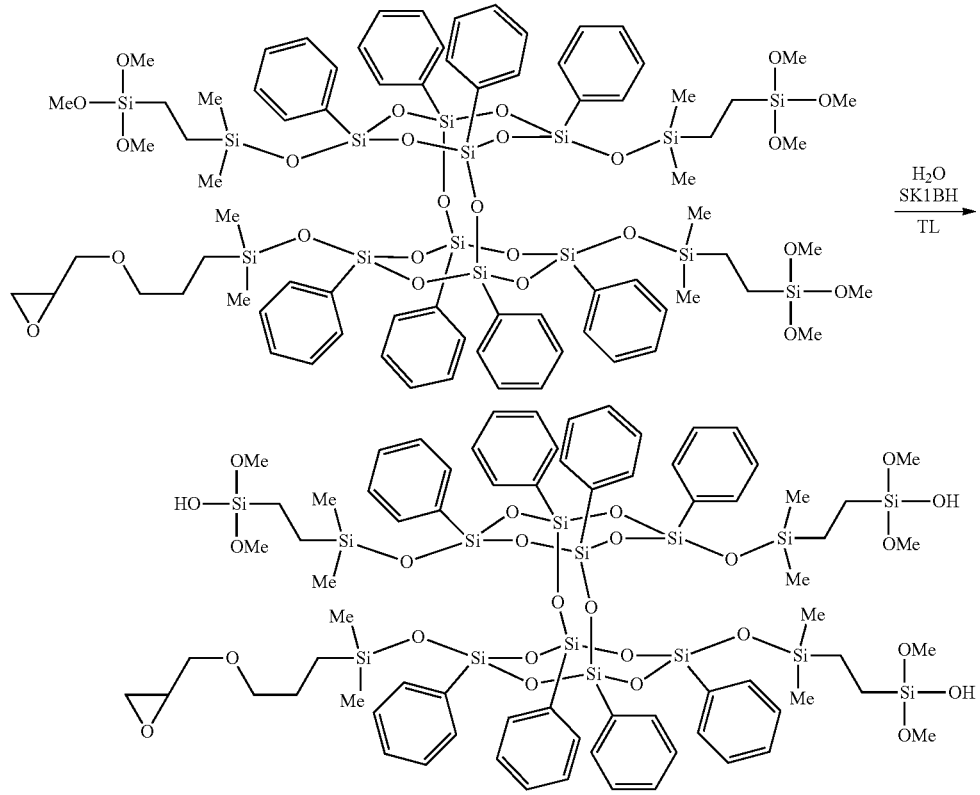

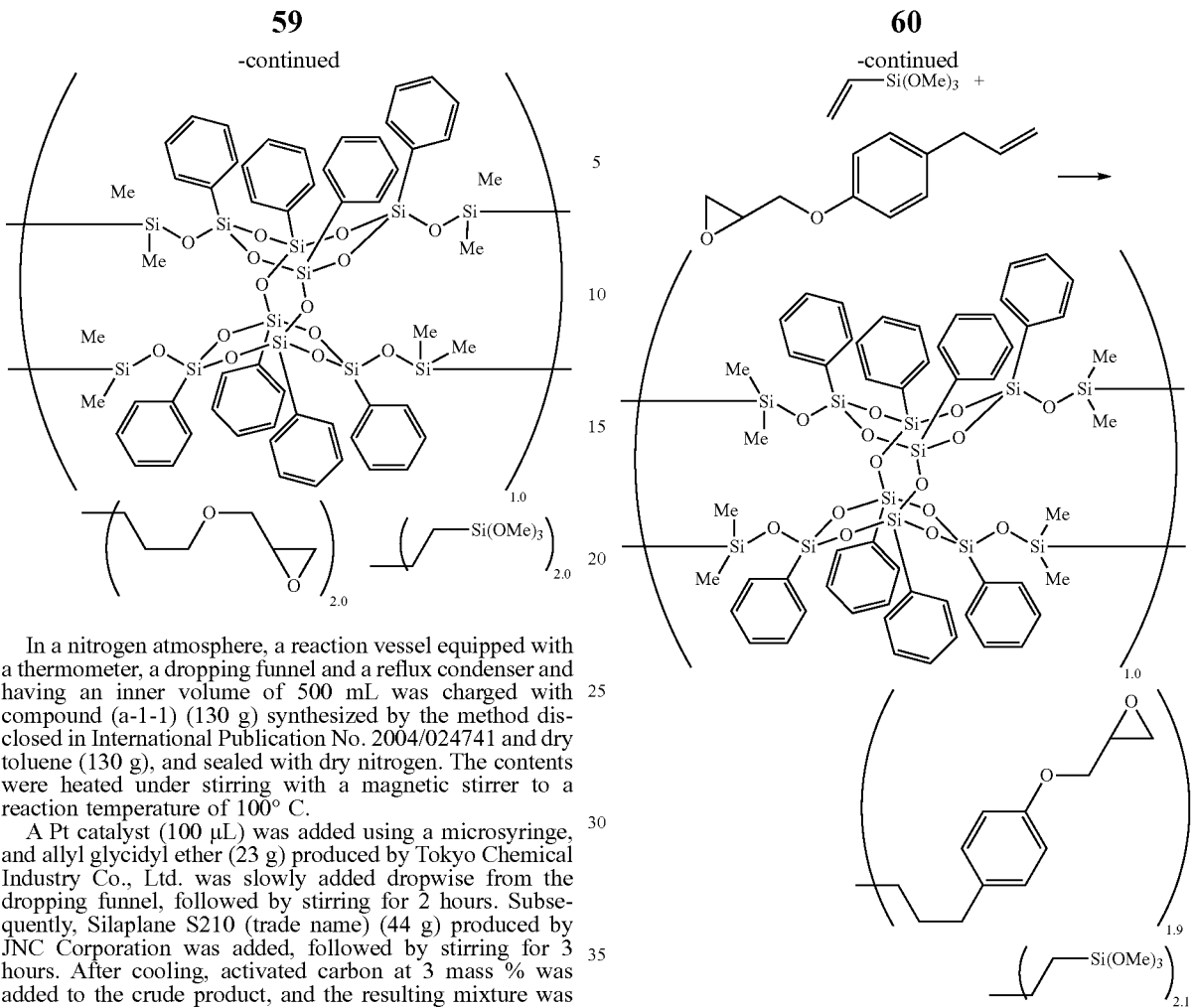

In a nitrogen atmosphere, a reaction vessel equipped with a thermometer, a dropping funnel and a reflux condenser and having an inner volume of 500 mL was charged with compound (a-1-1) (130 g) synthesized by the method disclosed in International Publication No. 2004/024741 and dry toluene (130 g), and sealed with dry nitrogen. The contents were heated under stirring with a magnetic stirrer to a reaction temperature of 100° C.

A Pt catalyst (100 μL) was added using a microsyringe, and allyl glycidyl ether (23 g) produced by Tokyo Chemical Industry Co., Ltd. was slowly added dropwise from the dropping funnel, followed by stirring for 2 hours. Subsequently, Silaplane S210 (trade name) (44 g) produced by JNC Corporation was added, followed by stirring for 3 hours. After cooling, activated carbon at 3 mass % was added to the crude product, and the resulting mixture was stirred at room temperature through the night.

Figure 7:
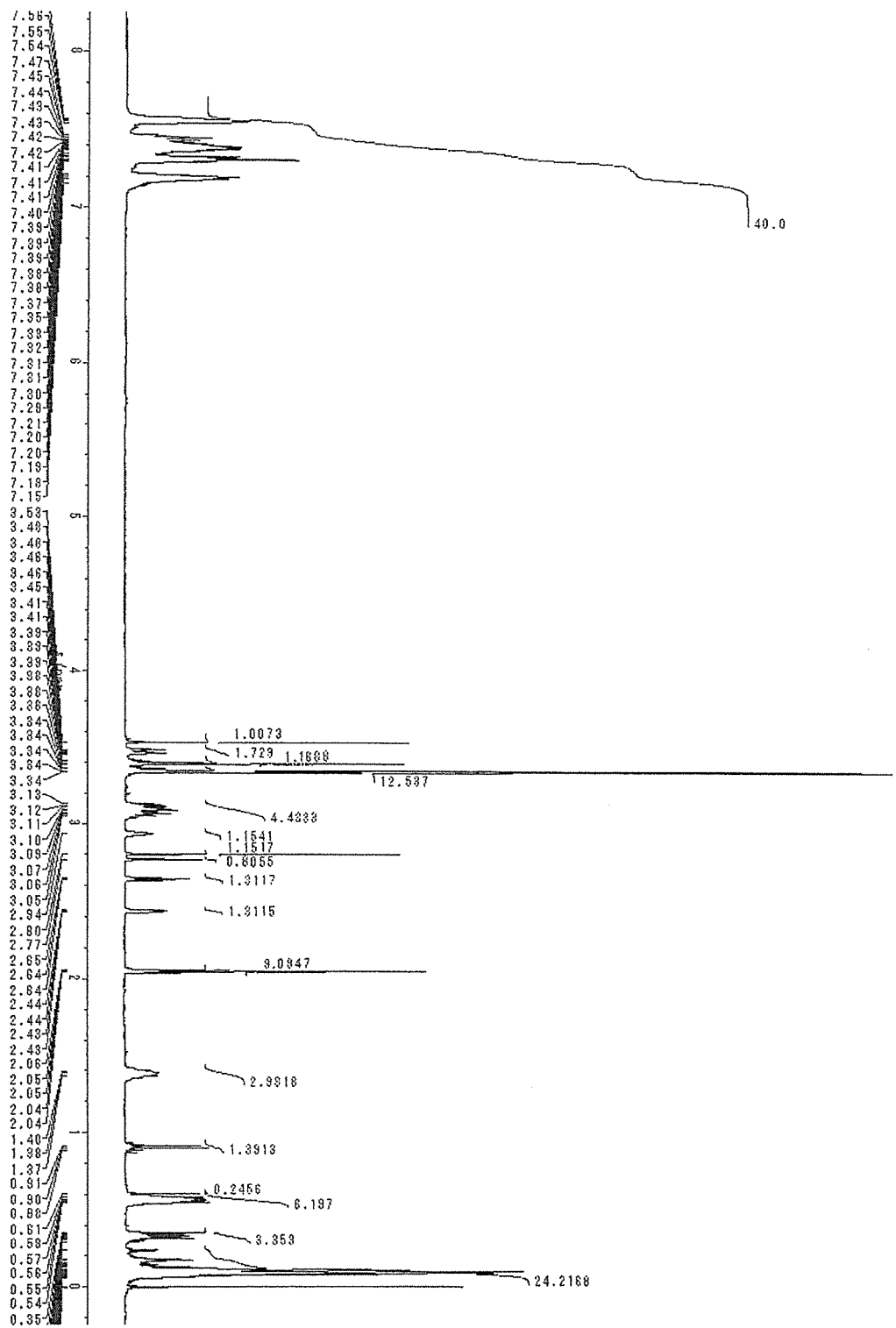
FIG. 7 shows the NMR chart of Synthesis Example 25.

Thereafter, filtration was performed, and the filtrate was concentrated in an evaporator. The obtained concentrate was subjected to drying/monomer removal at 100° C. under vacuum to obtain a colorless transparent viscous liquid (yield: 180 g). The epoxy equivalent of (A24) was measured according to JIS K-7236 (2009) and found to be 1,073 g/mol. The NMR charge is shown in FIG. 7.

Synthesis Example 25

Compound (A25) was produced according to the following formula.

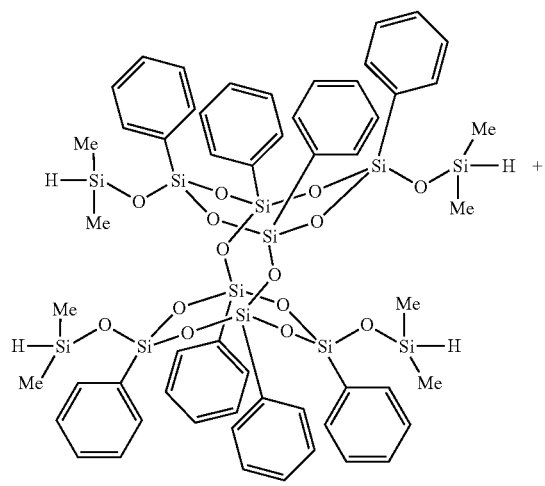

In a nitrogen atmosphere, a reaction vessel equipped with a thermometer, a dropping funnel and a reflux condenser and having an inner volume of 300 mL was charged with compound (a-1-1) (100 g) synthesized by the method disclosed in International Publication No. 2004/024741 and dry toluene (100 g), and sealed with dry nitrogen. The contents were heated under stirring with a magnetic stirrer to a reaction temperature of 100° C.

A Pt catalyst (60 μL) was added using a microsyringe, and allylphenyl glycidyl ether (27.8 g) produced by Yokkaichi Chemical Company Limited was slowly added dropwise from the dropping funnel, followed by stirring for 3 hours. Subsequently, Silaplane S210 (33.0 g) produced by JNC Corporation was added dropwise, followed by stirring for 3 hours. After cooling, activated carbon at 3 mass % was added to the crude product, and the resulting mixture was stirred at room temperature through the night.

Figure 8:
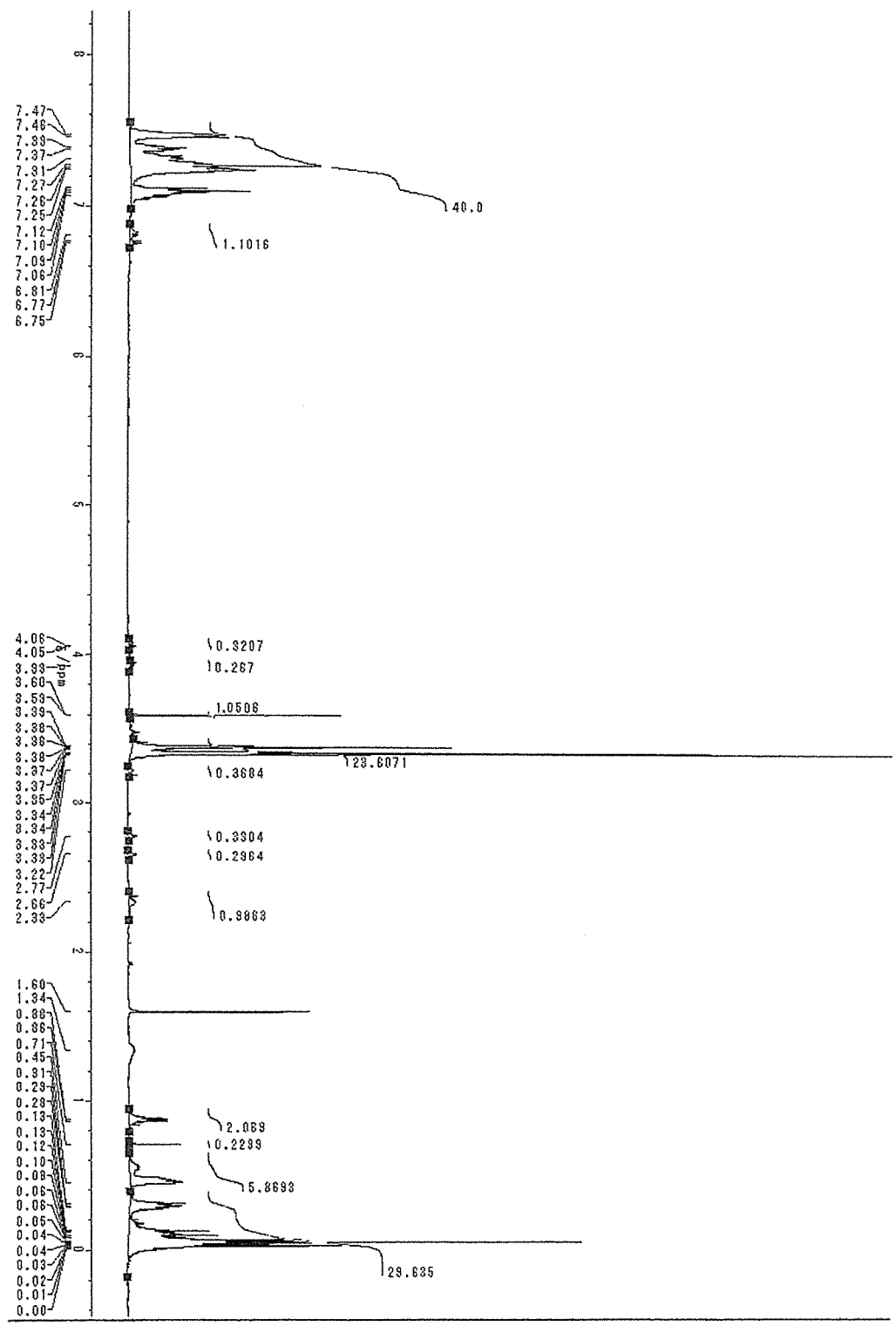
FIG. 8 shows the NMR chart of Synthesis Example 26.

Thereafter, filtration was performed, and the filtrate was concentrated in an evaporator. The obtained concentrate was subjected to drying/monomer removal at 110° C. under vacuum to obtain a colorless transparent viscous liquid (yield: 145 g). The NMR chart is shown in FIG. 8.

Synthesis Example 26

Compound (A26) was produced according to the following formula.

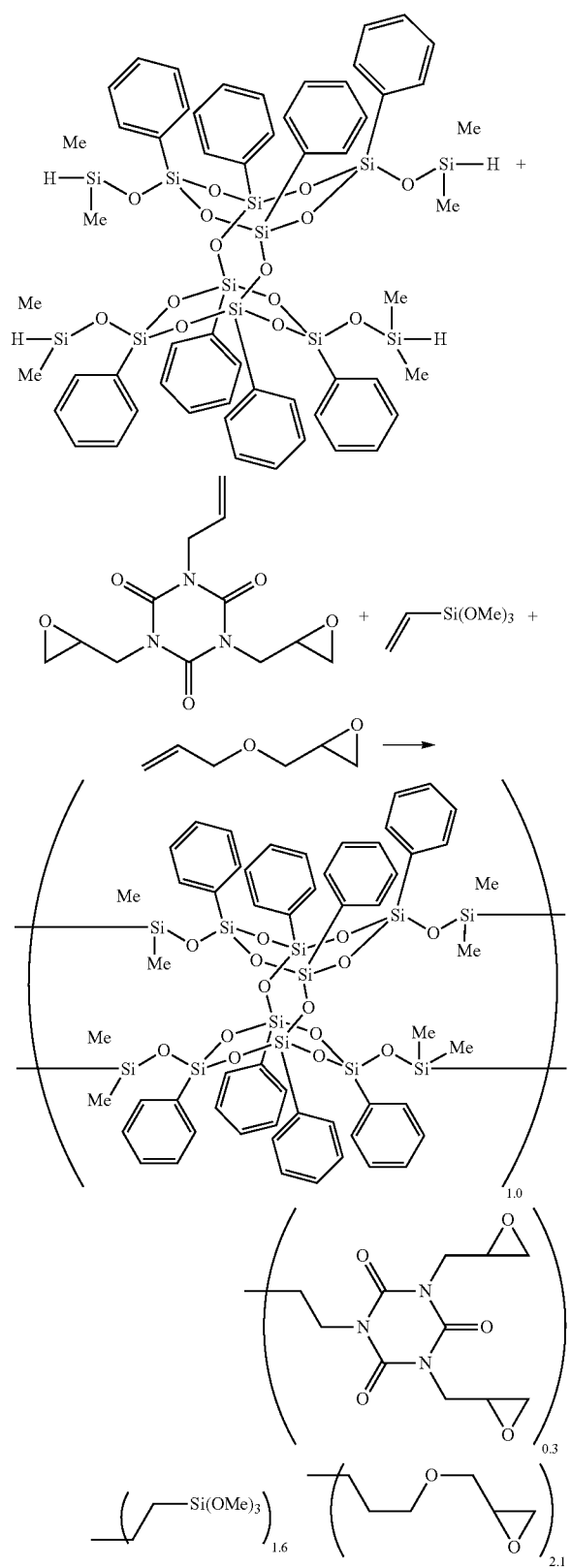

In a nitrogen atmosphere, a reaction vessel equipped with a thermometer, a dropping funnel and a reflux condenser and having an inner volume of 500 mL was charged with compound (a-1-1) (150 g) synthesized by the method disclosed in International Publication No. 2004/024741, dry toluene (150 g) and monoallyl diglycidyl isocyanurate (9.7 g) produced by Shikoku Chemicals Corporation, and sealed with dry nitrogen. The contents were heated under stirring with a magnetic stirrer to a reaction temperature of 100° C.

A Pt catalyst (60 µL) was added using a microsyringe, followed by stirring for 30 minutes. Subsequently, Silaplane S210 (27.3 g) produced by JNC Corporation was added dropwise, followed by stirring for 1 hour. Furthermore, allyl glycidyl ether (34.7 g) produced by Tokyo Chemical Industry Co., Ltd. was slowly added dropwise, followed by stirring for 2 hours. After cooling, activated carbon at 3 mass % was added to the crude product, and the resulting mixture was stirred at room temperature through the night.

Figure 9:
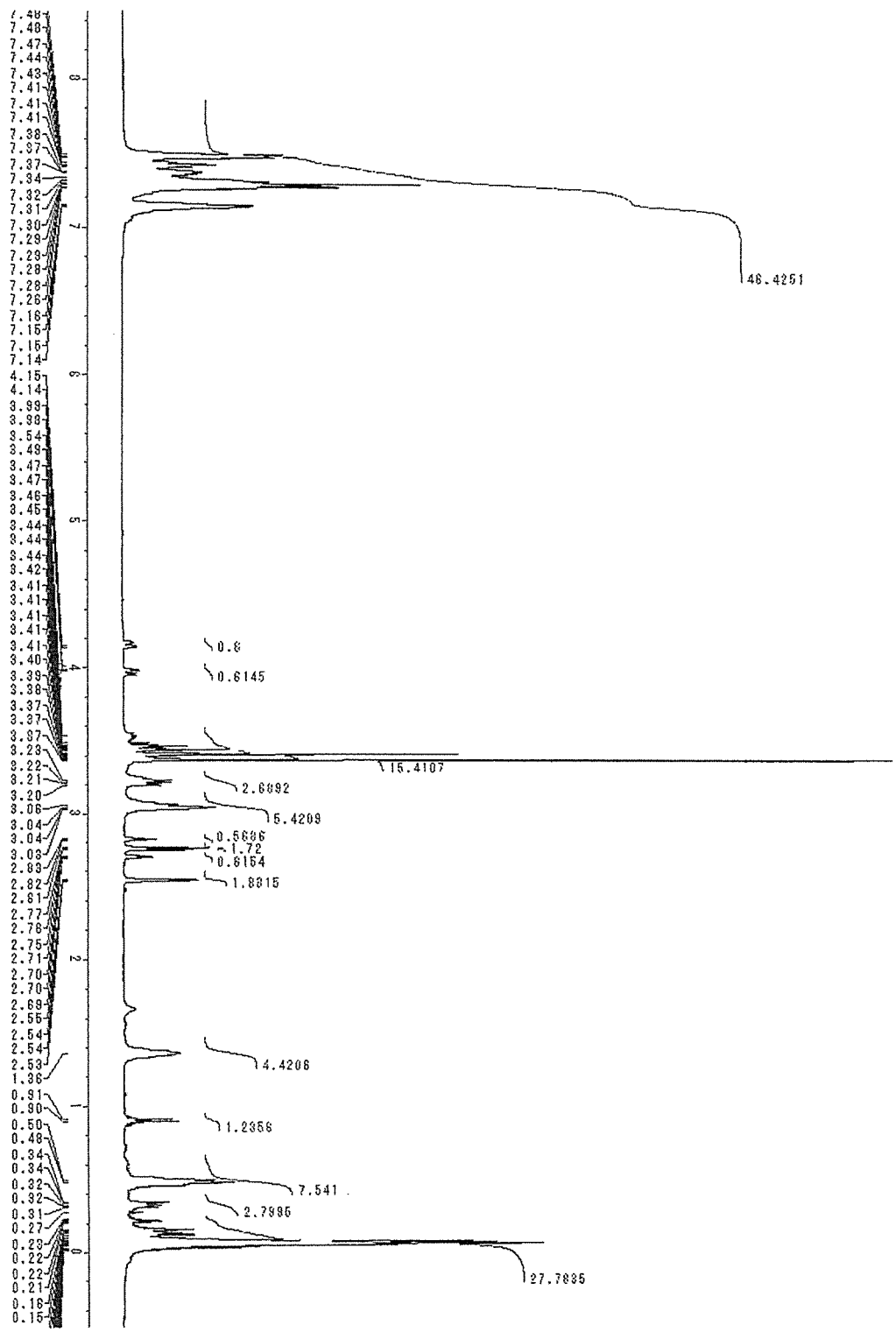
FIG. 9 shows the NMR chart of Synthesis Example 27.

Thereafter, filtration was performed, and the filtrate was concentrated in an evaporator. The obtained concentrate was subjected to drying/monomer removal at 110° C. under vacuum to obtain a colorless transparent viscous liquid (yield: 210 g). The NMR chart is shown in FIG. 9.

Synthesis Example 27

Compounding (A27) of Silicon Compound and Silica Sol

A Kjeldahl flask having an inner volume of 300 mL was charged with Compound (A1) (70 g) synthesized in Synthesis Example 1 and silica sol IPA-ST (product name; 87.5 g) produced by Nissan Chemical Industries, Ltd., and the contents were heated under stirring at 40° C. for 12 hours to obtain a surface-modified nanosilica solution (A27).

Main Materials Used in This Example:
[Silicon Compound]
  Compounds (A1) to (A27) produced in Production Examples 1 to 27
  Compound (A') satisfying formula (α) of p=4, used as Comparative Example
  Silicon resin [OE-6630 (product name)] produced by Dow Corning Toray Co., Ltd., used as Comparative Example
[Curing Agent]
  Thermal cationic polymerization initiator [TA100 (trade name)] produced by San-Apro Ltd.
[Epoxy Resin Containing No Benzene Ring and No Silicon Atom in Molecule]
  Epoxy resin [CELLOXIDE (trade name) CEL2021P] produced by Daicel Corporation
  Epoxy resin [jER (trade name) YX8000] produced by Mitsubishi Chemical Corporation
  Oxetane resin [Aron Oxetane (trade name) OXT-221] produced by Toagosei Co., Ltd.
[Stabilizer]
  Antioxidant [Irganox 1010 (trade name)] produced by BASF Japan Ltd.
  Antioxidant [Irgafos 168 (trade name)] produced by BASF Japan Ltd.
[Silane Coupling Agent]
  Silane coupling agent [Sila-Ace (registered trademark) 5510] produced by JNC Corporation
  (Production of Cured Products 1 to 56)
  For each of Compounds (A1) to (A27) synthesized in Synthesis Examples 1 to 27 or Compound (A') satisfying formula (α) of p=4, a mixture of it with an epoxy resin containing no silicon atom in the molecule, an oxetane resin, a silane coupling agent and a stabilizer was put in a screw tube and dissolved by stirring under heating, and a thermal cationic polymerization initiator was then added as a curing agent and dissolved.

As to Compound (A27) synthesized in Synthesis Example 27, a mixture of an epoxy resin containing no silicon atom in the molecule, an oxetane resin, a silane coupling agent and a stabilizer was put in the tube and dissolved by stirring under heating, and isopropanol derived from the raw material was removed by distillation under reduced pressure by using an evaporator.

The screw tube was set in a rotation/revolution mixer [Thinky Mixer ARE-250 (trade name), manufactured by Thinky Corporation], and mixing/defoaming was performed to make a varnish. In the following description, the varnish is sometimes referred to as the curable resin composition.

(Curing Method 1)

The varnish was coated to a thickness of 100 μm on a glass substrate without the entry of an air bubble and cured by placing the substrate in an oven that was warmed to 120° C. Heating was performed, in order, at 120° C. for 1 hour, at 150° C. for 5 hours, and at 180° C. for 2 hours, and a coating-like cured product of epoxy silsesquioxane having alkoxysilyl groups was obtained. The cured product obtained was used for tests of initial transmissivity, heat-resistant transparency, and heat yellowing resistance.

(Production of Cured Product 57)

OE-6630 produced by Dow Corning Toray Co., Ltd. was blended in a specified ratio recommended by the maker, stirred at room temperature for 5 min and then mixed/defoamed by Thinky Mixer. The obtained varnish was coated to a thickness of 100 μm on a glass substrate without the entry of an air bubble and cured by placing the substrate in an oven that was warmed to 80° C. Heating was performed at 80° C. for 1 hour and at 150° C. for 1 hour, and a coating-like cured product of silicone was obtained. The cured product obtained was used for an initial transmittance test, a heat yellowing resistance test, and an adherence test. The cured product obtained was used for tests of initial transmissivity, heat-resistant transparency, and heat yellowing resistance.

(Curing Method 2)

The varnish was caused to fill an LED-use silver lead frame where the reflector is polyphthalic amide (PPA) or polyamide 9 (PA9T), and cured by placing the lead frame in an oven that was warmed to 120° C. Heating was performed, in order, at 120° C. for 1 hour, at 150° C. for 5 hours, and at 180° C. for 2 hours, thereby encapsulating the lead frame. The sample obtained was used for an adherence test.

Compositions of Cured Products 1 to 56 are shown in Tables 1 to 5.

TABLE 1

| | | | Cured Product | | | | | | | | | | | |
|---|---|---|---|---|---|---|---|---|---|---|---|---|---|---|
| | | | 1 | 2 | 3 | 4 | 5 | 6 | 7 | 8 | 9 | 10 | 11 | 12 |
| Silsesquioxane derivative | Compound A1 | (g) | 60 | 60 | | | | | | | | | | |
| | Compound A2 | (g) | | | 60 | 60 | | | | | | | | |
| | Compound A3 | (g) | | | | | 60 | 60 | | | | | | |
| | Compound A4 | (g) | | | | | | | 50 | 50 | | | | |
| | Compound A5 | (g) | | | | | | | | | 50 | 50 | | |
| | Compound A6 | (g) | | | | | | | | | | | 55 | 50 |
| Epoxy resin | CEL2021P | (g) | 10 | | 10 | | 10 | | 10 | | 10 | | 10 | |
| | YX8000 | (g) | | 10 | | 10 | | 10 | | 10 | | 10 | | 15 |
| Oxetane resin | OXT-221 | (g) | 25 | 25 | 25 | 25 | 25 | 25 | 35 | 35 | 35 | 35 | 30 | 30 |
| Silane coupling agent | S510 | (g) | 5 | 5 | 5 | 5 | 5 | 5 | 5 | 5 | 5 | 5 | 5 | 5 |
| Curing agent | TA100 | (mg) | 30 | 30 | 30 | 30 | 30 | 30 | 30 | 30 | 30 | 30 | 30 | 30 |
| | BuSnOAc | (mg) | | 15 | | 15 | | 15 | | 15 | | 15 | 15 | 15 |
| Stabilizer | Irganox 1010 | (mg) | 250 | 250 | 250 | 250 | 250 | 250 | 250 | 250 | 250 | 250 | 250 | 250 |
| | Irgafos 168 | (mg) | 750 | 750 | 750 | 750 | 750 | 750 | 750 | 750 | 750 | 750 | 750 | 750 |

TABLE 2

| | | | Cured Product | | | | | | | | | | | |
|---|---|---|---|---|---|---|---|---|---|---|---|---|---|---|
| | | | 13 | 14 | 15 | 16 | 17 | 18 | 19 | 20 | 21 | 22 | 23 | 24 |
| Silsesquioxane derivative | Compound A7 | (g) | 55 | 50 | | | | | | | | | | |
| | Compound A8 | (g) | | | 55 | 50 | | | | | | | | |
| | Compound A9 | (g) | | | | | 60 | 60 | | | | | | |
| | Compound A10 | (g) | | | | | | | 55 | 50 | | | | |
| | Compound A11 | (g) | | | | | | | | | 55 | 50 | | |
| | Compound A12 | (g) | | | | | | | | | | | 60 | 60 |
| | Compound A13 | (g) | | | | | | | | | | | | |
| Epoxy resin | CEL2021P | (g) | 10 | | 10 | | 10 | | 10 | | 10 | | 10 | |
| | YX8000 | (g) | | 15 | | 15 | | 15 | | 15 | | 15 | | 10 |
| Oxetane resin | OXT-221 | (g) | 30 | 30 | 30 | 30 | 25 | 20 | 30 | 30 | 30 | 30 | 25 | 25 |
| Silane coupling agent | S510 | (g) | 5 | 5 | 5 | 5 | 5 | 5 | 5 | 5 | 5 | 5 | 5 | 5 |
| Curing agent | TA100 | (mg) | 30 | 30 | 30 | 30 | 30 | 30 | 30 | 30 | 30 | 30 | 30 | 30 |
| | BuSnOAc | (mg) | 15 | 15 | 15 | 15 | | | 15 | 15 | 15 | 15 | 15 | 15 |
| Stabilizer | Irganox 1010 | (mg) | 250 | 250 | 250 | 250 | 250 | 250 | 250 | 250 | 250 | 250 | 250 | 250 |
| | Irgafos 168 | (mg) | 750 | 750 | 750 | 750 | 750 | 750 | 750 | 750 | 750 | 750 | 750 | 750 |

TABLE 3

| | | | \multicolumn{12}{c}{Cured Product} |
|---|---|---|---|---|---|---|---|---|---|---|---|---|---|---|
| | | | 25 | 26 | 27 | 28 | 29 | 30 | 31 | 32 | 33 | 34 | 35 | 36 |
| Silsesquioxane derivative | Compound A13 | (g) | 60 | 60 | | | | | | | | | | |
| | Compound A14 | (g) | | | 55 | 50 | | | | | | | | |
| | Compound A15 | (g) | | | | | 55 | 50 | | | | | | |
| | Compound A16 | (g) | | | | | | | 55 | 50 | | | | |
| | Compound A17 | (g) | | | | | | | | | 55 | 50 | | |
| | Compound A18 | (g) | | | | | | | | | | | 55 | 50 |
| Epoxy resin | CEL2021P | (g) | 10 | | 10 | | 10 | | 10 | | 10 | | 10 | |
| | YX8000 | (g) | | 10 | | 15 | | 15 | | 15 | | 15 | | 15 |
| Oxetane resin | OXT-221 | (g) | 25 | 25 | 30 | 30 | 30 | 30 | 30 | 30 | 30 | 30 | 30 | 30 |
| Silane coupling agent | S510 | (g) | 5 | 5 | 5 | 5 | 5 | 5 | 5 | 5 | 5 | 5 | 5 | 5 |
| Curing agent | TA100 | (mg) | 30 | 30 | 30 | 30 | 30 | 30 | 30 | 30 | 30 | 30 | 30 | 30 |
| | BuSnOAc | (mg) | 15 | 15 | 15 | 15 | 15 | 15 | 15 | 15 | 15 | 15 | 15 | 15 |
| Stabilizer | Irganox 1010 | (mg) | 250 | 250 | 250 | 250 | 250 | 250 | 250 | 250 | 250 | 250 | 250 | 250 |
| | Irgafos 168 | (mg) | 750 | 750 | 750 | 750 | 750 | 750 | 750 | 750 | 750 | 750 | 750 | 750 |

TABLE 4

| | | | \multicolumn{12}{c}{Cured Product} |
|---|---|---|---|---|---|---|---|---|---|---|---|---|---|---|
| | | | 37 | 38 | 39 | 40 | 41 | 42 | 43 | 44 | 45 | 46 | 47 | 48 |
| Silsesquioxane derivative | Compound A19 | (g) | 55 | 50 | | | | | | | | | | |
| | Compound A20 | (g) | | | 55 | 50 | | | | | | | | |
| | Compound A21 | (g) | | | | | 55 | 50 | | | | | | |
| | Compound A22 | (g) | | | | | | | 55 | 50 | | | | |
| | Compound A23 | (g) | | | | | | | | | 55 | 50 | | |
| | Compound A24 | (g) | | | | | | | | | | | 55 | 50 |
| Epoxy resin | CEL2021P | (g) | 10 | | 10 | | 10 | | 10 | | 10 | | 15 | |
| | YX8000 | (g) | | 15 | | 15 | | 15 | | 15 | | 15 | | 20 |
| Oxetane resin | OXT-221 | (g) | 30 | 30 | 30 | 30 | 30 | 30 | 30 | 30 | 30 | 30 | 35 | 35 |
| Silane coupling agent | S510 | (g) | 5 | 5 | 5 | 5 | 5 | 5 | 5 | 5 | 5 | 5 | 5 | 5 |
| Curing agent | TA100 | (mg) | 30 | 30 | 30 | 30 | 30 | 30 | 30 | 30 | 30 | 30 | 30 | 30 |
| | BuSnOAc | (mg) | 10 | 10 | 10 | 10 | 10 | 10 | 10 | 10 | | | | |
| Stabilizer | Irganox 1010 | (mg) | 250 | 250 | 250 | 250 | 250 | 250 | 250 | 250 | 250 | 250 | 250 | 250 |
| | Irgafos 168 | (mg) | 750 | 750 | 750 | 750 | 750 | 750 | 750 | 750 | 750 | 750 | 750 | 750 |

TABLE 5

| | | | \multicolumn{8}{c}{Cured Product} |
|---|---|---|---|---|---|---|---|---|---|---|
| | | | 49 | 50 | 51 | 52 | 53 | 54 | 55 | 56 |
| Silsesquioxane derivative | Compound A25 | (g) | 55 | 50 | | | | | | |
| | Compound A26 | (g) | | | 55 | 50 | | | | |
| | Compound A27 | (g) | | | | | 55 | 50 | | |
| | Compound A28 | (g) | | | | | | | 55 | 50 |
| Epoxy resin | CEL2021P | (g) | 10 | | 10 | | 10 | | 10 | |
| | YX8000 | (g) | | 15 | | 15 | | 15 | | 15 |
| Oxetane resin | OXT-221 | (g) | 30 | 30 | 30 | 30 | 30 | 30 | 30 | 30 |
| Silane coupling agent | S510 | (g) | 5 | 5 | 5 | 5 | 5 | 5 | 5 | 5 |
| Curing agent | TA100 | (mg) | 30 | 30 | 30 | 30 | 30 | 30 | 30 | 30 |
| | BuSnOAc | (mg) | 5 | 5 | 5 | 5 | | | | |
| Stabilizer | Irganox 1010 | (mg) | 250 | 250 | 250 | 250 | 250 | 250 | 250 | 250 |
| | Irgafos 168 | (mg) | 750 | 750 | 750 | 750 | 750 | 750 | 750 | 750 |

Physical properties of Cured Products 1 to 57 were evaluated by the following methods.

<Initial Transparency>

Each cured product was measured for the light transmittance at the wavelength of 400 nm using an UV-visible spectrophotometer (V-660, made by JASCO Corporation). The initial transparency (400 nm transmittance) was evaluated according to the following criteria. The results are shown in Tables 6 to 15.
A: Light transmittance is 98% or more.
B: Light transmittance is from 90 to less than 98%.
C: Light transmittance is from 80 to less than 90%.
D: Light transmittance is less than 80%.

<Heat-Resistant Transparency>

After the heat-resistance test, the light transmittance at the wavelength of 400 nm was measured, and the heat-resistant transparency (transmittance) was evaluated according to the following criteria.
A: Light transmittance is 97% or more.
B: Light transmittance is from 90% to less than 97%.
C: Light transmittance is less than 90%.

<Heat Yellowing Resistance>

After a heat treatment at 150° C. or 180° C. for 72 hours, the yellowness index (YI) of the cured product was measured. The heat yellowing resistance was evaluated according to the following criteria. The results are shown in Tables 6 to 15.

A: YI value is 0.7 or less.

B: YI value is from more than 0.7 to 1.4.

C: YI value is more than 1.4.

TABLE 6

|  |  | Cured Product 1 | Cured Product 2 | Cured Product 3 | Cured Product 4 | Cured Product 5 | Cured Product 6 |
|---|---|---|---|---|---|---|---|
| 400 nm Transmittance |  | A | A | A | A | A | A |
| 150° C. Heat resistance test | Transmittance (%) | A | A | A | A | A | A |
|  | YI | A | A | A | A | A | A |
| 180° C. Heat resistance test | Transmittance (%) | A | A | A | A | A | A |
|  | YI | A | A | A | A | A | A |

TABLE 7

|  |  | Cured Product 7 | Cured Product 8 | Cured Product 9 | Cured Product 10 | Cured Product 11 | Cured Product 12 |
|---|---|---|---|---|---|---|---|
| 400 nm Transmittance |  | A | A | A | A | A | A |
| 150° C. Heat resistance test | Transmittance (%) | A | A | A | A | A | A |
|  | YI | A | A | A | A | A | A |
| 180° C. Heat resistance test | Transmittance (%) | A | A | B | B | A | A |
|  | YI | A | A | B | B | A | A |

TABLE 8

|  |  | Cured Product 13 | Cured Product 14 | Cured Product 15 | Cured Product 16 | Cured Product 17 | Cured Product 18 |
|---|---|---|---|---|---|---|---|
| 400 nm Transmittance |  | A | A | A | A | A | A |
| 150° C. Heat resistance test | Transmittance (%) | A | A | A | A | A | A |
|  | YI | A | A | A | A | A | A |
| 180° C. Heat resistance test | Transmittance (%) | A | A | B | B | B | B |
|  | YI | A | A | B | B | B | B |

TABLE 9

|  |  | Cured Product 19 | Cured Product 20 | Cured Product 21 | Cured Product 22 | Cured Product 23 | Cured Product 24 |
|---|---|---|---|---|---|---|---|
| 400 nm Transmittance |  | A | A | A | A | A | A |
| 150° C. Heat resistance test | Transmittance (%) | A | A | A | A | A | A |
|  | YI | A | A | A | A | A | A |
| 180° C. Heat resistance test | Transmittance (%) | A | A | B | B | A | A |
|  | YI | A | A | B | B | A | A |

TABLE 10

|  |  | Cured Product 25 | Cured Product 26 | Cured Product 27 | Cured Product 28 | Cured Product 29 | Cured Product 30 |
|---|---|---|---|---|---|---|---|
| 400 nm Transmittance |  | A | A | A | A | A | A |
| 150° C. Heat resistance test | Transmittance (%) | A | A | A | A | A | A |
|  | YI | A | A | A | A | A | A |
| 180° C. Heat resistance test | Transmittance (%) | A | A | A | A | B | B |
|  | YI | A | A | A | A | B | B |

TABLE 11

|  |  | Cured Product 31 | Cured Product 32 | Cured Product 33 | Cured Product 34 | Cured Product 35 | Cured Product 36 |
|---|---|---|---|---|---|---|---|
| 400 nm Transmittance |  | A | A | A | A | A | A |
| 150° C. Heat resistance test | Transmittance (%) | A | A | A | A | A | A |
|  | YI | A | A | A | A | A | A |
| 180° C. Heat resistance test | Transmittance (%) | A | A | A | A | B | B |
|  | YI | A | A | A | A | B | B |

TABLE 12

|  |  | Cured Product 37 | Cured Product 38 | Cured Product 39 | Cured Product 40 | Cured Product 41 | Cured Product 42 |
|---|---|---|---|---|---|---|---|
| 400 nm Transmittance |  | A | A | A | A | A | A |

TABLE 12-continued

|  |  | Cured Product 37 | Cured Product 38 | Cured Product 39 | Cured Product 40 | Cured Product 41 | Cured Product 42 |
|---|---|---|---|---|---|---|---|
| 150° C. Heat resistance test | Transmittance (%) | A | A | A | A | A | A |
|  | YI | A | A | A | A | A | A |
| 180° C. Heat resistance test | Transmittance (%) | A | A | A | A | B | B |
|  | YI | A | A | A | A | B | B |

TABLE 13

|  |  | Cured Product 43 | Cured Product 44 | Cured Product 45 | Cured Product 46 | Cured Product 47 | Cured Product 48 |
|---|---|---|---|---|---|---|---|
| 400 nm Transmittance |  | A | A | A | A | A | A |
| 150° C. Heat resistance test | Transmittance (%) | A | A | A | A | A | A |
|  | YI | A | A | A | A | A | A |
| 180° C. Heat resistance test | Transmittance (%) | B | B | A | A | A | A |
|  | YI | B | B | A | A | A | A |

TABLE 14

|  |  | Cured Product 49 | Cured Product 50 | Cured Product 51 | Cured Product 52 | Cured Product 53 | Cured Product 54 |
|---|---|---|---|---|---|---|---|
| 400 nm Transmittance |  | A | A | A | A | A | A |
| 150° C. Heat resistance test | Transmittance (%) | A | A | A | A | A | A |
|  | YI | A | A | A | A | A | A |
| 180° C. Heat resistance test | Transmittance (%) | B | B | A | A | B | B |
|  | YI | B | B | A | A | B | B |

TABLE 15

|  |  | Cured Product 55 | Cured Product 56 | Cured Product 57 |
|---|---|---|---|---|
| 400 nm Transmittance |  | A | A | A |
| 150° C. Heat resistance test | Transmittance (%) | B | B | B |
|  | YI | B | B | B |
| 180° C. Heat resistance test | Transmittance (%) | C | C | B |
|  | YI | C | C | B |

<Adherence Test 1>

Each of the varnishes prepared in the preparation process of Cured Products 1 to 57 was coated on a glass substrate, and a 100 μm-thick cured film was formed under the conditions of Curing Method 1. An adherence test was performed using a crosscut tape method of 100 squares and a space interval of 1 mm in conformity with JIS K-5400 (1990), and the adherence was evaluated according to the following criteria. The results are shown in Tables 16 to 25.

A: The number of squares separated is 0.
B: The number of squares separated is from 1 to 70.
C: The number of squares separated is from 71 to 100.

<Adherence Test 2>

Each of the varnishes prepared in the preparation process of Cured Products 1 to 57 was caused to fill 5 LED-use silver lead frames when the reflector was polyphthalic amide (PPA), and fill 4 lead frames when the reflector was polyamide 9 (PA9T), and then cured under the conditions of Curing Method 2 to encapsulate the lead frame. The test was performed using a compact thermal shock chamber manufactured by ESPEC Corp. In the test, −40° C.×25 minutes and 105° C.×25 minutes were taken as one cycle and after continuous 50 cycles, the separation from the frame was observed and evaluated according to the following criteria. The results are shown in Tables 16 to 25.

A: The number of separations is 0.
B: The number of separations is 1.
C: The number of separations is 2 or more.

TABLE 16

|  | Cured Product 1 | Cured Product 2 | Cured Product 3 | Cured Product 4 | Cured Product 5 | Cured Product 6 |
|---|---|---|---|---|---|---|
| Glass | A | A | A | A | A | A |
| PPA | A | A | A | A | A | A |
| PA9T | A | A | B | B | A | A |

TABLE 17

|  | Cured Product 7 | Cured Product 8 | Cured Product 9 | Cured Product 10 | Cured Product 11 | Cured Product 12 |
|---|---|---|---|---|---|---|
| Glass | A | A | A | A | A | A |
| PPA | B | B | B | B | A | A |
| PA9T | A | A | A | A | B | B |

TABLE 18

|  | Cured Product 13 | Cured Product 14 | Cured Product 15 | Cured Product 16 | Cured Product 17 | Cured Product 18 |
|---|---|---|---|---|---|---|
| Glass | A | A | A | A | A | A |
| PPA | B | B | B | B | A | A |
| PA9T | B | B | B | B | A | A |

TABLE 19

|       | Cured Product 19 | Cured Product 20 | Cured Product 21 | Cured Product 22 | Cured Product 23 | Cured Product 24 |
|-------|---|---|---|---|---|---|
| Glass | A | A | A | A | A | A |
| PPA   | A | A | A | A | A | A |
| PA9T  | A | A | A | A | A | A |

TABLE 20

|       | Cured Product 25 | Cured Product 26 | Cured Product 27 | Cured Product 28 | Cured Product 29 | Cured Product 30 |
|-------|---|---|---|---|---|---|
| Glass | A | A | A | A | A | A |
| PPA   | A | A | A | A | A | A |
| PA9T  | A | A | A | A | A | A |

TABLE 21

|       | Cured Product 31 | Cured Product 32 | Cured Product 33 | Cured Product 34 | Cured Product 35 | Cured Product 36 |
|-------|---|---|---|---|---|---|
| Glass | A | A | A | A | A | A |
| PPA   | A | A | A | A | A | A |
| PA9T  | A | A | A | A | A | A |

TABLE 22

|       | Cured Product 37 | Cured Product 38 | Cured Product 39 | Cured Product 40 | Cured Product 41 | Cured Product 42 |
|-------|---|---|---|---|---|---|
| Glass | A | A | A | A | A | A |
| PPA   | A | A | A | A | A | A |
| PA9T  | A | A | A | A | A | A |

TABLE 23

|       | Cured Product 43 | Cured Product 44 | Cured Product 45 | Cured Product 46 | Cured Product 47 | Cured Product 48 |
|-------|---|---|---|---|---|---|
| Glass | A | A | A | A | A | A |
| PPA   | A | A | A | A | A | A |
| PA9T  | A | A | A | A | A | A |

TABLE 24

|       | Cured Product 49 | Cured Product 50 | Cured Product 51 | Cured Product 52 | Cured Product 53 | Cured Product 54 |
|-------|---|---|---|---|---|---|
| Glass | A | A | A | A | A | A |
| PPA   | A | A | A | A | B | B |
| PA9T  | A | A | A | A | B | B |

TABLE 25

|       | Cured Product 55 | Cured Product 56 | Cured Product 57 |
|-------|---|---|---|
| Glass | B | B | A |
| PPA   | C | C | A |
| PA9T  | C | C | A |

The results shown in Tables 6 to 15 reveal that the cured product obtained using the curable resin composition of this invention had the same initial transmittance and 150° C. heat yellowing resistance as those of a cured product using a curable resin composition where the silsesquioxane is replaced by A' (Cured Products 55 and 56) and exhibited superiority particularly in the 180° C. heat yellowing resistance as apparent from the comparison of Cured Products 1 to 54.

The results in Tables 16 to 25 reveal that the cured product obtained using the curable resin composition of this invention exhibited more excellent adherence to glass than a cured product using a curable resin composition where the silsesquioxane is replaced by A' (Cured Products 55 and 56). It is understood that when an LED-use silver lead frame (PPA, PA9T) was encapsulated, the adherence was enhanced as apparent from the comparison of Cured Products 1 to 48.

<Sulfur Gas Corrosion Resistance Test>

With respect to the varnishes prepared in the preparation process of Cured Products 1 to 57, the curable resin composition was injected into 16 power LED-use PPA resin packages each having a silver-plated bottom (Model No. 5050 D/G, manufactured by ENOMOTO Co., Ltd.) by means of a dispenser (Model No. MPP-1, manufactured by Musashi Engineering Inc.) and then heated/cured under the conditions that the curable resin composition is heated at 80° C. for 1 hour and further heated at 150° C. for 4 hours. This PPA resin package was placed in a glass vessel containing 0.2 g of sulfur powder. After 60 hours, the corrosion state of the PPA resin package was observed. The sulfur gas resistance was evaluated according to the following criteria. The results are shown in Tables 26 to 35.

A: No change in silver wiring.
B: Silver wiring is colored.
C: Silver wiring was changed to black.

<Water Vapor Barrier Property Test>

Each of the varnishes prepared in the preparation process of Cured Products 1 to 57 was injected between two U-shaped quartz substrates each laminated with a release film and after vacuum defoaming, a 1 mm-thick cured film was formed under the same conditions as above. The moisture permeability was measured by a cup method in conformity with JIS Z-0208 (1976) and evaluated according to the following criteria. The results are shown in Tables 26 to 35.

A: The water vapor permeability is from 0 to 10 (g/m$^2$·day).
B: The water vapor permeability is from 11 to 30 (g/m$^2$·day).
C: The water vapor permeability is 31 or more (g/m$^2$·day).

<Sulfur Gas Corrosion Resistance Test After 150° C. Heat Resistance Test>

With respect to the varnishes prepared in the preparation process of Cured Products 1 to 57, the curable resin composition was injected into 16 power LED-use PPA resin packages each having a silver-plated bottom (Model No. 5050 D/G, manufactured by ENOMOTO Co., Ltd.) by means of a dispenser (Model No. MPP-1, manufactured by Musashi Engineering Inc.) and then heated/cured under the conditions that the curable resin composition is heated at 80° C. for 1 hour and further heated at 150° C. for 4 hours. This PPA resin package was subjected to a heat resistance test of 150° C./500 hours and then placed in a glass vessel containing 0.2 g of sulfur powder. After 60 hours, the corrosion state of the PPA resin package was observed. The sulfur gas resistance was evaluated according to the following criteria. The results are shown in Tables 26 to 35.

A: No change in silver wiring.
B: Silver wiring is colored.
C: Silver wiring was changed to black.

<Water Vapor Barrier Property Test after 150° C. Heat Resistance Test>

The above described cured products were subjected to a heat resistance test of 150° C./500 hours and then similarly measured for the moisture permeability by a cup method in conformity with JIS Z-0208 (1976), and the moisture permeability was evaluated according to the following criteria. The results are shown in Tables 26 to 35.

A: The water vapor permeability is from 0 to 10 (g/m²·day).
B: The water vapor permeability is from 11 to 50 (g/m²·day).
C: The water vapor permeability is 50 or more (g/m²·day).

TABLE 26

| | Time (h) | Cured Product 1 | Cured Product 2 | Cured Product 3 | Cured Product 4 | Cured Product 5 | Cured Product 6 |
|---|---|---|---|---|---|---|---|
| Water vapor permeability (g/m²·24 h) | 0 | A | A | A | A | A | A |
| | 500 | A | A | A | A | A | A |
| Sulfur corrosion resistance test | 0 | A | A | A | A | A | A |
| | 500 | A | A | A | A | A | A |

TABLE 27

| | Time (h) | Cured Product 7 | Cured Product 8 | Cured Product 9 | Cured Product 10 | Cured Product 11 | Cured Product 12 |
|---|---|---|---|---|---|---|---|
| Water vapor permeability (g/m²·24 h) | 0 | A | A | A | A | A | A |
| | 500 | A | A | A | A | A | A |
| Sulfur corrosion resistance test | 0 | A | A | A | A | A | A |
| | 500 | A | A | A | A | A | A |

TABLE 28

| | Time (h) | Cured Product 13 | Cured Product 14 | Cured Product 15 | Cured Product 16 | Cured Product 17 | Cured Product 18 |
|---|---|---|---|---|---|---|---|
| Water vapor permeability (g/m²·24 h) | 0 | A | A | A | A | A | A |
| | 500 | A | A | A | A | A | A |
| Sulfur corrosion resistance test | 0 | A | A | A | A | A | A |
| | 500 | A | A | A | A | A | A |

TABLE 29

| | Time (h) | Cured Product 19 | Cured Product 20 | Cured Product 21 | Cured Product 22 | Cured Product 23 | Cured Product 24 |
|---|---|---|---|---|---|---|---|
| Water vapor permeability (g/m²·24 h) | 0 | A | A | A | A | A | A |
| | 500 | A | A | A | A | A | A |
| Sulfur corrosion resistance test | 0 | A | A | A | A | A | A |
| | 500 | A | A | A | A | A | A |

TABLE 30

| | Time (h) | Cured Product 25 | Cured Product 26 | Cured Product 27 | Cured Product 28 | Cured Product 29 | Cured Product 30 |
|---|---|---|---|---|---|---|---|
| Water vapor permeability (g/m²·24 h) | 0 | A | A | A | A | A | A |
| | 500 | A | A | A | A | A | A |
| Sulfur corrosion resistance test | 0 | A | A | A | A | A | A |
| | 500 | A | A | A | A | A | A |

TABLE 31

| | Time (h) | Cured Product 31 | Cured Product 32 | Cured Product 33 | Cured Product 34 | Cured Product 35 | Cured Product 36 |
|---|---|---|---|---|---|---|---|
| Water vapor permeability (g/m²·24 h) | 0 | A | A | A | A | A | A |
| | 500 | A | A | A | A | A | A |
| Sulfur corrosion resistance test | 0 | A | A | A | A | A | A |
| | 500 | A | A | A | A | A | A |

TABLE 32

| | Time (h) | Cured Product 37 | Cured Product 38 | Cured Product 39 | Cured Product 40 | Cured Product 41 | Cured Product 42 |
|---|---|---|---|---|---|---|---|
| Water vapor permeability (g/m²·24 h) | 0 | A | A | A | A | A | A |
| | 500 | A | A | A | A | A | A |
| Sulfur corrosion resistance test | 0 | A | A | A | A | A | A |
| | 500 | A | A | A | A | A | A |

TABLE 33

| Time (h) | Cured Product 43 | Cured Product 44 | Cured Product 45 | Cured Product 46 | Cured Product 47 | Cured Product 48 |
|---|---|---|---|---|---|---|
| Water vapor permeability (g/m² · 24 h) | 0 | A | A | A | A | A | A |
| | 500 | A | A | A | A | A | A |
| Sulfur corrosion resistance test | 0 | A | A | A | A | A | A |
| | 500 | A | A | A | A | A | A |

TABLE 34

| Time (h) | Cured Product 49 | Cured Product 50 | Cured Product 51 | Cured Product 52 | Cured Product 53 | Cured Product 54 |
|---|---|---|---|---|---|---|
| Water vapor permeability (g/m² · 24 h) | 0 | A | A | A | A | A | A |
| | 500 | A | A | A | A | A | A |
| Sulfur corrosion resistance test | 0 | A | A | A | A | A | A |
| | 500 | A | A | A | A | A | A |

TABLE 35

| Time (h) | Cured Product 55 | Cured Product 56 | Cured Product 57 |
|---|---|---|---|
| Water vapor permeability (g/m² · 24 h) | 0 | A | A | B |
| | 500 | C | C | B |
| Sulfur corrosion resistance test | 0 | A | A | C |
| | 500 | C | C | C |

The results shown in Tables 26 to 35 reveal that Cured Products 1 to 54 obtained using the curable resin composition of this invention exhibited superiority in the evaluation of sulfur gas resistance over Cured Products 55 and 56 for comparison where silsesquioxane was replaced by A'. In addition, superiority was exhibited in both evaluations of water vapor barrier property and sulfur gas resistance, compared to Cured Product 57 using a conventional silicone resin.

As demonstrated above, the curable resin composition of this invention is proved to have superiority in 180° C. heat yellowing resistance evaluation, adherence to glass and further, adherence when using an LED-use silver lead frame (PPA, PA9T) as a base material, and is found to have a higher performance in terms of many physical properties than before.

While the invention has been described in detail and with reference to specific embodiments thereof, it will be apparent to one skilled in the art that various changes and modifications can be made therein without departing from the spirit and scope of the invention. This application is based on Japan Patent Application no. 2012-204512 filed on Sep. 18, 2012 and Japan Patent Application no. 2013-090624 filed on Apr. 23, 2013, the contents of which are incorporated herein by way of reference.

The invention claimed is:

1. A silicon compound obtained by a hydrosilylation reaction of a compound (a), a compound (b) and a compound (c), wherein the compound (a) is at least one compound selected from the group consisting of compounds represented by formulae (a-1) to (a-5), the compound (b) is at least one compound selected from the group consisting of compounds represented by formulae (b-1) to (b-5), and the compound (c) is a compound represented by formula (c-1):

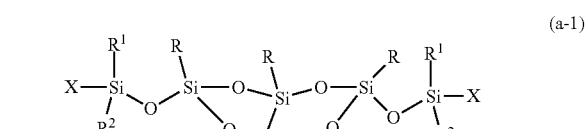

(a-1)

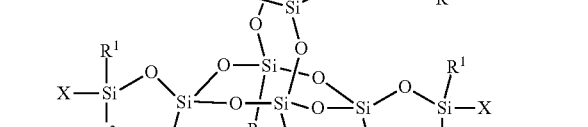

(a-2)

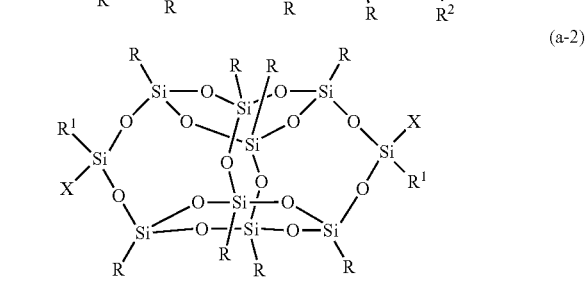

(a-3)

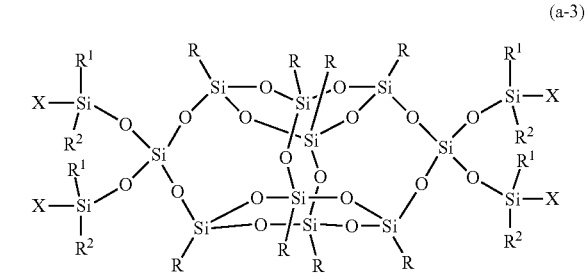

(a-4)

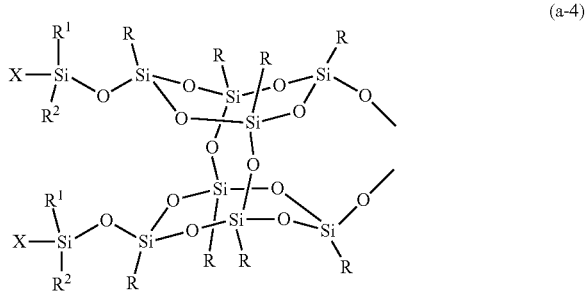

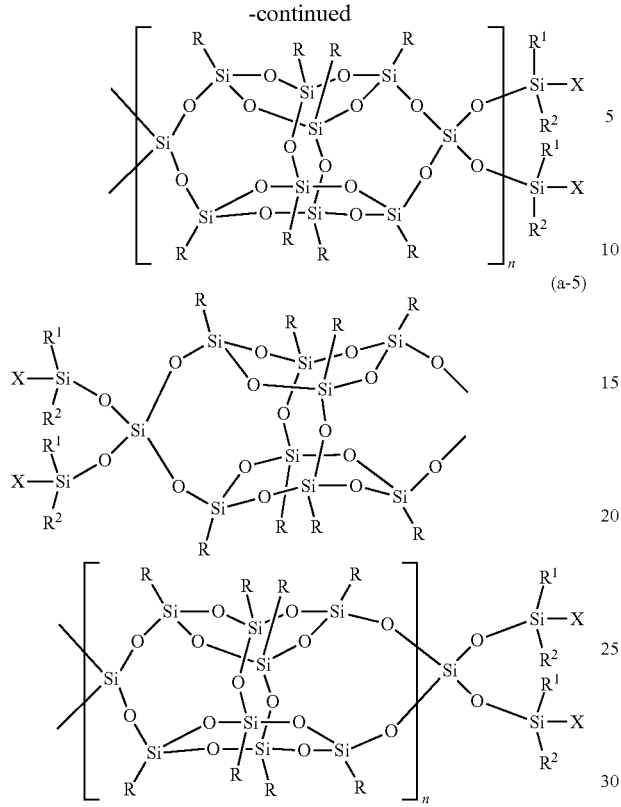

(a-5)

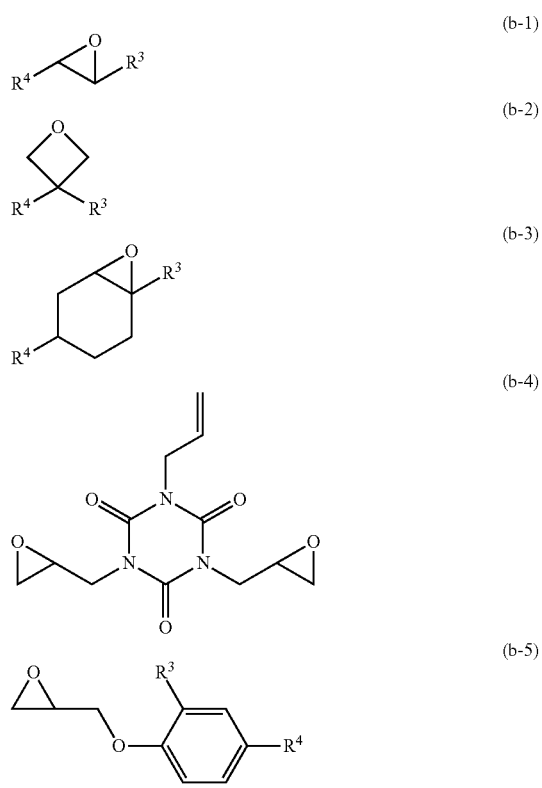

(b-1)

(b-2)

(b-3)

(b-4)

(b-5)

wherein in formulae (a-1) to (a-5),

- each R is a group independently selected from an alkyl having a carbon number of 1 to 45, a cycloalkyl having a carbon number of 4 to 8, an aryl having a carbon number of 6 to 14, and an arylalkyl having a carbon number of 7 to 24; in the alkyl having a carbon number of 1 to 45, at least one hydrogen may be replaced by fluorine, and at least one non-adjacent —$CH_2$— may be replaced by —O— or —CH=CH—; in a benzene ring of the aryl and arylalkyl, at least one hydrogen may be replaced by a halogen or an alkyl having a carbon number of 1 to 10, and in this alkyl having a carbon number of 1 to 10, at least one hydrogen may be replaced by fluorine, and at least one non-adjacent —$CH_2$— may be replaced by —O— or —CH=CH—; the carbon number of the alkylene in the arylalkyl is from 1 to 10, and at least one non-adjacent —$CH_2$— therein may be replaced by —O—;
- each $R^1$ is a group independently selected from an alkyl having a carbon number of 1 to 4, cyclopentyl, cyclohexyl and phenyl;
- at least two X in one molecule of each compound are hydrogen, with the remaining being a group independently selected from an alkyl having a carbon number of 1 to 4, cyclopentyl, cyclohexyl and phenyl;
- in formulae (a-1) and (a-3) to (a-5),
- each $R^2$ is a group independently selected from an alkyl having a carbon number of 1 to 4, cyclopentyl, cyclohexyl and phenyl;
- in formulae (a-4) and (a-5),
- n is an integer of 1 to 100;

wherein in formulae (b-1) to (b-3) and (b-5), either one of $R^3$ and $R^4$ is an alkenyl having a carbon number of 2 to 10 in which one —$CH_2$— may be replaced by —O— or 1,4-phenylene, and the other is hydrogen or an alkyl having a carbon number of 1 to 6; and

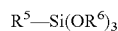

(c-1)

wherein in formula (c-1), $R^5$ is an alkenyl having a carbon number of 2 to 10, one —$CH_2$— in this alkenyl may be replaced by —O— or 1,4-phenylene, and $R^6$ is an alkyl having a carbon number of 1 to 6 or hydrogen.

2. The silicon compound of claim 1, wherein the compound (a) is a silsesquioxane derivative represented by formula (a-1-1):

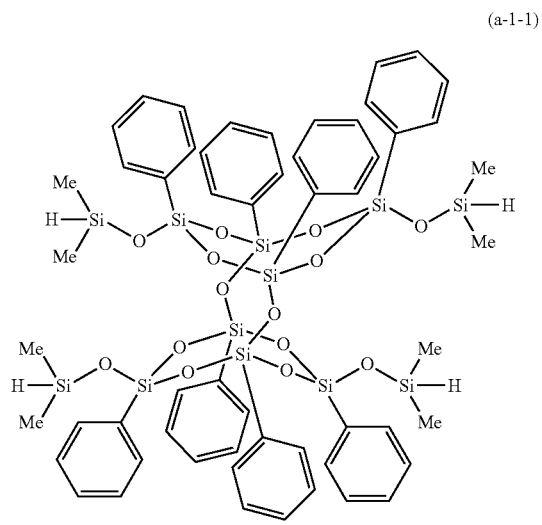 [SMILES: C[SiH](C)O[Si]1(c2ccccc2)O[Si]2(c3ccccc3)O[Si](O[SiH](C)C)(c3ccccc3)O[Si](c3ccccc3)(O1)O[Si]1(c3ccccc3)O[Si](O[SiH](C)C)(c3ccccc3)O[Si](c3ccccc3)(O[Si](O[SiH](C)C)(c3ccccc3)O1)O2]

(a-1-1)

wherein in formula (a-1-1), Me represents methyl.

3. The silicon compound of claim 1, wherein the compound (b) is at least one compound selected from the group consisting of compounds represented by formulae (b-1-1), (b-2-1) to (b-2-3), (b-3-1), (b-3-2), (b-4-1), (b-5-1) and (b-5-2):

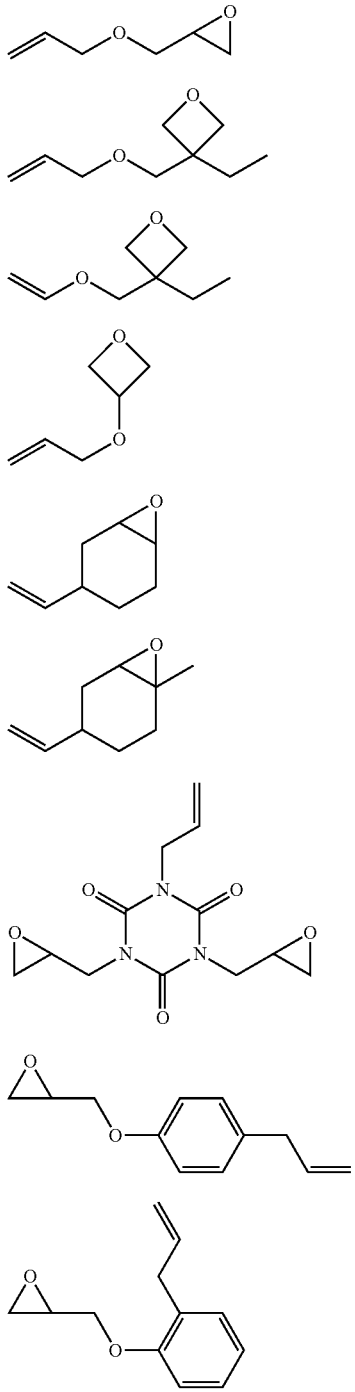

4. The silicon compound of claim 1, wherein the compound (c) is a compound represented by formula (c-1-1):

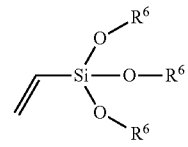

wherein in formula (c-1-1), $R^6$ is an alkyl having a carbon number of 1 to 6, or hydrogen.

5. A curable resin composition comprising:
 (A) the silicon compound of claim 1,
 (B) an epoxy and/or oxetane resin, and
 (C) a curing agent.

6. The curable resin composition of claim 5, wherein the silicon compound of (A) is a silsesquioxane represented by formula (α):

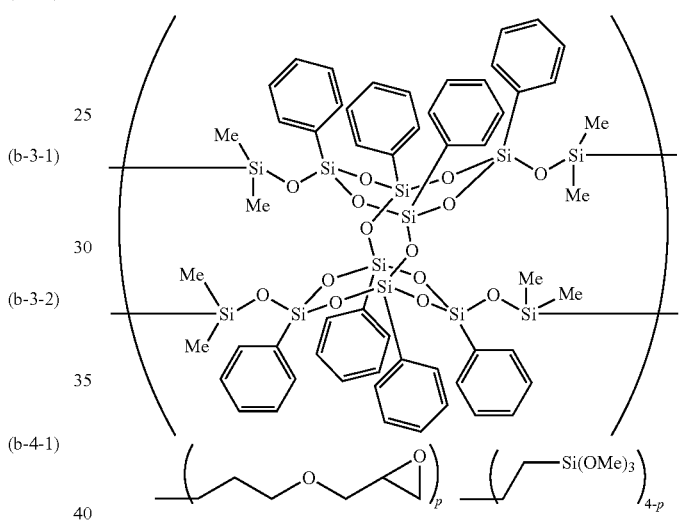

wherein in formula (α), p is a number satisfying 0<p<4.

7. The curable resin composition of claim 5, wherein the epoxy and/or oxetane resin of (B) is an epoxy and/or oxetane resin comprising no silicon atom in the molecule.

8. The curable resin composition of claim 5, wherein the curing agent of (C) is a photocationic or thermal cationic polymerization initiator, a metal chelate salt or an organic metal.

9. The curable resin composition of claim 5, further comprising a phosphor.

10. The curable resin composition of claim 9, wherein said phosphor is a phosphor for LED.

11. An LED encapsulant comprising the curable resin composition of-claim 5.

12. A seal material comprising the curable resin composition of claim 5.

13. A film-like, sheet-like or coating-like cured product obtained by coating the curable resin composition of claim 5 on a base material and curing the composition by heating or light irradiation.

14. An insulating film comprising the cured product of claim 13.

* * * * *